US008445663B2

(12) United States Patent
Sällberg et al.

(10) Patent No.: US 8,445,663 B2
(45) **Date of Patent: *May 21, 2013**

(54) COMPOSITIONS AND METHODS THAT ENHANCE AN IMMUNE RESPONSE

(75) Inventors: Matti Sällberg, Stockholm (SE); Lars Frelin, Älvsjö (SE)

(73) Assignee: Chrontech Pharma AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/146,755

(22) PCT Filed: Jan. 29, 2010

(86) PCT No.: PCT/IB2010/000324
§ 371 (c)(1),
(2), (4) Date: Jul. 28, 2011

(87) PCT Pub. No.: WO2010/086743
PCT Pub. Date: Aug. 5, 2010

(65) Prior Publication Data

US 2012/0039842 A1 Feb. 16, 2012

Related U.S. Application Data

(63) Continuation-in-part of application No. 12/371,898, filed on Feb. 16, 2009, now abandoned.

(60) Provisional application No. 61/149,299, filed on Feb. 2, 2009, provisional application No. 61/292,374, filed on Jan. 5, 2010.

(30) Foreign Application Priority Data

Feb. 16, 2009 (WO) .................. PCT/IB2009/005355

(51) Int. Cl.
*A61K 48/00* (2006.01)
*A61K 50/00* (2006.01)

(52) U.S. Cl.
USPC .................. 536/23.72; 424/202.1; 424/225.1; 424/93.1; 514/44

(58) Field of Classification Search
None
See application file for complete search history.

(56) References Cited

U.S. PATENT DOCUMENTS

| | | | | |
|---|---|---|---|---|
| 6,942,866 | B2 * | 9/2005 | Birkett | 424/268.1 |
| 7,022,830 | B2 * | 4/2006 | Sallberg | 536/23.72 |
| 2003/0206919 | A1 | 11/2003 | Sallberg | |
| 2008/0131452 | A1 | 6/2008 | Milich et al. | |

FOREIGN PATENT DOCUMENTS

| | | |
|---|---|---|
| WO | WO03/072722 A2 * | 9/2003 |
| WO | WO 2008/020656 | 2/2008 |
| WO | WO 2009/022236 | 2/2009 |

OTHER PUBLICATIONS

Billaud et al, "Advantages to the use of rodent hepadnavirus core proteins as vaccine platforms," Vaccine, Lesevier Ltd, vol. 25, No. 9, Jan. 19, 2007, pp. 1593-1606.

Sallberg M et al., "A Malaria vaccine candidate based on a hepatitis B virus core platform," Intervirology, Karger, vol. 45, No. 4-06, Jan. 1, 2002, pp. 350-361.

Young Min Park et al., "Monitoring antibody titers to recombinant core-ns3 fusion polypeptide is useful for evaluating hepatitis C virus infection and responses to interferon-alpha therapy," Journal of Korean Medical Science, Korean Academy of Medical Science, Seoul, Korea, vol. 14, No. 2, Apr. 1, 1999, pp. 165-170.

Nagata et al., "Codon optimization effect on translational efficiency of DNA vaccine in mammalian cells: Analysis of plasmid DNA encoding a CTL Epitope derived from microorganisms," Biochemical and Biophysical Research Communications, Academic Press Inc., vol. 261, No. 2, Aug. 2, 1999, pp. 445-451.

Frelin et al., "Codon optimization and mRNA amplification effectively enhances the immunogenicity of the hepatitis C virus nonstructural 3/4A gene," Gene Therapy, Macmillan Press Ltd., Basingstoke, GB, vol. 11, Jan. 1, 2004, pp. 522-533.

Database, Geneseq, {Online}, Apr. 30, 1999, "HCV NS3-NS4A protease and HBV antigen construct DNA DEQ. ID: 1184," XP002590182, retrieved from EBI accession No. GSN:AWI31632.

* cited by examiner

*Primary Examiner* — Bao Li

(74) *Attorney, Agent, or Firm* — Knobbe Martens Olson & Bear LLP

(57) ABSTRACT

Disclosed herein are isolated nucleic acids, compositions of isolated nucleic acids, and compositions of polypeptides that are useful for the generation, enhancement, or improvement of an immune response to a target antigen. Some embodiments of the compositions include hepatitis B core antigen (HBcAg) protein and a heterologous protein antigen. In some embodiments, an isolated nucleic acid encoding hepatitis B core antigen (HBcAg) protein and a heterologous protein antigen is disclosed. Also disclosed herein are methods of administering the composition or isolated nucleic acid to generate an immune response, where HBcAg acts as adjuvant to improve the immune response to the heterologous protein. In certain embodiments, the HBcAg is as a stork or heron hepatitis antigen.

18 Claims, 16 Drawing Sheets

ChronvacB / ChronvaC *in vitro* translation

Gel 1: 10% Tris-HCl SDS gel, 24h exposure

M: Rainbow marker
1: coNS3/4A (1)
2: C1, fusion protein (3)
3: C2, NS3 mutant (4)
4: C3, NS3 + NS4_HBc (5)
5: C4, NS3 + NS4 + HBc (6)
6: coHBc (2)

ChronvacB / ChronvaC *in vitro* translation

Gel 2: 10% Tris-HCl SDS gel, 24h exposure

M: Rainbow marker
1: coNS3/4A (1)
2: NS3 + NS4 + HBc fragm. (7)
3: NS3 + NS4 + HBc fragm. (8)
4: NS3 + NS4 + HBc fragm. (9)
5: NS3 + NS4 + HBc fragm. (10)
6: NS3 + NS4 + HBc fragm. (11)
7: coHBc (2)

COMPOSITIONS AND METHODS THAT ENHANCE AN IMMUNE RESPONSE

CROSS REFERENCE TO RELATED APPLICATIONS

This application claims the benefit and priority to and is a U.S. National Phase Application of PCT International Application Number PCT/IB2010/000324, filed on Jan. 29, 2010, designating the United States of America and published in the English language, which claims the benefit of priority to U.S. Provisional Application No. 61/292,374, filed Jan. 5, 2010, and U.S. Provisional Application No. 61/149,299, filed Feb. 2, 2009. This application is also a continuation-in-part of International Patent Application No. PCT/IB2009/005355, filed Feb. 16, 2009, which designated the United States and was published in English. This application is also a continuation-in-part of U.S. patent application Ser. No. 12/371,898, filed Feb. 16, 2009. The disclosures of the above-referenced provisional applications and international and domestic patent applications are hereby expressly incorporated by reference in their entireties.

REFERENCE TO SEQUENCE LISTING

The present application is being filed along with a Sequence Listing in electronic format. The Sequence Listing is provided as a file entitled TRIPEP116VPC.TXT, created Jan. 29, 2009, which is 360 KB in size. The information in the electronic format of the Sequence Listing is incorporated herein by reference in its entirety.

BACKGROUND

Traditionally, vaccines have been based on live attenuated or inactivated pathogens. These strategies are inefficient, however, largely because of the antigenic variability of pathogens (e.g., viruses). Several peptide vaccines that comprise antigenic peptides or peptide fragments of pathogens have been developed. Conserved peptide fragments are less likely to exhibit antigenic variability and can overcome some of the problems associated with traditional peptides. Accordingly, subunit vaccines have been developed, which target conserved regions of pathogens. Synthetic peptide vaccines tend to be poorly immunogenic, however. The poor immunogenicity of synthetic peptide vaccines may be attributed to the fact that although these types of vaccines induce humoral antibody responses, they are less likely to induce cell-mediated responses.

Several investigators have sought to improve the antigenicity of synthetic peptide vaccines. For example, Klein et al. describe the engineering of chimeric proteins that comprise an immunogenic region of a protein from a first antigen linked to an immunogenic region from a second pathogen. (See, U.S. Pat. Nos. 6,033,668; 6,017,539; 5,998,169; and 5,968,776). Others have sought to create chimeric proteins that couple B-cell epitopes to universal T-cell epitopes in order to improve the immune response. (See, e.g., U.S. Pat. No. 5,114, 713). Russell-Jones et al. (U.S. Pat. No. 5,928,644) also disclose T-cell epitopes derived from the TraT protein of Escherichia coli, which are used to produce hybrid molecules so as to generate an immune response to parasites, soluble factors (e.g., LSH) and viruses. Further, Ruslan (U.S. Patent Application Publication No. 20030232055) discloses the manufacture of vaccines based on PAMPs and immunogenic antigens.

The hepatitis B virus core antigen (HBcAg) is thought to be a key target for the host immune response in the control of the infection. In particular, the presence of HBcAg-specific T cells has been associated with clearance of acute and chronic infections with the hepatitis B virus (HBV). Subsequently, prophylactic and therapeutic vaccines that induce HBcAg-specific T cells have been developed and some have shown efficacy in infectious models. However, despite the high immunogenicity of exogenous HBcAg, many of the studies using endogenous HBcAg as a vaccine have been disappointing.

When expressed alone, HBcAg will spontaneously assemble into virus-like particles (VLPs) that are immunogenic in vivo. These VLPs interact with B cells as the primary antigen-presenting cell (APC) by an unusual interaction with the B cell receptor. HBcAg effectively primes specific T helper (Th) and, much less effectively, cytotoxic T cells (CTLs) as an exogenous antigen when high antigen doses in adjuvant are used. Both DNA- and retrovirus-based immunizations using HBcAg have been reported to induce detectable HBcAg-specific CTLs in mice. Some investigators have sought to use HBcAg VLPs as a platform to display heterogeneous antigens, as well, but these approaches have been hindered by poor assembly and instability of the particles. (See e.g., U.S. Pat. Nos. 4,818,527; 4,882,145; 5,143,726; 6,231,864; 6,887,464; 6,942,866; 7,144,712; 7,320,795; 7,351,413; and 7,361,352; the disclosures of which are hereby expressly incorporated by reference in their entireties).

DNA vaccines can be used as a model to study the endogenous immunogenicity of antigens. However, phase I/II clinical trials reveal that it is difficult to prime robust immune responses in humans with direct intramuscular injections of DNA vaccines. Different modes of DNA delivery have now become available, including transdermal delivery of DNA coated to gold beads using the gene gun or treatment of the injection site by in vivo electroporation. The need for approaches that enhance the immune response of a subject after vaccination, in particular DNA vaccination, is manifest.

SUMMARY OF THE INVENTION

Several embodiments described herein concern isolated nucleic acids, peptides, compositions and methods that are useful for the generation, enhancement, or improvement of an immune response to a target antigen. These compositions are particularly useful to enhance the immune response of a subject that receives a protein or nucleic acid-based immunogen (e.g., DNA immunogen or conventional protein-based vaccine). Although Hepatitis B virus core antigen (HBcAg) is a well known antigen, HBcAg or portions thereof have not been described for use as an adjuvant, which can be administered to a subject in conjunction with a protein or nucleic acid-based immunogen (e.g., a DNA vaccine) so as to improve the immune response to the protein or the protein encoded by the nucleic acid immunogen. In a first series of experiments disclosed herein, it was discovered that a nucleic acid encoding HBcAg improved the immune response of a subject to a co-administered nucleic acid encoding a hepatitis C virus (HCV) protein (NS3/4A).

In this disclosure, it is revealed that HBcAg, in particular non-human HBcAgs, such as those derived from an avian hepatitis virus, in particular, the virus that infects stork and heron, are uniquely suitable for enhancing an immune response of a subject to a co-administered antigen (e.g., a nucleic acid or peptide immunogen that is administered in a mixture with the HBcAg adjuvant or within approximately at least, equal to, or any number in between 1, 2, 3, 4, 5, 6, 7, 8, 9, 10, 11, 12, 13, 14, 15, 20, 30, 45, or 60 minutes before or after inoculation with the immunogen). It is contemplated that HBcAg and fragments thereof or a nucleic acid encoding these compositions are useful additions to immunogen preparations, which improve the immune response of a subject (e.g., a human or mammal) to the immunogen.

Preferably, an HBcAg derived from a hepatitis virus that does not infect a human (a "non-human HBcAg") or a nucleic acid encoding said non-human HBcAg is used as the adjuvant (e.g., an HBcAg derived from an avian hepatitis virus, such as the hepatitis virus that infects stork or heron (e.g., SEQ. ID. NOs. 20 and 22). HBV now afflicts almost a third of the world's population. Accordingly, a significant amount of the population has antibodies that react to an HBcAg derived from a hepatitis virus that infects humans. By utilizing HBcAg sequences derived from divergent hepatitis species, the compositions described herein can be made suitable for introduction into subjects that are already infected with HBV or subjects that have already generated antibodies to HBV (e.g., a subject that had been previously inoculated with an HBV vaccine). Additionally, when nucleic acids encoding an HBcAg or a fragment thereof (e.g., a nucleic acid encoding an HBcAg derived from an avian hepatitis virus that infects stork or heron) are administered, these sequences are, preferably, codon-optimized for expression in the subject (e.g., codon-optimized for expression in the particular animal or human (e.g., SEQ. ID. NOs. 20 and 22)).

Accordingly, several aspects of the invention described herein concern compositions that comprise, consist essentially of, or that consist of nucleic acids that encode an HBcAg of an avian hepatitis virus (e.g., a hepatitis virus that infects stork or heron (e.g., SEQ. ID. NO. 20 and 22)), which has been codon-optimized for expression in humans and, which can be joined (e.g., in Cis) to a nucleic acid (preferably codon-optimized for expression in an animal or human) that encodes a heterologous antigen (e.g., a non-HBV antigen or a non-hepatitis antigen), such as, SEQ. ID. NOs. 2, 8, 10, 12, 14, 16, and 18. In some embodiments, it is preferred that the nucleic acid that encodes a heterologous protein or heterologous protein antigen is inserted in a spike region of the encoded HbcAg (e.g., between amino acid residues of about 87 to about 129). Compositions or mixtures that comprise, consist essentially of, or that consist of nucleic acids (e.g., in Trans) that encode an HBcAg of an avian hepatitis virus (e.g., a hepatitis virus that infects stork or heron), which has been codon-optimized for expression in humans (e.g., SEQ. ID. NO. 20 and 22) and a nucleic acid (preferably codon-optimized for expression in an animal or human) that encodes a heterologous peptide antigen (e.g., a non-HBV peptide or a non-hepatitis peptide), such as SEQ. ID. NOs. 2, 8, 10, 12, 14, 16, and 18 are also embodiments. Methods of using the aforementioned compositions to improve, enhance, or generate an immune response in a subject are also contemplated.

Some embodiments disclosed herein include an immunogenic composition comprising an isolated nucleic acid, which is codon optimized for expression in humans, encoding a hepatitis B virus core antigen (HBcAg) or a fragment thereof that is at least 50 amino acids in length; and an isolated nucleic acid, which is codon optimized for expression in humans, encoding a heterologous protein antigen. In some embodiments, the HBcAg is a human hepatitis antigen. The HBcAg may, in some embodiments, be a stork hepatitis antigen. In certain embodiments, the HBcAg is a heron hepatitis antigen.

Certain aspects of the immunogenic compositions disclosed herein comprise a full-length HBcAg. In some embodiments, the immunogenic composition comprises a fragment of a HBcAg that is at least 75 amino acids in length. In some other embodiments, the immunogenic composition comprises a fragment of a HBcAg that is at least 125 amino acids in length. Some embodiments have an immunogenic composition that comprises a fragment of a HBcAg that is at least 150 amino acids in length. In still another embodiment, the immunogenic composition comprises a fragment of a HBcAg that is at least 175 amino acids in length.

Certain embodiments disclosed herein include an immunogenic composition where the heterologous protein is a viral antigen, plant antigen, or animal antigen. In some embodiments, the heterologous protein is a viral antigen. Certain aspects of the immunogenic composition include a viral antigen that is a hepatitis antigen. In some embodiments, the hepatitis antigen is a hepatitis C virus (HCV) antigen. In some embodiments, the HCV antigen comprises NS3/4A. In other embodiments, the HCV antigen comprises NS5A. In still other embodiments, the HCV antigen comprises NS3/4A and NS5A. In some embodiments, the hepatitis antigen comprises a hepatitis B virus (HBV) antigen that is non-naturally occurring or in a non-naturally occurring position with respect to said HBcAg or fragment thereof. Some embodiments have an HBV antigen that comprises a human HBV surface antigen, a human HBV e antigen, a human HBcAg, a human HBV polymerase antigen, or a human HBV x antigen.

In certain aspects, said HBcAg or fragment thereof is a stork or heron hepatitis antigen and said HBV antigen is a human HBcAg. In some aspects, said HBcAg is a stork or heron hepatitis antigen and said HBV antigen is a human HBV e antigen.

In some embodiments, the heterologous protein is a plant antigen. In certain embodiments, the plant antigen comprises a birch antigen. In some embodiments, the heterologous protein is an animal antigen. In some aspects, the animal antigen comprises an ovalbumin antigen.

In some embodiments, the immunogenic compositions disclosed herein includes said isolated nucleic acid, which is codon optimized for expression in humans, encodes a full-length HBcAg and said isolated nucleic acid, which is codon optimized for expression in humans, encodes a heterologous protein and both isolated nucleic acids are in the same nucleic acid construct.

Another embodiment includes the immunogenic compositions disclosed herein includes said isolated nucleic acid, which is codon optimized for expression in humans, encodes a HBcAg and said isolated nucleic acid, which is codon optimized for expression in humans, encodes a heterologous protein and said nucleic acids are in separate nucleic acid constructs.

In some embodiments of the immunogenic composition, said HBcAg is a human hepatitis antigen and said heterologous protein comprises a HCV NS3/4A. In certain aspects, said immunogenic composition comprises a nucleic acid of sequence SEQ. ID. NO. 10, SEQ. ID. NO.2, or SEQ. ID. NO. 75.

In some embodiments of the immunogenic composition, said HBcAg is a stork hepatitis antigen and said heterologous protein comprises a HCV NS3/4A. In certain aspects, said immunogenic composition comprises a nucleic acid of sequence SEQ. ID. NO. 24, SEQ. ID. NO.2, or SEQ. ID. NO. 24.

In some embodiments of the immunogenic composition, said HBcAg is a heron hepatitis antigen and said heterologous protein comprises a HCV NS3/4A. In certain aspects, said immunogenic composition comprises a nucleic acid of sequence SEQ. ID. NO. 22, SEQ. ID. NO.2, or SEQ. ID. NO. 32.

In some embodiments of the immunogenic composition, said HBcAg is a human hepatitis antigen and said heterologous protein comprises a HCV NS5A. In certain aspects, said immunogenic composition comprises a nucleic acid of sequence SEQ. ID. NO. 10 or SEQ. ID. NO. 8.

In some embodiments of the immunogenic composition, said HBcAg is a stork hepatitis antigen and said heterologous protein comprises a HCV NS5A. In certain aspects, said immunogenic composition comprises a nucleic acid of sequence SEQ. ID. NO. 20, SEQ. ID. NO.2, or SEQ. ID. NO. 28.

In some embodiments of the immunogenic composition, said HBcAg is a heron hepatitis antigen and said heterologous protein comprises a HCV NS5A. In certain aspects, said immunogenic composition comprises a nucleic acid of sequence SEQ. ID. NO. 22, SEQ. ID. NO. 8, or SEQ. ID. NO. 42.

In some embodiments of the immunogenic composition, HBcAg is a human hepatitis antigen and said heterologous protein comprises a HBV e antigen. In certain aspects, said immunogenic composition comprises a nucleic acid of sequence SEQ. ID. NO. 10, SEQ. ID. NO. 12, or SEQ. ID. No. 14.

In some embodiments of the immunogenic composition, said HBcAg is a stork hepatitis antigen and said heterologous protein comprises a HBV e antigen. In certain aspects, said immunogenic composition comprises a nucleic acid of sequence SEQ. ID. NO. 20, SEQ. ID. NO. 12, SEQ. ID. No. 14, SEQ. ID. NO. 44 or SEQ. ID. NO. 46.

In some embodiments of the immunogenic composition, said HBcAg is a heron hepatitis antigen and said heterologous protein comprises a HBV e antigen. In certain aspects, said immunogenic composition comprises a nucleic acid of sequence SEQ. ID. NO. 22, SEQ. ID. NO. 12, SEQ. ID. No. 14, SEQ. ID. NO. 48 or SEQ. ID. NO. 50.

In some embodiments of the immunogenic composition, said HBcAg is a stork hepatitis antigen and said heterologous protein comprises a HBcAg that is a human hepatitis antigen. In certain aspects, said immunogenic composition comprises a nucleic acid of sequence SEQ. ID. NO. 20, SEQ. ID. NO. 10, or SEQ. ID. NO. 52.

In some embodiments of the immunogenic composition, said HBcAg is a heron hepatitis antigen and said heterologous protein comprises a HBcAg that is a human hepatitis antigen. In certain aspects, said immunogenic composition comprises a nucleic acid of sequence SEQ. ID. NO. 22, SEQ. ID. NO. 10, or SEQ. ID. NO. 54.

In some embodiments of the immunogenic composition, said HBcAg is a human hepatitis antigen and said heterologous protein comprises a birch antigen. In certain aspects, said immunogenic composition comprises a nucleic acid of sequence SEQ. ID. NO. 10 or SEQ. ID. NO. 18.

In some embodiments of the immunogenic composition, said HBcAg is a stork hepatitis antigen and said heterologous protein comprises a birch antigen. In certain aspects, said immunogenic composition comprises a nucleic acid of sequence SEQ. ID. NO. 20, SEQ. ID. NO. 18, or SEQ. ID. NO. 56.

In some embodiments of the immunogenic composition, said HBcAg is a heron hepatitis antigen and said heterologous protein comprises a birch antigen. In certain aspects, said immunogenic composition comprises a nucleic acid of sequence SEQ. ID. NO. 22, SEQ. ID. NO. 18, or SEQ. ID. NO. 58.

In some embodiments of the immunogenic composition, said HBcAg is a human hepatitis antigen and said heterologous protein comprises an ovalbumin antigen. In certain aspects, said immunogenic composition comprises a nucleic acid of sequence SEQ. ID. NO. 10, or SEQ. ID. NO. 16.

In some embodiments of the immunogenic composition, said HBcAg is a stork hepatitis antigen and said heterologous protein comprises an ovalbumin antigen. In certain aspects, said immunogenic composition comprises a nucleic acid of sequence SEQ. ID. NO. 22, SEQ. ID. NO. 16, or SEQ. ID. NO. 60.

In some embodiments of the immunogenic composition, said HBcAg is a heron hepatitis antigen and said heterologous protein comprises an ovalbumin antigen. In certain aspects, said immunogenic composition comprises a nucleic acid of sequence SEQ. ID. NO. 22, SEQ. ID. NO. 16, or SEQ. ID. NO. 62.

In some embodiments of the immunogenic composition, said HBcAg is a stork or heron hepatitis antigen and said heterologous protein comprises HCV NS3/4A and NS5A, and an NS3 protease cleavage site between NS5A and said HBcAg.

Some embodiments of the immunogenic composition disclosed herein comprise an isolated HBcAg that is a stork or heron hepatitis antigen or a fragment thereof that is at least 50 amino acids in length and a heterologous protein, wherein said heterologous protein is in admixture with said HBcAg and not bound thereto. In some embodiments, the HBcAg is a stork hepatitis antigen. In some embodiments, the HBcAg is a heron hepatitis antigen.

Certain aspects of the immunogenic composition comprises a full-length HBcAg. Other aspects of the immunogenic composition comprises a fragment of a HBcAg that is at least 75 amino acids in length. In some embodiments, the immunogenic composition comprises a fragment of a HBcAg that is at least 125 amino acids in length. In some embodiments, the immunogenic composition comprises a fragment of a HBcAg that is at least 150 amino acids in length. In some embodiments, the immunogenic composition comprises a fragment of a HBcAg that is at least 175 amino acids in length.

In some embodiments, the heterologous protein is a viral antigen, plant antigen, or animal antigen. In some embodiments, the heterologous protein is a viral antigen. In some embodiments, the viral antigen is a hepatitis antigen. In certain embodiments, the hepatitis antigen is a hepatitis C virus (HCV) antigen. In still other embodiments, the HCV antigen comprises NS3/4A. In another embodiment, the HCV antigen comprises NS5A. In some embodiments, the HCV antigen comprises NS3/4A and NS5A. In some embodiments, the hepatitis antigen comprises a hepatitis B virus (HBV) antigen that is non-naturally occurring or in a non-naturally occurring position with respect to said HBcAg or fragment thereof.

In some aspects, the heterologous protein is a plant antigen. In some embodiments, the plant antigen comprises a birch antigen.

In some embodiments, the heterologous protein is an animal antigen. In an embodiment, the animal antigen comprises an ovalbumin antigen.

Some embodiments of the immunogenic composition disclosed herein, where the HBV antigen comprises a human HBV surface antigen, a human HBV e antigen, a human HBcAg, a human HBV polymerase antigen, or a human HBV x antigen. In some embodiments, said HBcAg or fragment thereof is a stork or heron hepatitis antigen and said HBV antigen is a human HBcAg. In some embodiments, said HBcAg is a stork or heron hepatitis antigen and said HBV antigen is a human HBV e antigen.

Some embodiments of the immunogenic composition of disclosed herein further comprise an isolated nucleic acid encoding a protein selected from the group consisting of interleukin (IL) 2, IL12, IL15, IL21, IL28b, galactose transferase (gal transferase), and a toll-like receptor ligand (TLR) or an adjuvant selected from the group consisting of IL2, IL12, IL15, IL21, IL28b, gal transferase, a TLR, ribavirin, alum, CpGs, and an oil.

Some embodiments include an isolated nucleic acid encoding an HBcAg fusion protein comprising an isolated nucleic acid, which is codon optimized for expression in humans, encoding a hepatitis B virus core antigen (HBcAg) or a fragment thereof that is at least 50 amino acids in length joined to an isolated nucleic acid, which is codon optimized for expression in humans, encoding a heterologous protein.

In some embodiments, the HBcAg is a human hepatitis antigen. In still another embodiment, the HBcAg is a stork hepatitis antigen. In some embodiments, the HBcAg is a heron hepatitis antigen.

In some embodiments, the nucleic acid comprises a full-length HBcAg. In other embodiments, the nucleic acid comprises a fragment of a HBcAg that is at least 75 amino acids in length. In some embodiments, the nucleic acid comprises a fragment of a HBcAg that is at least 125 amino acids in length. In some other embodiments, the nucleic acid comprises a fragment of a HBcAg that is at least 150 amino acids in length. In another embodiment, the nucleic acid comprises a fragment of a HBcAg that is at least 175 amino acids in length.

In certain aspects of the isolated nucleic acid disclosed herein, the heterologous protein is a viral antigen, plant antigen, or animal antigen. In some embodiments, the heterologous protein is a viral antigen. In some embodiments, the viral antigen is a hepatitis antigen. In certain embodiments, the hepatitis antigen is a hepatitis C virus (HCV) antigen. In some embodiments, the HCV antigen comprises NS3/4A. In some embodiments, the HCV antigen comprises NS5A. In some other embodiments, the HCV antigen comprises NS3/4A and NS5A. In an embodiment, the hepatitis antigen comprises a hepatitis B virus (HBV) antigen that is non-naturally occurring or in a non-naturally occurring position with respect to said HBcAg or fragment thereof. In some embodiments, the HBV antigen comprises a human HBV surface antigen, a human HBV e antigen, a human HBcAg, a human HBV polymerase antigen, or a human HBV x antigen.

In some embodiments, heterologous protein is a plant antigen. In an embodiment, the plant antigen comprises a birch antigen.

In some embodiments, the heterologous protein is an animal antigen. In certain aspects, the animal antigen comprises an ovalbumin antigen.

In some embodiments, said HBcAg or fragment thereof is a stork or heron hepatitis antigen and said HBV antigen is a human HBcAg. In some embodiments, said HBcAg is a stork or heron hepatitis antigen and said HBV antigen is a human HBV e antigen.

Some embodiments of isolated nucleic acid include nucleic acid is selected from the group consisting of SEQ. ID. Nos. 24, 26, 28, 30, 32, 34, 36, 38, 40, 42, 44, 46, 48, 50, 51, 52, 54, 56, 58, 60, 62, 64, 66, 68, 73, 75, 77, 79, 81, 83, 85, 87, 89, 103 and 105.

Some embodiments disclosed herein are proteins encoded by the isolated nucleic acid of disclosed herein.

Certain aspects of the present invention include the use of a nucleic acid, protein, or immunogenic composition disclosed herein to prepare a medicament for generating an immune response in a subject to said heterologous protein.

Some embodiments disclosed herein are a method of using one or more of the compositions disclosed herein to produce an immune response in a subject comprising providing one or more of the compositions disclosed herein; and administering said composition to said subject.

Some embodiments disclosed herein are a method of improving an immune response to a heterologous protein in a subject comprising providing one or more of the compositions disclosed herein; administering said composition to said subject; and measuring an immune response to said heterologous protein.

In some embodiments, the methods disclosed herein have said composition is administered by injection. In some embodiments, said injection is intra muscular, dermal, or subdermal. In some embodiments, the method further comprises providing an electrical stimulation. In certain aspects, said electrical stimulation is electroporation.

In some embodiments, the methods include said isolated nucleic acid that encodes a full-length HBcAg is provided and the isolated nucleic acid that encodes a full-length HBcAg is administered separately from the isolated nucleic acid that encodes a heterologous protein. In some embodiments, the methods include said isolated nucleic acid that encodes a full-length HBcAg is administered before said isolated nucleic acid that encodes a heterologous protein.

Some embodiments of the methods disclosed herein, wherein an isolated nucleic acid that encodes a full-length HBcAg is provided and the isolated nucleic acid that encodes a full-length HBcAg is administered in admixture with the isolated nucleic acid that encodes a heterologous protein.

Some embodiments include an immunogenic composition comprising a nucleic acid, which is codon-optimized for expression in humans, encoding a hepatitis B virus core antigen (HBcAg) and a heterologous protein antigen.

Some embodiments include an immunogenic composition comprising a hepatitis B virus core antigen (HBcAg) protein and a nucleic acid, which is codon-optimized for expression in humans, encoding heterologous protein antigen.

In some embodiments, said nucleic acid encoding HBcAg or said HBcAg protein is derived from stork or heron hepatitis virus.

Some embodiments include a method of promoting an immune response in a subject comprising coadministering a nucleic acid, which is codon-optimized for expression in humans, encoding a hepatitis B virus core antigen (HBcAg) and a heterologous protein antigen.

Some embodiments include a method of promoting an immune response in a subject comprising: coadministering a hepatitis B virus core antigen (HBcAg) protein and a nucleic acid, which is codon-optimized for expression in humans, encoding a heterologous protein antigen

DETAILED DESCRIPTION

Figure 1A:
FIGS. 1(*a-i*) illustrate constructs encoding HBcAg and HCV NS3/N4A.
Figure 1B:
Figure 1C:
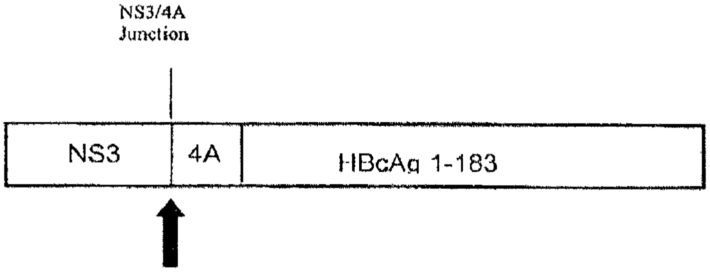
Figure 1D:
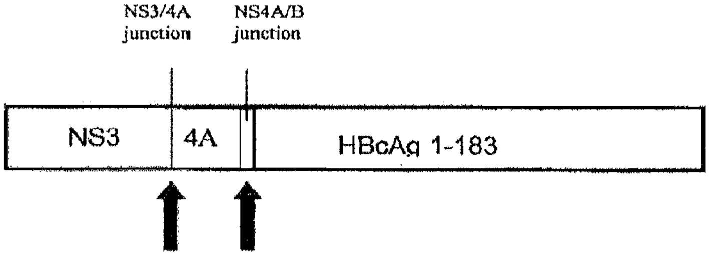
Figure 1E:
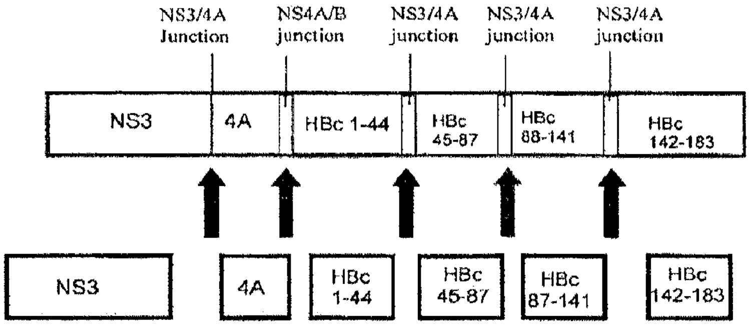
Figure 1F:
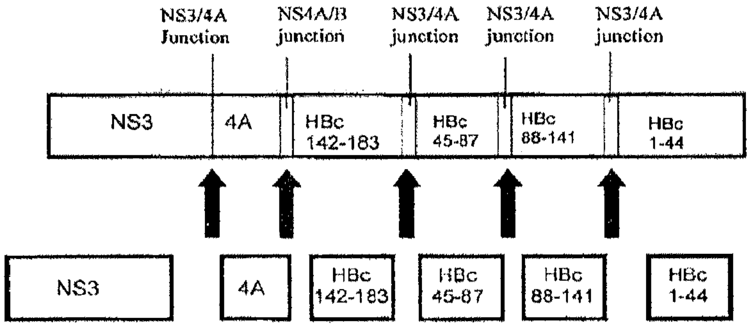
Figure 1G:
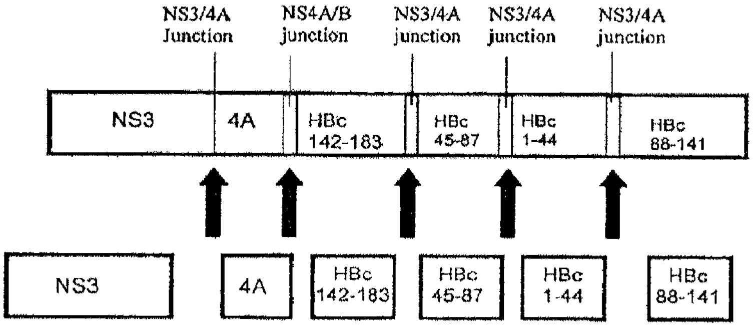
Figure 1H:
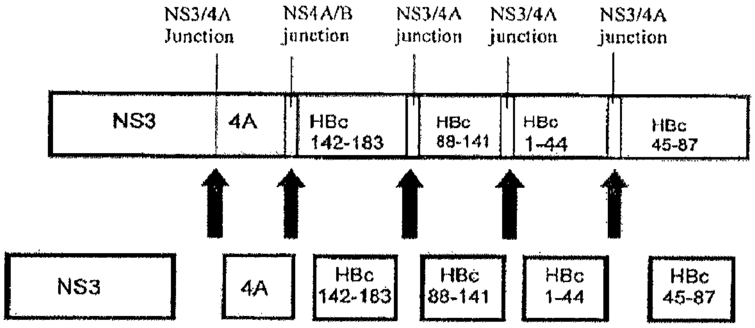
Figure 1I:
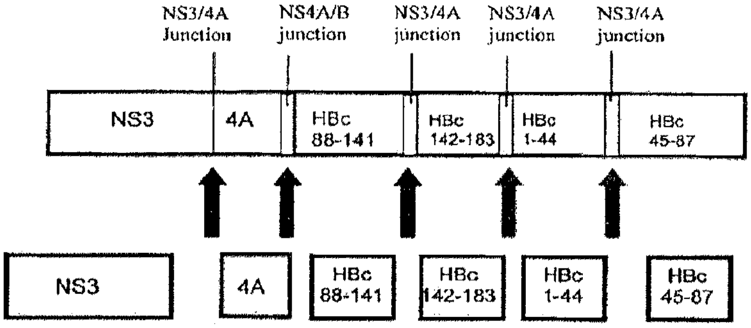

It has been discovered that hepatitis B core antigen (HBcAg) is a potent adjuvant that improves the immune response of a subject to a co-administered antigen. Disclosed herein are the results of experiments that revealed that a nucleic acid encoding HBcAg improved the immune response of a mammal to a co-administered nucleic acid encoding a hepatitis C virus (HCV) protein (NS3/4A). Accordingly, some embodiments include methods enhancing or improving an immune response of a subject, wherein an HBcAg or a nucleic acid encoding an HBcAg is provided to a subject in a mixture with a peptide immunogen or a nucleic acid encoding a peptide immunogen. In some embodiments, the peptide immunogen or nucleic acid encoding a peptide immunogen is provided in Cis with the HBcAg (e.g., a fusion protein encoding HBcAg joined to a desired peptide antigen or a nucleic acid encoding said fusion protein, see for example SEQ. ID. Nos 24, 26, 28, 30, 32, 34, 36, 38, 40, 42, 44, 46, 48, 50, 51, 52, 54, 56, 58, 60, 62, 64, 66, 68 and 73, 75, 77, 79, 81, 83, 85, 87 and 89). In other embodiments, the peptide immunogen or nucleic acid encoding a peptide immunogen is provided in Trans with the HBcAg (e.g., HBcAg or a nucleic acid encoding HBcAg (e.g., SEQ. ID. NO. 10, 20 and 22) is provided in a mixture or co-administered with a desired peptide antigen or a nucleic acid encoding said desired peptide antigen (e.g., SEQ. ID. NOs. 2, 8, 10, 12, 14, 16, and 18). Preferably, the compositions described herein comprise, consist essentially of, or consist of an "avian HBcAg," that is an HBcAg derived from a hepatitis virus that infects a bird, such as stork or heron). It is contemplated that the use of avian HBcAg in the compositions described herein will allow the formulation of immunogenic compositions that are suitable for administration to HBV infected individuals or subjects that have antibodies specific for HBV, since antibodies specific for an HBV that infects humans ("human HBV") generally do not cross-react with the HBV that infects avian species, such as stork and heron. Additionally, it is preferred that the nucleic acid sequences used in the compositions and methods disclosed herein are codon-optimized for expression in the subject to which the immunogenic compositions are to be administered (e.g., humans).

Accordingly, one or more of the compositions described herein can be used to improve, enhance or generate an immune response in a subject. By some approaches, a subject in need of an immune response to a particular antigen is identified. The identification step can be accomplished by diagnostic approaches or clinical evaluation (e.g., a subject in need of an immune response to HCV can be identified by diagnostic test or clinical evaluation). Next, one or more of the HBcAg—containing compositions described herein is provided to the identified subject. In some embodiments, the composition comprises an HBcAg protein or fragment thereof that is at least, equal to or any number in between about 20, 30, 40, 50, 60, 70, 80, 90, 100, 150, or more amino acids (e.g., HBcAg from a hepatitis that infects birds or humans) and an antigen to which an immune response is desired (e.g., an HCV protein, such as NS3/4A or NS5A). In other embodiments, the composition comprises a nucleic acid that encodes an HBcAg protein or a fragment thereof that is at least, equal to, or any number in between about 20, 30, 40, 50, 60, 70, 80, 90, 100, 200, 250, 300, or more amino acids (e.g., HBcAg from a hepatitis that infects birds or humans) and a nucleic acid encoding an antigen to which an immune response is desired (e.g., an HCV protein, such as NS3/4A or NS5A). In more embodiments, the composition comprises an HBcAg protein or fragment thereof that is at least, equal to or any number in between about 20, 30, 40, 50, 60, 70, 80, 90, 100, 150 or more amino acids (e.g., HBcAg from a hepatitis that infects birds or humans) and a nucleic acid encoding an antigen to which an immune response is desired (e.g., an HCV protein, such as NS3/4A or NS5A). In still more embodiments, the composition comprises a nucleic acid that encodes an HBcAg protein or a fragment thereof that is at least, equal to, or any number in between about 20, 30, 40, 50, 60, 70, 80, 90, 100, 150, or more amino acids (e.g., HBcAg from a hepatitis that infects birds or humans) and an antigen to which an immune response is desired (e.g., an HCV protein, such as NS3/4A or NS5A). Preferably, the compositions described above utilize an HBcAg protein or nucleic acid encoding an HBcAg protein that is derived from an avian hepatitis virus, such as stork or heron (e.g., SEQ. ID. NO. 20 and 22). Preferably, the peptide antigens or nucleic acids encoding said peptide antigens are hepatitis antigens, such as HCV antigens (e.g., NS3/4A or NS5A), HBV antigens (e.g., HBV surface antigen, HBV e antigen, human HBcAg, a human HBV polymerase antigen, a human HBV x antigen) or said peptide antigens or nucleic acids encoding said peptide antigens are birch allergens. Exemplary constructs and nucleic acids encoding preferred antigens, which can be used in one or more of the compositions and methods described herein are provided in SEQ. ID. NOs. 2, 8, 10, 12, 14, 16, and 18. Optionally, any of the aforementioned approaches can further include the step of measuring the immune response of the subject before, during, and after administration of the immunogenic composition. Such measurements can be made, for example, by diagnostic evaluation of viral titer in the case of viral disease, clinical evaluation, and scratch tests as are used when evaluating the response to allergens.

Generally, the generation, enhancement, or improvement of an immune response refers to an induction of a humoral (antibody) response and/or a cellular response. Most simply, an increase in the amount of antigen-specific antibodies (e.g., total IgG) can be seen by utilizing one or more of the embodiments described herein. Enhancement of an immune response also refers to any statistically significant change in the level of one or more immune cells (T cells, B cells, antigen-presenting cells, dendritic cells and the like) or in the activity of one or more of these immune cells (cytotoxic T lymphocyte (CTL) activity, helper T lymphocyte (HTL) activity, cytokine secretion, change in profile of cytokine secretion). The skilled artisan will readily appreciate that several methods for measuring or establishing whether an immune response is generated, enhanced, or improved are available. A variety of methods for detecting the presence and levels of an immune response are available, for example. (See, e.g., Current Protocols in Immunology, Ed: John E. Coligan, et al. (2001) John Wiley & Sons, NY, N.Y.; Current Protocols in Molecular Biology, (2001), Greene Publ. Assoc. Inc. & John Wiley & Sons, NY, N.Y.; Ausubel et al. (2001) Current Protocols in Molecular Biology, Greene Publ. Assoc. Inc. & John Wiley & Sons, Inc., NY, N.Y.; Sambrook et al. (1989) Molecular Cloning, Second Ed., Cold Spring Harbor Laboratory, Plainview, N.Y.); Maniatis et al. (1982) Molecular Cloning, Cold Spring Harbor Laboratory, Plainview, N.Y.; and elsewhere). Illustrative methods useful in this context include intracellular cytokine staining (ICS), ELISPOT, proliferation assays, cytotoxic T cell assays including chromium release or equivalent assays, and gene expression analysis using any number of polymerase chain reaction (PCR) or RT-PCR based assays. For example, the number of $CD8^+$ T-cells specific for a particular antigen or T-cell epitope (TCE) can be measured by flow cytometry. (See, e.g., Frelin et al. (2004) Gene Therapy 11:522-533). CTL priming can also be measured in vivo by, for example, a tumor inhibition model, in which the ability of an animal (e.g., mouse) to inhibit growth of tumors derived from tumor cells engineered to express the antigen of interest. Id.

In some embodiments, generation or enhancement of an immune response comprises an increase in target-specific CTL activity of between 1.5 and 5 fold in a subject that is provided a composition that comprises the nucleic acids or polypeptides disclosed herein (e.g., in the context of a HBcAg nucleic acid or polypeptide), wherein the TCE is derived from the target, as compared to the same TCE that is not provided in the context of the compositions disclosed herein. In some embodiments, an enhancement of an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject that is provided a composition that comprises a nucleic acid or a polypeptide disclosed herein (e.g., in the context of a HBcAg nucleic acid or polypeptide), wherein the TCE is derived from the target, as compared to administration of the same TCE that is not provided in the context of the compositions disclosed herein.

In other embodiments, an alteration of an immune response comprises an increase in target-specific HTL activity, such as proliferation of helper T cells, of between 1.5 and 5 fold in a subject that is provided a composition that comprises a nucleic acid or polypeptide disclosed herein (e.g., in the context of a HBcAg nucleic acid or polypeptide), wherein the TCE is derived from the target, as compared to the same TCE that is not provided in the context of the compositions disclosed herein. In some embodiments, alteration of an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject that is provided a composition that comprises a nucleic acid or polypeptide disclosed herein (e.g., in the context of a HBcAg nucleic acid or polypeptide), wherein the TCE is derived from the target, as compared to administration of the same TCE that is not provided in the context of the compositions disclosed herein. In this context, an enhancement in HTL activity may comprise an increase as described above, or decrease, in production of a particular cytokine, such as interferon-gamma (IFNγ), interleukin-1 (IL-1), IL-2, IL-3, IL-6, IL-7, IL-12, IL-15, tumor necrosis factor-alpha (TNFα), granulocyte macrophage colony-stimulating factor (GM-CSF), granulocyte -colony stimulating factor (G-CSF), or other cytokine. In this regard, generation or enhancement of an immune response may comprise a shift from a Th2 type response to a Th1 type response or in certain embodiments a shift from a Th1 type response, to a Th2 type response. In other embodiments, the generation or enhancement of an immune response may comprise the stimulation of a predominantly Th1 or a Th2 type response.

In still more embodiments, an increase in the amount of antibody specific for the antigen (e.g., total IgG) is increased. Some embodiments, for example, generate an increase in heterologous target-specific antibody production of between 1.5, 2, 3, 4, or 5 fold in a subject that is provided a composition comprising the nucleic acids or polypeptides disclosed herein, (e.g., in the context of a HBcAg nucleic acid or polypeptide), wherein the TCE is derived from the target, as compared to the same TCE that is not present in the context of the compositions disclosed herein. In some embodiments, the increase in heterologous target-specific antibody production is about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject that is provided a composition that comprises a nucleic acid or polypeptide disclosed herein, (e.g., in the context of a HBcAg nucleic acid or polypeptide), wherein the TCE is derived from the target, as compared to as compared to administration of the same TCE that is not present in the context of the compositions disclosed herein.

Generation or enhancement of a cellular immune response can also refer to the frequency of cytotoxic T lymphocytes (CTLs) specific for a desired antigen that are primed, or the rapidity of priming of cytotoxic T lymphocytes (CTLs) specific for a desired antigen, compared to the priming of CTLs specific for the desired epitope when the epitope is not presented in the context of the nucleic acids or peptides disclosed herein. The section below describes several of the HBcAg and heterologous protein sequences that can be used in the compositions and methods described herein.

Isolated Nucleic Acids and Proteins

Disclosed herein are compositions that comprise isolated nucleic acids encoding HBcAg, or a fragment thereof, joined to (e.g., flanking or juxtaposed to) an isolated nucleic acid encoding a heterologous protein. Accordingly, the isolated nucleic acid may, in some embodiments, encode a fusion protein that includes at least a fragment of HBcAg, and a heterologous protein. Polypeptides encoded by said isolated nucleic acids are also embodiments of the present invention.

FIG. 1(*a-i*) shows various embodiments of constructs that include HBcAg joined to HCV NS3/4A, which is an exemplary heterologous protein (and an antigen) within the scope of the present invention. FIG. 1*a* shows an exemplary construct having HCV NS3/4A joined to HBcAg, which is exemplified by SEQ. ID. No. 22. The sequence includes portions that encode HCV NS3/4A juxtaposed to HBcAg, and therefore encode a fusion protein (e.g., SEQ. ID. No. 23 encoded in SEQ. ID. No. 24). Similarly, FIG. 1*b* shows another construct having HCV NS3/4A joined to HBcAg, which encodes a mutant NS3 polypeptide and is exemplified by SEQ. ID. No. 26

FIGS. 1(*c-i*) show various embodiments of constructs that include HBcAg joined to HCV NS3/4A, where one or more cleavage sites are encoded between portions of the polypeptides encoded thereon. FIG. 1(*c*) encodes an NS3/4A junction between the NS3 and NS4A, and therefore encodes a protein configured to be cleaved by NS3 protease to provide an NS3 polypeptide, and an NS4A-HBcAg fusion protein. SEQ. ID. No. 38 is an exemplary sequence encoding the protein in SEQ. ID. No. 37 and includes the same features as the construct shown in FIG. 1(*c*). Furthermore, FIG. 1(*d*) shows a construct having two cleavage sites, where the construct encodes a protein that may be cleaved to form NS3, NS4A and HBcAg polypeptides. SEQ. ID. No. 64 exemplifies a nucleic acid sequence sharing the same features shown in FIG. 1(*d*). Finally, FIGS. 1(*e-i*) show embodiments of constructs 5 cleavage sites positioned between various portions of the encoded polypeptide. These constructs include 3 cleavage sites between fragments of HBcAg, and therefore encode a polypeptide configured to be cleaved by NS3 protease to form at least 4 fragments of HBcAg. Non-limiting examples of the constructs disclosed in FIGS. 1(*e-i*) are SEQ. ID. Nos. 81, 83, 85, 87 and 89, respectively.

The nucleocapsid or core antigen HBcAg of HBV is an immunogenic particle composed of 180 subunits of a single protein chain. HBcAg has been disclosed as an immunogenic moiety that stimulates the T cell response of an immunized host animal. See, e.g, U.S. Pat. No. 4,818,527, U.S. Pat. No. 4,882,145 and U.S. Pat. No. 5,143,726, each of which is hereby incorporated by reference in their entirety. It can be used as a carrier for several peptidic epitopes covalently linked by genetic engineering as well as for chemically coupled protein antigens. (See Sällberg et al. (1998) Human Gene Therapy 9:1719-29). In addition, HBcAg is non-cytotoxic in humans. Accordingly, it was contemplated that HBcAg is useful in genetic constructs for generating or enhancing an immune response to an accompanied target antigen (e.g., in constructs that encode a TCE derived from a pathogen).

Current listings of exemplary HBcAg sequences are publicly available at the National Center for Biotechnology Information (NCBI) world-wide web site. HBcAg nucleic acid sequences (including novel HBcAg regions) can also be isolated from subjects (e.g., humans) infected with HBV. DNA obtained from a patient infected with HBV can be amplified using PCR or another amplification technique.

For a review of PCR technology, see Molecular Cloning to Genetic Engineering White, B. A. Ed. in *Methods in Molecular Biology* 67: Humana Press, Totowa (1997) and the publication entitled "PCR Methods and Applications" (1991, Cold Spring Harbor Laboratory Press). For amplification of mRNAs, it is within the scope of the invention to reverse transcribe mRNA into cDNA followed by PCR (RT-PCR); or, to use a single enzyme for both steps as described in U.S. Pat. No. 5,322,770. Another technique involves the use of Reverse Transcriptase Asymmetric Gap Ligase Chain Reaction (RT-AGLCR), as described by Marshall R. L. et al. (*PCR Methods and Applications* 4:80-84, 1994).

The source of the HBcAg sequences that are included in the isolated nucleic acids described herein is not particularly limited. Accordingly, embodiments described herein may utilize an isolated nucleic acid that encodes an HBcAg derived from a hepatitis virus capable of infecting animals of any species, including but limited to, humans, non-human primates (e.g., baboons, monkeys, and chimpanzees), rodents, mice, reptiles, birds (e.g., stork and heron), pigs, micro-pigs, goats, dogs and cats. In some embodiments, the HBcAg is selected from a human hepatitis antigen or an avian hepatitis antigen. Particularly preferred are the stork hepatitis antigen and a heron hepatitis antigen.

In certain embodiments, the HBcAg sequences described herein have variations in nucleotide and/or amino acid sequences, compared to native HBcAg sequences and are referred to as HBcAg variants or mutants. As used herein, the term "native" refers to naturally occurring HBV sequences (e.g., available HBV isotypes). Variants may include a substitution, deletion, mutation or insertion of one or more nucleotides, amino acids, or codons encoding the HBcAg sequence, which may result in a change in the amino acid sequence of the HBcAg polypeptide, as compared with the native sequence. Variants or mutants can be engineered, for example, using any of the techniques and guidelines for conservative and non-conservative mutations set forth, for instance, in U.S. Pat. No. 5,364,934, which is hereby incorporated by reference in its entirety.

Accordingly, when the term "consisting essentially of" is used, in some contexts, variants or mutants of an HBcAg sequence or of a particular antigen sequence are intended to be encompassed. That is, in some contexts and in some embodiments, the variants or mutants of the sequences disclosed herein (e.g., SEQ. ID. No. 10) are equivalents because the variation or mutation in sequence does not change or materially affect the basic and novel characteristics of the claimed invention.

A codon-optimized HBcAg can, in some embodiments, be encoded within the isolated nucleic acid. A codon-optimized sequence may, in some embodiments, be obtained by substituting codons in an existing sequence with codons more frequently used in the intended host subject (e.g., a human). Some examples include, but are not limited to, codon-optimized nucleic acids encoding human HBcAg (e.g., SEQ. ID. No. 10), codon-optimized nucleic acids encoding stork HBcAg (e.g., SEQ. ID. No. 20), and codon-optimized nucleic acids encoding heron HBcAg (e.g., SEQ. ID. No. 22).

The isolated nucleic acids can encode the full-length HBcAg in certain embodiments (e.g., SEQ. ID. No. 71). However, fragments of the HBcAg may also be encoded with the nucleic acid in certain embodiments. A fragment of the HBcAg sequence can comprise at least, equal to, greater than, or less than, or any number in between 3, 5, 10, 20, 50, 75, 100, 125, 150, or 175 consecutive amino acids of a natural or synthetic HBcAg polypeptide (e.g., a naturally occurring isotype or a codon-optimized or otherwise modified HBcAg polypeptide). FIGS. 1(*e-i*) illustrate several constructs encoding fragments of HBcAg that are between about 40 to about 60 amino acids in length.

Some embodiments include, for example, one or more of the HBcAg nucleic acid or protein sequences disclosed in International Patent Application Publication Number WO 20091130588, which designated the United States and was published in English, the disclosure of which is hereby expressly incorporated by reference in its entirety.

Meanwhile, the isolated nucleic acid encoding HBcAg may also be joined to an isolated nucleic acid encoding a heterologous protein. The heterologous protein may generally vary in the same manner discussed above with respect to the HBcAg. Thus, in some embodiments, the isolated nucleic acid sequences may encode native, variants or mutants of a heterologous protein, and these nucleic acids may also be codon-optimized (e.g., a codon-optimized nucleic acid encoding HCV NS3/4A from the human hepatitis virus in SEQ. ID. No. 2, a codon-optimized nucleic acid encoding NS5A from the human hepatitis virus in SEQ. ID. No. 8, codon-optimized nucleic acid encoding HBV HBcAg from the human hepatitis virus in SEQ. ID. No. 10, codon-optimized nucleic acid encoding HBV HBeAg from the human hepatitis virus in SEQ. ID. Nos. 12 and 14, codon-optimized nucleic acid encoding ovalbumin in SEQ. ID. No. 16, codon-optimized nucleic acid encoding birch antigen in SEQ. ID. No. 18). In some embodiments, the isolated nucleic acid encodes a fragment of the heterologous protein. In some embodiments, all of the vaccine sequences include a Kozak sequence (e.g., SEQ. ID. No. 106).

The heterologous protein, in some embodiments, can be an antigen, such as a plant antigen (e.g., birch antigen), viral antigen, or an animal antigen (e.g., ovalbumin antigen). The antigen may also be a hepatitis antigen, for example a hepatitis B virus (HBV) antigen or a hepatitis C virus (HCV) antigen. The HCV antigens can be from viruses known to infect animals of any species, including, but not limited to, amphibians, reptiles, birds—such as stork, and heron, mice, hamsters, rats, rabbits, guinea pigs, woodchucks, pigs, micro-pigs, goats, dogs, cats, humans and non-human primates (e.g., baboons, monkeys, and chimpanzees). Similarly, the HBV antigens can be from viruses known to infect animals of any species, including, but not limited to, amphibians, reptiles, birds—such as stork, and heron, mice, rodents, pigs, micro-pigs, goats, dogs, cats, humans and non-human primates (e.g., baboons, monkeys, and chimpanzees). In certain embodiments, the antigen is a HCV antigen selected from NS3/4A, NS5A, and combinations thereof. In certain embodiments, the antigen is a HBV antigen selected from a HBV surface antigen, HBV e antigen, human HBcAg, a human HBV polymerase antigen, a human HBV x antigen, and combinations thereof.

If the isolated nucleotide encodes a heterologous protein that is an HBV antigen, the heterologous protein can be substantially different than the HBcAg also encoded in the isolated nucleotide. As an example, the isolated nucleic acid may include a nucleic acid encoding HBcAg, which is joined to an isolated nucleic acid encoding a heterologous protein, where the heterologous protein is an HBV antigen that is non-naturally occurring or in a non-naturally occurring position with respect to the HBcAg. SEQ. ID. No. 54 is an exemplary nucleic acid that includes this feature because it encodes heron HBcAg joined to human HBcAg. Without being limited to any particular designation, the human HBcAg is an HBV antigen that is in a non-naturally occurring position with respect to the heron HBcAg. Conversely, the heron HBcAg may be designated as the HBV antigen that is in a non-naturally occurring position with respect to the human HBcAg.

Some embodiments have an isolated nucleic acid that encodes at least a stork or heron HBcAg antigen, or a fragment thereof, and human HBcAg, or a fragment thereof (e.g., SEQ. ID. No. 52 and 54). In certain embodiments, the isolated nucleic acid encodes at least stork or heron HBcAg antigen, or a fragment thereof, and human HBV e antigen, or a fragment thereof (e.g., SEQ. ID. 44 and 46).

Some embodiments include, for example, one or more heterologous proteins, or isolated nucleic acids encoding the same, in International Patent Application Publication Number WO 20091130588, which designated the United States and was published in English, the disclosure of which is hereby expressly incorporated by reference in its entirety. As an example, various HCV HS3/4A polypeptides, and fragments of HCV HS3/4A polypeptides, are disclosed within WO 20091130588 which may be included in the isolated nucleic acids.

Non-limiting examples of isolated nucleic acids encoding HBcAg, or a fragment thereof, joined to an isolated nucleic acid encoding a heterologous protein, include, but are not limited to: (1) stork HBcAg joined to HCV NS3/4A (e.g., SEQ. ID. No. 24 and 26); (2) heron HBcAg joined to HCV NS3/4A (e.g., SEQ. ID. No. 36); (3) stork HBcAg joined to HCV NS5A (e.g., SEQ. ID. No. 40); (4) heron HBcAg joined to HCV NS5A (e.g., SEQ. ID. No. 42); (5) stork HBcAg joined to human HBV e antigen (e.g., SEQ. ID. No. 44 and 46); (6) heron HBcAg joined to human HBV e antigen (e.g., SEQ. ID. No. 48 and 50); (7) stork HBcAg and human HBcAg (e.g., SEQ. ID. No. 52 and 103); (8) heron HBcAg joined to human HBcAg (e.g., SEQ. ID. No. 50 and 105); (9) stork HBcAg joined to birch antigen (e.g., SEQ. ID. No. 56); (10) heron HBcAg joined to birch antigen (e.g., SEQ. ID. No. 58); (11) stork HBcAg joined to ovalbumin antigen (e.g., SEQ. ID. No. 60); and (12) stork HBcAg joined to ovalbumin antigen (e.g., SEQ. ID. No. 62).

In some aspects, as discussed above, the isolated nucleic acid includes one or more NS3 protease cleavage sites, wherein the NS3 protease cleavage site is at a non-naturally occurring position. Examples of cleavage sites that may be included in the isolated nucleic acid include, but are not limited to, SEQ. ID. No. 4 and 6. In certain embodiments, the NS3 protease cleavage site is between the sequences encoding HBcAg and the heterologous protein. Thus, in some embodiments, the isolated nucleic acids encode a fusion protein, which may be cleaved by NS3 protease. In other aspects, the isolated nucleic acid encodes two or more fragments of HBcAg having a cleavage site between the two encoded fragments. Accordingly, the isolated nucleic acid encoding fragments of HBcAg, and therefore encodes a protein that is configured to be cleaved by NS3 protease to form HBcAg fragments.

Some embodiments of the isolated nucleic acid include an isolated nucleic acid encoding HBcAg, or a fragment thereof, joined to an isolated nucleic acid encoding heterologous protein, wherein the heterologous protein is HCV NS3/4A (e.g., SEQ. ID. No. 24). In certain embodiments, the isolated nucleic acid encodes an NS3 protease cleavage site between the isolated nucleic acid encoding HCV NS3/4A and the isolated nucleic acid encoding HBcAg (e.g., SEQ. ID. No. 30).

Embodiments of the isolated nucleic acid include HBcAg and a plurality of isolated nucleic acids encoding antigens, each of the isolated nucleic acids being joined together and having an HCV protease cleavage site in between. As an example, SEQ. ID. Nos. 64, 66, and 68 include NS3/4A antigen, NS5A antigen, and HBcAg antigen having an HCV protease cleavage site between each antigen.

Some embodiments of the isolated nucleic acids disclosed herein encode a fragment of human HBcAg between (i.e., joined at both ends to) fragments of avian HBcAg (e.g., stork or heron HBcAg). Thus, for example, the isolated nucleic acid may encode a polypeptide, where the polypeptide comprises, consists essentially of, or consists of avian HBcAg having a fragment of human HBcAg inserted into said avian HBcAg. In some aspects, the human HBcAg fragment is inserted into at least a portion, or all, of the spike region of the avian HBcAg (i.e., the region of HBcAg displayed on the surface the HBcAg capsid). Preferably, the human HBcAg is encoded into any, or all, of the amino acid positions 87 to 129 in the nucleic acid encoding avian HBcAg (e.g., codon-optimized stork HBcAg (e.g., SEQ. ID. No. 20) or codon-optimized heron HBcAg (e.g., SEQ. ID. No. 22)). In a preferred embodiment, the isolated nucleic acid encodes about a 43 amino acid fragment of human HBcAg inserted into amino acid positions of about 87 to about 129 of an avian HBcAg (e.g., an isolated nucleic acid that encodes codon-optimized stork HBcAg having 43 amino acid fragment of human HBcAg inserted at amino acid positions 87 to 129 (e.g., SEQ. ID. No. 103, which encodes the fusion protein in SEQ. ID. No. 102), or an isolated nucleic acid that encodes codon-optimized heron HBcAg having a 43 amino acid fragment of human HBcAg is inserted at amino acid positions 87 to 129 (e.g., SEQ. ID. No. 105, which encodes the fusion protein in SEQ. ID. No. 104)).

As would be appreciated by a person of ordinary skill, the proteins encoded in the isolated nucleic acids disclosed herein may be obtained using known methods. As an example, the nucleic acids may be inserted into an appropriate plasmid, which is subsequently inserted into to cells that express the protein. Other methods for obtaining the encoded proteins are also known. Accordingly, the scope of the present application includes the proteins that can be obtained from the isolated nucleic acids disclosed herein. For example, SEQ. ID. 23 describes a protein that can be obtained from the expression of SEQ. ID. 24. Thus, embodiments of the present invention also include, but are not limited to, proteins having the sequences in SEQ. ID. Nos. 23, 25, 27, 29, 31, 33, 35, 37, 39, 41, 43, 45, 47, 49, 51, 53, 55, 57, 59, 61, 63, 65, 67, 69, 70, 72, 74, 76, 78, 80, 82, 84, 86, 88, 102 and 104.

Immunogenic Compositions Comprising Nucleic Acids

Disclosed herein are immunogenic compositions relating to genetic constructs that include nucleic acids encoding HBcAg, or a fragment thereof, and nucleic acids encoding a heterologous protein. In some embodiments, both sequences are in the same nucleic acid construct (e.g., the same plasmid). In certain embodiments, both sequences are in separate nucleic acid constructs. Some embodiments of the immunogenic compositions described herein include any of the isolated nucleic acids discussed above, wherein a nucleic acid encoding HBcAg, or a fragment thereof, is joined to a nucleic acid encoding a heterologous protein. Some embodiments of the immunogenic compositions disclosed herein include one or proteins encoded by a nucleic acid described herein.

The source of the HBcAg that is encoded in the nucleic acid is not particularly limited. Accordingly, the nucleic acid contemplated for the immunogenic compositions described herein can be nucleic acids from viruses known to infect animals of any species, including but limited to, humans, mice, reptiles, birds (e.g., stork and heron), rodents, pigs, micro-pigs, goats, dogs, cats, and non-human primates (e.g., baboons, monkeys, and chimpanzees), as mentioned above. In some embodiments, the HBcAg is selected from a human hepatitis antigen, an avian hepatitis antigen, a stork hepatitis antigen, and a heron hepatitis antigen.

The sequences encoding HBcAg can generally be the same as those discussed above with respect to the isolated nucleic acids. Thus, in some embodiments, any of the nucleic acid sequences described above that include HBcAg may be used in the immunogenic composition. As an example, the isolated nucleic acid may include native (e.g., SEQ. ID. No. 71) or variant HBcAg or mutant HBcAg, and the nucleic acid may also be codon-optimized (e.g., SEQ. ID. No. 22). In some embodiments, the isolated nucleic acid encodes a fragment of HBcAg, as described above with respect to the isolated nucleic acids. For example, fragment of the HBcAg sequence can comprise at least, equal to, greater than, or less than, or any number in between 3, 5, 10, 20, 50, 75, 100, 125, 150, or 175 consecutive amino acids of a natural or synthetic HBcAg polypeptide. A full-length HBcAg can also be encoded in an isolated nucleic acid included within the immunogenic composition.

Some embodiments include nucleic acids that have homology or sequence identity to any one of the nucleic acid sequences disclosed herein (e.g. SEQ. ID. Nos. 24, 26, 28, 30, 32, 34, 36, 38, 40, 42, 44, 46, 48, 50, 52, 54, 56, 58, 60, 62, 64, 66, 68, 70, 102, 104 etc.). In some embodiments, said homologous nucleic acids generate, enhance, or improve an immune response, as defined above. Several techniques exist to determine nucleic acid or protein sequence homology. Thus, embodiments of the nucleic acids can have from 70% homology or sequence identity to 100% homology or sequence identity to any one of the nucleic acid sequences or protein sequences disclosed herein. That is, embodiments can have at least, equal to or any number between about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology or sequence identity to any one of the polypeptide or nucleic acid sequences disclosed herein.

Several homology or sequence identity searching programs based on nucleic acid sequences are known in the art and can be used to identify molecules that are homologous. In one approach, a percent sequence identity can be determined by standard methods that are commonly used to compare the similarity and position of the base pairs of two nucleic acids. Using a computer program such as BLAST or FASTA, two sequences can be aligned for optimal matching of their respective base pairs (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program.

Some embodiments included isolated nucleic acids having sufficient homology or sequence identity to any one of the nucleic acid sequences disclosed herein such that hybridization will occur between the isolated nucleic acid and any one of the nucleic acids sequences disclosed herein. In some aspects, hybridization occurs under usual washing conditions in Southern hybridization, that is, at a salt concentration corresponding to 0.1 times saline sodium citrate (SSC) and 0.1% SDS at 37° C. (low stringency), preferably 0.1 times SSC and 0.1% SDS at 60° C. (medium stringency), and more preferably 0.1 times SSC and 0.1% SDS at 65° C. (high stringency). In certain aspects, the nucleic acid embodiments have a percentage of consecutive bases that hybridize under stringent conditions with any one of the nucleic acids sequences disclosed herein, where the number of consecutive bases is at least 40.0%, 41.0%, 42.0%, 43.0%, 44.0%, 45.0%, 46.0%, 47.0%, 48.0%, 49.0%, 50.0%, 51.0%, 52.0%, 53.0%, 54.0%,. 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% of the total number of bases in the nucleic acid sequence.

Some embodiments of the immunogenic composition include a nucleic acid encoding a heterologous protein. The heterologous protein encoded by the nucleic acid, in some embodiments, can be an antigen, such as a plant antigen (e.g., birch antigen), viral antigen, or an animal antigen (e.g., ovalbumin antigen). The antigen may also be a hepatitis antigen, for example a hepatitis B virus (HBV) antigen or a hepatitis C virus (HCV) antigen. The HCV antigens can be from viruses known to infect animals of any species, including, but not limited to, amphibians, reptiles, birds (e.g., stork and heron) mice, hamsters, rats, rabbits, guinea pigs, woodchucks, pigs, micro-pigs, goats, dogs, cats, humans and non-human primates (e.g., baboons, monkeys, and chimpanzees). Similarly, the HBV antigens can be from viruses known to infect animals of any species, including, but not limited to, amphibians, reptiles, birds (e.g., stork and heron), and heron, mice, hamsters, rodents, pigs, micro-pigs, goats, dogs, cats, humans and non-human primates (e.g., baboons, monkeys, and chimpanzees). In certain embodiments, the antigen is a HCV antigen selected from NS3/4A, NS5A, and combinations thereof. In certain embodiments, the antigen is a HBV antigen selected from a HBV surface antigen, HBV e antigen, human HBcAg, a human HBV polymerase antigen, a human HBV x antigen, and combinations thereof.

Non-limiting examples of nucleic acids encoding heterologous proteins that may be included within the immunogenic composition include HCV NS3/4A (e.g., SEQ. ID. 2), HCV NS5A (e.g., SEQ. ID. 8), HBcAg (e.g., SEQ. ID. 10), HBV e antigen (e.g., SEQ. ID. 12 and 14), and ovalbumin (e.g., SEQ. ID. 16).

If the immunogenic composition includes an encoded heterologous protein that is an HBV antigen, the heterologous protein or nucleic acid encoding the heterologous protein can be substantially different than the HBcAg present in the immunogenic composition. As example, the immunogenic composition may include a nucleic acid encoding HBcAg, and a nucleic acid encoding a heterologous protein, which is an HBV antigen that is non-naturally occurring or in a non-naturally occurring position with respect to the HBcAg. The immunogenic composition may include, for example, a mixture of SEQ. ID. No. 10 and 22, and therefore includes two nucleic acids encoding substantially different HBV antigens (i.e., human HBcAg and heron HBcAg).

Non-limiting examples of mixtures of nucleic acid sequences encoding HBcAg, or a fragment thereof, and nucleic acid sequences encoding a heterologous protein, that may be included in the immunogenic compositions, include, but are not limited to, nucleic acid sequences encoding: (1) stork HBcAg and HCV NS3/4A (e.g., SEQ. ID. Nos. 20 and 2); (2) heron HBcAg and HCV NS3/4A (e.g., SEQ. ID. Nos. 22 and 2); (3) stork HBcAg and HCV NS5A (e.g., SEQ. ID. Nos. 20 and 8); (4) heron HBcAg and HCV NS5A (e.g., SEQ. ID. Nos. 22 and 8); (5) stork HBcAg and human HBV e antigen (e.g., SEQ. ID. Nos. 20 and 12); (6) heron HBcAg and human HBV e antigen (e.g., SEQ. ID. Nos. 22 and 12); (7) stork HBcAg and human HBcAg (e.g., SEQ. ID. Nos. 20 and 10); (8) heron HBcAg and human HBcAg (e.g., SEQ. ID. Nos. 22 and 10); (9) stork HBcAg and birch antigen (e.g., SEQ. ID. Nos. 20 and 18); (10) heron HBcAg and birch antigen (e.g., SEQ. ID. Nos. 22 and 18); (11) stork HBcAg and ovalbumin antigen (e.g., SEQ. ID. Nos. 20 and 16); and (12) stork HBcAg and ovalbumin antigen (e.g., SEQ. ID. Nos. 22 and 16).

Some embodiments of the immunogenic composition include the isolated nucleic acids described above, wherein the nucleic acid encoding HBcAg, or a fragment thereof, is joined to nucleic acid sequences encoding a heterologous protein. Accordingly, further exemplary compositions may include a nucleic acid encoding: (1) stork HBcAg joined to HCV NS3/4A (e.g., SEQ. ID. No. 24 and 26); (2) heron HBcAg joined to HCV NS3/4A (e.g., SEQ. ID. No. 36); (3) stork HBcAg joined to HCV NS5A (e.g., SEQ. ID. No. 40); (4) heron HBcAg joined to HCV NS5A (e.g., SEQ. ID. No. 42); (5) stork HBcAg joined to human HBV e antigen (e.g., SEQ. ID. No. 44 and 46); (6) heron HBcAg joined to human HBV e antigen (e.g., SEQ. ID. No. 48 and 50); (7) stork HBcAg joined to human HBcAg (e.g., SEQ. ID. No. 52 and 103); (8) heron HBcAg joined to human HBcAg (e.g., SEQ. ID. No. 50 and 105); (9) stork HBcAg joined to birch antigen (e.g., SEQ. ID. No. 56); (10) heron HBcAg joined to birch antigen (e.g., SEQ. ID. No. 58); (11) stork HBcAg joined to ovalbumin antigen (e.g., SEQ. ID. No. 60); and (12) stork HBcAg joined to ovalbumin antigen (e.g., SEQ. ID. No. 62).

It is contemplated that various other compounds may be included in one or more of the compositions. Some embodiments of the composition may further include an additional adjuvant. Non-limiting example of adjuvants that can be included are: interleukin-2 (IL2), interleukin-12 (IL12), interleukin-15 (IL15), interleukin-21 (IL21), interleukin-28b (IL28b), galactosyl transferase, a toll-like receptor (TLR), ribavirin, alum, CpGs, or an oil. In some embodiments, the composition includes an isolated nucleic acid, or constructs comprising said nucleic acids, encoding a protein that is an adjuvant, such as IL2, IL12, IL15, IL21, IL28b, galactose transferase, a TLR, and the like. In certain aspects, the isolated nucleic acid encoding the protein which is an adjuvant may be in the same construct encoding HBcAg and/or the heterologous protein. In other aspects, the isolated nucleic acid encoding the protein, which is an adjuvant may be in a different construct than the construct encoding HBcAg and/or the heterologous protein.

The compositions described herein may also contain other ingredients or compounds in addition to nucleic acids and/or polypeptides, including, but not limited to, various other peptides, adjuvants, binding agents, excipients such as stabilizers (to promote long term storage), emulsifiers, thickening agents, salts, preservatives, solvents, dispersion media, coatings, antibacterial and antifungal agents, isotonic and absorption delaying agents and the like. See e.g., U.S. application Ser. No. 09/929,955 and U.S. application Ser. No. 09/930,591. These compositions are suitable for treatment of animals, particularly mammals, either as a preventive measure to avoid a disease or condition or as a therapeutic to treat animals already afflicted with a disease or condition.

Many other ingredients may also be present in the compositions provided herein. For example, the adjuvant and antigen can be employed in admixture with conventional excipients (e.g., pharmaceutically acceptable organic or inorganic carrier substances suitable for parenteral, enteral (e.g., oral) or topical application that do not deleteriously react with the therapeutic ingredients (e.g., construct encoding HBcAg). Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable carriers are described in Remmington's Pharmaceutical Sciences, 15th Edition, Easton:Mack Publishing Company, pages 1405-1412 and 1461-1487 (1975) and The National Formulary XIV, 14th Edition, Washington, American Pharmaceutical Association (1975).

Immunogenic Compositions Comprising Polypeptides

Some of the embodiments described herein concern compositions that comprise, consist essentially of, or consist of polypeptides encoded by any of the nucleic acids disclosed herein. In some embodiments, the composition includes an admixture of HBcAg, or a fragment thereof, and a heterologous protein. In certain aspects, the composition includes a protein having HBcAg joined to a heterologous protein.

The HBcAg polypeptides that may be included in the immunogenic compositions can be any HBcAg polypeptide that can be encoded in the nucleic acids within the immunogenic composition of nucleic acids discussed above, or those encoded in the isolated nucleic acids discussed above. Thus, in some embodiments, the HBcAg is derived from a codon-optimized nucleic acid (e.g., SEQ. ID. No. 21 is derived from SEQ. ID. No. 22). The HBcAg may also be a native or variant form of the protein. Also, the composition may include a fragment of HBcAg. A fragment of HBcAg can comprise at least, equal to, greater than, or less than, or any number in between 3, 5, 10, 20, 50, 75, 100, 125, 150, or 175 consecutive amino acids of a natural or synthetic HBcAg polypeptide (e.g., a naturally occurring isotype or a codon-optimized or otherwise modified HBcAg polypeptide).

Some embodiments include polypeptides that have homology or sequence identity to any one of the polypeptide sequences disclosed herein (e.g. SEQ. ID. Nos. 23, 25, 27, 29, 31, 33, 35, 37, 39, 41, 43, 45, 47, 49, 51, 53, 55, 57, 59, 61, 63, 65, 67, 69, 70, 102, 104, etc.). In some embodiments, said polypeptides generate, enhance, or improve an immune response, as defined above. Several techniques exist to determine protein sequence homology or sequence identity. Thus, embodiments of the polypeptides can have from 70% homology to 100% homology or sequence identity to any one of the polypeptides disclosed herein. That is, embodiments can have at least, equal to, or any number in between about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology or sequence identity to any one of the polypeptide or nucleic acid sequences disclosed herein.

Several homology or sequence identity searching programs based on polypeptide sequences are known in the art and can be used to identify molecules that are homologous. In one approach, a percent sequence identity can be determined by standard methods that are commonly used to compare the similarity and position of the amino acids of two polypeptides. Using a computer program such as BLAST or FASTA, two sequences can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program.

Similarly, the heterologous protein that may be included in the immunogenic compositions can be any heterologous protein that can be encoded in the nucleic acids within the immunogenic composition of nucleic acids discussed above, or those encoded in the isolated nucleic acids discussed above. Thus, in some embodiments, the heterologous protein is derived from a codon-optimized nucleic acid (e.g., SEQ. ID. No. 7 is derived from SEQ. ID. No. 8). The HBcAg may also be a native or variant form of the protein.

If the immunogenic composition includes a heterologous protein that is an HBV antigen, the heterologous protein can be substantially different than the HBcAg present in the immunogenic composition. As example, the immunogenic composition may include HBcAg, and a heterologous protein which is an HBV antigen that is non-naturally occurring or in a non-naturally occurring position with respect to the HBcAg. The immunogenic composition may include, for example, a mixture of SEQ. ID. No. 9 and 11, and therefore includes different HBV antigens (i.e., human HBcAg and heron HBcAg).

Non-limiting examples of admixtures of HBcAg, or a fragment thereof, and a heterologous protein, which may be included in the immunogenic compositions, include, but are not limited to: (1) stork HBcAg and HCV NS3/4A (e.g., SEQ. ID. Nos. 19 and 1); (2) heron HBcAg and HCV NS3/4A (e.g., SEQ. ID. Nos. 21 and 1); (3) stork HBcAg and HCV NS5A (e.g., SEQ. ID. Nos. 19 and 7); (4) heron HBcAg and HCV NS5A (e.g., SEQ. ID. Nos. 21 and 7); (5) stork HBcAg and human HBV e antigen (e.g., SEQ. ID. Nos. 19 and 11); (6) heron HBcAg and human HBV e antigen (e.g., SEQ. ID. Nos. 21 and 11); (7) stork HBcAg and human HBcAg (e.g., SEQ. ID. Nos. 19 and 9); (8) heron HBcAg and human HBcAg (e.g., SEQ. ID. Nos. 21 and 9); (9) stork HBcAg and birch antigen (e.g., SEQ. ID. Nos. 19 and 17); (10) heron HBcAg and birch antigen (e.g., SEQ. ID. Nos. 21 and 17); (11) stork HBcAg and ovalbumin antigen (e.g., SEQ. ID. Nos. 19 and 15); and (12) stork HBcAg and ovalbumin antigen (e.g., SEQ. ID. Nos. 21 and 15).

It is also contemplated that some immunogenic compositions can comprise both a protein as described herein and a nucleic acid as described herein. For example, some embodiments may include a nucleic acid encoding an HBcAg (e.g., a nucleic acid encoding a stork or heron HBcAg (e.g., SEQ. ID. No. 20 and 22) and a protein that is an antigen (e.g., HCV NS3/4A SEQ. ID. No. 1). Alternatively, some embodiments are immunogenic compositions that comprise an HBcAg protein (e.g., stork or heron HBcAg SEQ. ID. No. 19 and 21) and a nucleic acid encoding an antigen (e.g., a nucleic acid encoding HCV NS3/4A SEQ. ID. No. 2).

It is also contemplated that various other ingredients may be included to improve the immunogenic composition by, for example, increasing the immune response caused by the composition. Some embodiments of the composition may further include an adjuvant. Non-limiting example of adjuvants include interleukin-2 (IL2), interleukin-12 (IL12), interleukin-15 (IL15), interleukin-21 (IL21), interleukin-28b (IL28b), galactosyl transferase, a toll-like receptor (TLR), ribavirin, alum, CpGs, and an oil.

Various ingredients, such as excipients, adjuvants, binding agents, etc., may be included in the immunogenic compositions including a polypeptide. The same ingredients as those disclose above with respect to immunogenic compositions of isolated nucleic acids may be utilized.

Methods of Enhancing or Promoting an Immune Response

Methods of enhancing or promoting an immune response in an animal, including humans, to an antigen are also provided. Such methods can be practiced, for example, by identifying an animal in need of an immune response and administering said animal with any of the immunogenic compositions described above that is effective to enhance or facilitate an immune response to the heterologous protein. In some embodiments, compositions including one or more isolated nucleic acids encoding the HBcAg antigen, or a fragment thereof, and a nucleic acid encoding a heterologous protein are administered to a animal in need thereof at the same time in the same mixture. In certain embodiments, compositions of HBcAg antigen, or a fragment thereof, and a heterologous protein are administered to the animal at the same time in the same mixture. Alternatively, the nucleic acid encoding the HBcAg and the nucleic acid encoding the heterologous protein are coadministered. Similarly, the HBcAg protein and the protein antigen can be coadministered. By coadministered, it is mean that the two nucleic acids or two protein are provided at the same time in the same mixture or within at least, equal to, or about any number in between 1, 5, 10, 15, 20, 30, 40, 50, or 60 minutes each separate administration. However, the present invention is not limited to any particular order of administration.

Accordingly, some methods include administering a composition comprising an isolated nucleic acid encoding HBcAg, or a fragment thereof, joined to an isolated nucleic acid encoding a heterologous protein. Non-limiting examples of compositions that may be administered according to the methods disclosed herein include, but are not limited t nucleic acids encoding: (1) stork HBcAg joined to HCV NS3/4A (e.g., SEQ. ID. No. 24 and 26); (2) heron HBcAg joined to HCV NS3/4A (e.g., SEQ. ID. No. 36); (3) stork HBcAg joined to HCV NS5A (e.g., SEQ. ID. No. 40); (4) heron HBcAg joined to HCV NS5A (e.g., SEQ. ID. No. 42); (5) stork HBcAg joined to human HBV e antigen (e.g., SEQ. ID. No. 44 and 46); (6) heron HBcAg joined to human HBV e antigen (e.g., SEQ. ID. No. 48 and 50); (7) stork HBcAg and human HBcAg (e.g., SEQ. ID. No. 52 and 103); (8) heron HBcAg joined to human HBcAg (e.g., SEQ. ID. No. 50 and 105); (9) stork HBcAg joined to birch antigen (e.g., SEQ. ID. No. 56); (10) heron HBcAg joined to birch antigen (e.g., SEQ. ID. No. 58); (11) stork HBcAg joined to ovalbumin antigen (e.g., SEQ. ID. No. 60); and (12) stork HBcAg joined to ovalbumin antigen (e.g., SEQ. ID. No. 62).

Furthermore, compositions including nucleic acid sequences encoding HBcAg, or a fragment thereof, and nucleic acid sequences encoding a heterologous protein in Trans, may be administered according to the methods disclosed herein. Non-limiting examples of compositions for administering according to the methods disclosed herein, include, but are not limited to nucleic acids encoding: (1)

stork HBcAg and HCV NS3/4A (e.g., SEQ. ID. Nos. 20 and 2); (2) heron HBcAg and HCV NS3/4A (e.g., SEQ. ID. Nos. 22 and 2); (3) stork HBcAg and HCV NS5A (e.g., SEQ. ID. Nos. 20 and 8); (4) heron HBcAg and HCV NS5A (e.g., SEQ. ID. Nos. 22 and 8); (5) stork HBcAg and human HBV e antigen (e.g., SEQ. ID. Nos. 20 and 12); (6) heron HBcAg and human HBV e antigen (e.g., SEQ. ID. Nos. 22 and 12); (7) stork HBcAg and human HBcAg (e.g., SEQ. ID. Nos. 20 and 10); (8) heron HBcAg and human HBcAg (e.g., SEQ. ID. Nos. 22 and 10); (9) stork HBcAg and birch antigen (e.g., SEQ. ID. Nos. 20 and 18); (10) heron HBcAg and birch antigen (e.g., SEQ. ID. Nos. 22 and 18); (11) stork HBcAg and ovalbumin antigen (e.g., SEQ. ID. Nos. 20 and 16); and (12) stork HBcAg and ovalbumin antigen (e.g., SEQ. ID. Nos. 22 and 16).

In addition, compositions including HBcAg, or a fragment thereof, and a heterologous protein, may be administered according to the methods disclosed herein. Non-limiting examples of the compositions for administering according to the methods disclosed herein, include, but are not limited to: (1) stork HBcAg and HCV NS3/4A (e.g., SEQ. ID. Nos. 19 and 1); (2) heron HBcAg and HCV NS3/4A (e.g., SEQ. ID. Nos. 21 and 1); (3) stork HBcAg and HCV NS5A (e.g., SEQ. ID. Nos. 19 and 7); (4) heron HBcAg and HCV NS5A (e.g., SEQ. ID. Nos. 21 and 7); (5) stork HBcAg and human HBV e antigen (e.g., SEQ. ID. Nos. 19 and 11); (6) heron HBcAg and human HBV e antigen (e.g., SEQ. ID. Nos. 21 and 11); (7) stork HBcAg and human HBcAg (e.g., SEQ. ID. Nos. 19 and 9); (8) heron HBcAg and human HBcAg (e.g., SEQ. ID. Nos. 21 and 9); (9) stork HBcAg and birch antigen (e.g., SEQ. ID. Nos. 19 and 17); (10) heron HBcAg and birch antigen (e.g., SEQ. ID. Nos. 21 and 17); (11) stork HBcAg and ovalbumin antigen (e.g., SEQ. ID. Nos. 19 and 15); and (12) stork HBcAg and ovalbumin antigen (e.g., SEQ. ID. Nos. 21 and 15).

Other embodiments concern methods of inhibiting HCV infection, reducing HCV viral titer, inhibiting HCV replication, treating HCV infection or promoting an immune response specific for an HCV protein. By one approach, an immunogenic composition comprising an isolated nucleic acid encoding HBcAg, or a fragment thereof (e.g., a human codon-optimized nucleic acid encoding a HBcAg derived from an avian hepatitis, such as a hepatitis that infects stork (e.g., SEQ. ID. No. 20) or heron (e.g., SEQ. ID. No. 22)) and an isolated nucleic acid encoding an HCV antigen described herein (e.g., a human codon-optimized nucleic acid encoding NS3, NS3/4A (e.g., SEQ. ID. No. 2), and/or NS5A (e.g., SEQ. ID. 8) are used to prepare a medicament for the inhibition of HCV infection, the reduction of HCV viral titer, the inhibition of HCV replication, the treatment of HCV infection or for the generation of an immune response to an HCV protein. That is, preferred compositions comprise, consist essentially of, or consist of a nucleic acid encoding HBcAg derived from an avian hepatitis (e.g., SEQ. ID. Nos. 20 and 22) and a nucleic acid encoding an HCV protein derived from a hepatitis virus that infects humans (e.g., SEQ. ID. No. 2). The nucleic acids present in said compositions can be in Cis (e.g., operably joined in frame) or in Trans (e.g., on separate expression constructs altogether). By one approach, an individual in need of a medicament that inhibits HCV infection, reduces HCV viral titer, inhibits HCV replication, treats HCV infection or that promotes an immune response to an HCV protein is identified and said individual is provided a medicament comprising a nucleic acid encoding an HBcAg antigen (e.g., SEQ. ID. Nos. 20 and 22) and a nucleic acid encoding an HCV antigen, such as codon-optimized NS3/4A (e.g., SEQ. ID. NO.: 1), or codon-optimized NS5A (e.g., SEQ. ID. No. 8).

Alternatively, an immunogenic composition comprising an HBcAg polypeptide (e.g., SEQ. ID. Nos. 21 and 23), or a fragment thereof, and an HCV antigen described herein (e.g., codon-optimized NS3/4A in SEQ. ID. No. 1) are used to prepare a medicament for the inhibition of HCV infection, the reduction of HCV viral titer, the inhibition of HCV replication, the treatment of HCV infection or for the generation of an immune response to an HCV protein.

Some embodiments concern methods of inhibiting HBV infection, reducing HBV viral titer, inhibiting HBV replication, treating HBV infection or promoting an immune response specific for an HBV protein. By one approach, an immunogenic composition comprising a nucleic acid encoding HBcAg (e.g., a human codon-optimized nucleic acid encoding a HBcAg derived from an avian hepatitis, such as a hepatitis that infects stork (e.g., SEQ. ID. No. 20) or heron (e.g., SEQ. ID. No. 22)) and an isolated nucleic acid encoding an HBV antigen described herein (e.g., a human codon-optimized nucleic acid encoding a HBcAg (e.g., SEQ. ID. No. 10), a HBV surface antigen, a HBV e antigen (e.g., SEQ. ID. Nos. 12 and 14), a HBV polymerase antigen, or a HBV x antigen derived from a hepatitis that infects humans) are used to prepare a medicament for the inhibition of HBV infection, the reduction of HBV viral titer, the inhibition of HBV replication, the treatment of HBV infection or for the generation of an immune response to an HBV protein. That is, preferred compositions comprise, consist essentially of, or consist of an HBcAg derived from an avian hepatitis and a nucleic acid encoding an HBV protein derived from a hepatitis virus that infects humans. The nucleic acids present in said compositions can be in Cis (e.g., operably joined in frame) or in Trans (e.g., on separate expression constructs altogether). By one approach, an individual in need of a medicament that inhibits HBV infection, reduces HBV viral titer, inhibits HBV replication, treats HBV infection or that promotes an immune response to an HBV protein is identified and said individual is provided a medicament comprising a nucleic acid encoding an avian HBcAg (e.g., SEQ. ID. No. 20 and 22) and an HBV antigen, such as codon-optimized HBV antigen (e.g., codon-optimized HBeAg (e.g., SEQ. ID. NO.: 11)).

Alternatively, an immunogenic composition comprising an HBcAg polypeptide, or a fragment thereof, and an HBV antigen described herein are used to prepare a medicament for the inhibition of HBV infection, the reduction of HBV viral titer, the inhibition of HBV replication, the treatment of HBV infection or for the generation of an immune response to an HBV protein.

Some embodiments concern methods of ameliorating a birch allergy, reducing sensitivity to a birch allergen, or reducing IgE antibody levels specific to birch. By one approach, an immunogenic composition comprising a nucleic acid encoding HBcAg (e.g., a human codon-optimized nucleic acid encoding a HBcAg derived from an avian hepatitis, such as a hepatitis that infects stork (e.g., SEQ. ID. No. 20) or heron (e.g., SEQ. ID. No. 22)) and an isolated nucleic acid encoding a birch antigen (e.g., SEQ. ID. No 18) are used to prepare a medicament for the ameliorating a birch allergy, reducing sensitivity to a birch allergy, or reducing IgE antibody levels specific to birch. That is, preferred compositions comprise, consist essentially of, or consist of an HBcAg derived from an avian hepatitis and a nucleic acid encoding an birch antigen derived. The nucleic acids present in said compositions can be in Cis (e.g., operably joined in frame) or in Trans (e.g., on separate expression constructs altogether). By one approach, an individual in need of a medicament that ameliorates a birch allergy, reduces sensitivity to a birch allergen, or reduces IgE antibody levels specific to birch is identified and said individual is provided a medicament comprising a nucleic acid encoding an avian HBcAg (e.g., SEQ. ID. No. 20 and 22) and a birch antigen, such as codon-optimized birch antigen (e.g., SEQ. ID. NO.: 18).

Alternatively, an immunogenic composition comprising an HBcAg polypeptide, or a fragment thereof, and an birch antigen described herein are used to prepare a medicament for ameliorating a birch allergy, reducing sensitivity to a birch allergen, or reducing IgE antibody levels specific to birch antigen.

The effective dose and method of administration of a particular formulation can vary based on the individual patient and the type and stage of the disease, as well as other factors known to those of skill in the art. Therapeutic efficacy and toxicity can be determined by standard pharmaceutical procedures in cell cultures or experimental animals, e.g., ED50 (the dose therapeutically effective in 50% of the population). The data obtained from cell culture assays and animal studies can be used to formulate a range of dosage for human use. The dosage lies preferably within a range of circulating concentrations that include the ED50 with no toxicity. The dosage varies within this range depending upon the type of adjuvant derivative and antigen, the dosage form employed, the sensitivity of the patient, and the route of administration.

In certain embodiments an adjuvant is included within the administered composition. For instance, a pharmacologic agent can be added to a composition described herein as needed to increase or aid its effect. In another example, an immunological agent that increases the antigenic response can be utilized with a device described herein. For instance, U.S. Pat. No. 6,680,059 (which is hereby incorporated in its entirety by reference) describes the use of vaccines containing ribavirin as an adjuvant to the vaccine. However, an adjuvant may refer to any material that has the ability to enhance or facilitate an immune response or to increase or aid the effect of a therapeutic agent. Non-limiting example of adjuvants include interleukin-2 (IL2), interleukin-12 (IL12), interleukin-15 (IL15), interleukin-21 (IL21), interleukin-28b (IL28b), galactosyl transferase, a toll-like receptor (TLR), ribavirin, alum, CpGs, and an oil. Also, as described above, in some embodiments, the composition includes an isolated nucleic acid, or constructs comprising said nucleic acids, encoding a protein that is an adjuvant, such as IL2, IL12, IL15, IL21, IL28b, galactosyl transferase, a TLR, and the like. In certain aspects, the isolated nucleic acid encoding the protein which is an adjuvant may be in the same construct encoding HBcAg and/or the heterologous protein. In some aspects, methods of administering the immunogenic composition comprise administering an adjuvant before administering the immunogenic composition.

In some embodiments, the method includes administering an immunogenic composition that comprises an isolated nucleic that encodes HBcAg, or a fragment thereof, and separately administering an isolated nucleic acid that encodes a heterologous protein (e.g., SEQ. ID. No. 8). When the isolated nucleic acid encoding HBcAg and the isolated nucleic acid encoding the heterologous protein are administered separately, the isolated nucleic acid encoding HBcAg may, in some embodiments, may be administered before the isolated nucleic acid encoding heterologous protein. Alternatively, the isolated nucleic acid encoding heterologous protein may, in some embodiments, be administered before the isolated nucleic acid encoding HBcAg.

Other embodiments of the methods disclosed herein include administering a composition including both HBcAg and the heterologous protein. In some embodiments, the method includes administering an immunogenic composition that includes an admixture of an isolated nucleic acid encoding HBcAg and an isolated nucleic acid encoding the heterologous protein. In certain embodiments, the method includes administering an immunogenic composition that includes an admixture of an isolated nucleic acid encoding the HBcAg and an isolated nucleic acid encoding the heterologous protein.

Various routes of administration may be used for the methods described herein. In some embodiments, the immunogenic composition is administered parenterally (e.g., intramuscularly, intraperitoneally, subcutaneously, or intravenously to a mammal subject). In a preferred embodiment, the immunogenic compositions are administered intramuscularly, dermally, or subcutaneously. The methods may also include applying electrical stimulation, which can enhance the administration of the immunogenic compositions. As an example, electroporation may be included in the present methods disclosed herein. Electroporation includes applying electrical stimulation to improve the permeability of cells to the administered composition. Examples of electroporation techniques are disclosed in U.S. Pat. Nos. 6,610,044 and 5,273,525, the disclosures of both of these references are hereby incorporated by reference in their entireties.

The concentration of the nucleic acid or protein in the immunogenic composition to be administered can vary from about 0.1 ng/ml to about 50 mg/ml. In some aspects, the concentration of the immunogenic composition administered (e.g., a suitable dose of nucleic acid or protein for administration) is between about 10 ng/ml to 25 mg/ml. In still other aspects, the concentration is between 100 ng/ml to 10 mg/ml. In some aspects, the suitable dose of nucleic acid or protein for administration is greater than or equal to or less than about 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 21 μg/ml, 22 μg/ml, 23 μg/ml, 24 μg/ml, 25 μg/ml, 26 μg/ml, 27 μg/ml, 28 μg/ml, 29 μg/ml, 30 μg/ml, 31 μg/ml, 32 μg/ml, 33 μg/ml, 34 μg/ml, 35 μg/ml, 36 μg/ml, 37 μg/ml, 38 μg/ml, 39 μg/ml, 40 μg/ml, 41 μg/ml, 42 μg/ml, 43 μg/ml, 44 μg/ml, 45 μg/ml, 46 μg/ml, 47 μg/ml, 48 μg/ml, 49 μg/ml, 50 μg/ml, 55 μg/ml, 60 μg/ml, 65 μg/ml, 70 μg/ml, 75 μg/ml, 80 μg/ml, 85 μg/ml, 90 μg/ml, 95 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml, 800 μg/ml, 850 μg/ml, 900 μg/ml, 950 μg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, 5.1 mg/ml, 5.2 mg/ml, 5.3 mg/ml, 5.4 mg/ml, 5.5 mg/ml, 5.6 mg/ml, 5.7 mg/ml, 5.8 mg/ml, 5.9 mg/ml, 6.0 mg/ml, 6.1 mg/ml, 6.2 mg/ml, 6.3 mg/ml, 6.4 mg/ml, 6.5 mg/ml, 6.6 mg/ml, 6.7 mg/ml, 6.8 mg/ml, 6.9 mg/ml, 7.0 mg/ml, 7.1 mg/ml, 7.2 mg/ml, 7.3 mg/ml, 7.4 mg/ml, 7.5 mg/ml, 7.6 mg/ml, 7.7 mg/ml, 7.8 mg/ml, 7.9 mg/ml, 8.0 mg/ml, 8.1 mg/ml, 8.2 mg/ml, 8.3 mg/ml, 8.4 mg/ml, 8.5 mg/ml, 8.6 mg/ml, 8.7 mg/ml, 8.8 mg/ml, 8.9 mg/ml, 9.0 mg/ml, 9.1 mg/ml, 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, or within a range defined by, and including, any two of these values.

The amount of nucleic acid or protein administered using the methods described herein can vary from about 1 ng to 10g. In some aspects, the amount of nucleic acid or protein contained administered is less than greater than or equal to about 1 ng, 5 ng, 10 ng, 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 500 ng, 600 ng, 700 ng, 800 ng, 900 ng, 1 μg, 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 μg, 475 μg, 480 μg, 485 μg, 490 μg, 495 μg, 500 μg, 505 μg, 510 μg, 515 μg, 520 μg, 525 μg, 530 μg, 535 μg, 540 μg, 545 μg, 550 μg, 555 μg, 560 μg, 565 μg, 570 μg, 575 μg, 580 μg, 585 μg, 590 μg, 595 μg, 600 μg, 605 μg, 610 μg, 615 μg, 620 μg, 625 μg, 630 μg, 635 μg, 640 μg, 645 μg, 650 μg, 655 μg, 660 μg, 665 μg, 670 μg, 675 μg, 680 μg, 685 μg, 690 μg, 695 μg, 700 μg, 705 μg, 710 μg, 715 μg, 720 μg, 725 μg, 730 μg, 735 μg, 740 μg, 745 μg 750 μg, 755 μg, 760 μg, 765 μg, 770 μg, 775 μg, 780 μg, 785 μg, 790 μg, 795 μg, 800 μg, 805 μg, 810 μg, 815 μg, 820 μg, 825 μg, 830 μg, 835 μg, 840 μg, 845 μg, 850 μg, 855 μg, 860 μg, 865 μg, 870 μg, 875 μg, 880 μg, 885 μg, 890 μg, 895 μg, 900 μg, 905 μg, 910 μg, 915 μg, 920 μg, 925 μg, 930 μg, 935 μg, 940 μg, 945 μg, 950 μg, 955 μg, 960 μg, 965 μg, 970 μg, 975 μg, 980 μg, 985 μg, 990 μg, 995 μg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 2 g, 3 g, 4 g, 5 g, 6 g, 7 g, 8 g, 9 g, 10 g or within a range defined by, and including, any two of these values.

The following examples are given to illustrate various embodiments of the present invention in the field of DNA immunization, which can be delivered to a subject in need of an immune response to the antigen contained therein. It is to be understood that the following examples are not comprehensive or exhaustive of the many types of embodiments which can be prepared in accordance with the present invention.

EXAMPLE 1

The NS3/4A sequence was amplified from the serum of an HCV-infected patient (HCV genotype la) using the Polymerase Chain Reaction (PCR). Total RNA was extracted from serum, and cDNA synthesis and PCR were performed according to standard protocols (Chen M et al., *J. Med. Virol.* 43:223-226 (1995)). The cDNA synthesis was initiated using the antisense primer "NS4KR" (5'-CCG TCT AGA TCA GCA CTC TTC CAT TTC ATC-3' (SEQ. ID. NO. 98)). From this cDNA, a 2079 base pair DNA fragment of HCV, corresponding to amino acids 1007 to 1711, which encompasses the NS3 and NS4A genes, was amplified. A high fidelity polymerase (Expand High Fidelity PCR, Boehringer-Mannheim, Mannheim, Germany) was used with the "NS3KF" primer (5'-CCT GAA TTC ATG GCG CCT ATC ACG GCC TAT-3' (SEQ. ID. NO. 99) and the NS4KR primer. The NS3KF primer contained a EcoRI restriction enzyme cleavage site and a start codon and the primer NS4KR contained a XbaI restriction enzyme cleavage site and a stop codon.

The amplified fragment was then sequenced (SEQ. ID. NO. 100). Sequence comparison analysis revealed that the gene fragment was amplified from a viral strain of genotype 1a. A computerized BLAST search against the Genbank database using the NCBI website revealed that the closest HCV homologue was 93% identical in nucleotide sequence.

The amplified DNA fragment was then digested with EcoRI and XbaI, and was inserted into a pcDNA3.1/His plasmid (Invitrogen) digested with the same enzymes. The NS3/4A-pcDNA3.1 plasmid was then digested with EcoRI and Xba I and the insert was purified using the QiaQuick kit (Qiagen, Hamburg, Germany) and was ligated to a EcoRI/Xba I digested pVAX vector (Invitrogen) so as to generate the NS3/4A-pVAX plasmid.

The NS3 truncated mutant was obtained by deleting NS4A sequence from the NS3/4A DNA. Accordingly, the NS3 gene sequence of NS3/4A-pVAX was PCR amplified using the primers NS3KF and 3' NotI (5'-CCA CGC GGC CGC GAC GAC CTA CAG-3' (SEQ. ID. NO.: 101)) containing EcoRI and Not I restriction sites, respectively. The NS3 fragment (1850 bp) was then ligated to a EcoRI and Not I digested pVAX plasmid to generate the NS3-pVAX vector. Plasmids were grown in BL21 *E.coli* cells. The plasmids were sequenced and were verified by restriction cleavage and the results were as to be expected based on the original sequence.

EXAMPLE 2

To assess the ability of HBcAg DNA constructs to prime CTLs, the nucleic acid of SEQ ID NO:10 is cloned into the pVAX1 expression vector (Invitrogen, Carlsbad, Calif.) to create HBcAg-pVAX1.

Plasmids are grown in BL21 *E. coli* cells, and sequenced for accuracy. Plasmid DNA used for in vivo vaccination is purified using Qiagen DNA purification columns, according to the manufacturer's instructions (Qiagen GmbH, Hilden, FRG).

Groups of eight to ten C57/BL6 mice are primed with HBcAg-pVAX1 intra muscularly (i.m.). For i.m. delivery, mice are immunized by needle injections of 100 μg plasmid DNA given intramuscularly to the tibialis anterior (TA) muscle. 5 days prior to DNA immunization, mice are injected intramuscularly with 50 μl per TA muscle of 0.01 mM cardiotoxin (Latoxan) in 0.9% sterile saline. The mice are boosted with a second injection of 100 μg plasmid DNA four weeks subsequent to the first DNA immunization. Each injection dose contains 100 μg of plasmid DNA. Immunizations are performed at weeks 0 and 4.

The presence of CTLs specific for SEQ ID NO:10 is assayed using a standard $^{51}$Cr-release assay. Briefly, spleen cells are harvested from mice 14 days after the initial immunization or the booster immunization. Chromium release assays are performed as described in Lazdina, et al. (2003) *J. Gen. Virol.* 84:1-8, herein expressly incorporated by reference in its entirety. Single cell suspensions are prepared. $25\times10^6$ splenocytes are restimulated with $25\times10^6$ syngenic irradiated (20 Gy) splenocytes pulsed with 0.05 μM peptide, as previously described. Sandberg et al. (2000) *J. Immunol.* 165:25-33, herein expressly incorporated by reference in its entirety. Restimulation cultures are set in 12 ml complete RPMI medium (Gibco). After 5 days, effector cells are harvested and washed twice. RMA-S target cells (Karre et al. (1986) *Nature* 319:675-678) are pulsed with 50 μM peptide for 90 min at 5% $CO_2$ and 37° C. Serial dilutions of effector cells are incubated with $5\times10^3$ $^{51}$chromium-labeled peptide pulsed RMA-S target cells in a final volume of 200 μl per well in 96-well plates. After a 4 hour incubation at 5% $CO_2$ and 37° C., 100 μl of supernatant is collected and the radioactivity is determined using a γ counter. The percentage of specific release is calculated according to the formula: (Experimental release−spontaneous release/total release-spontaneous release)×100.

EXAMPLE 3

The expression of the HBcAg and NS3/4a proteins from plasmids were analyzed by an in vitro transcription and translation assay. Each sequence was cloned into pVAX1 expression vector (Invitrogen, Carlsbad, Calif.).

The following constructs were studied: (1) codon-optimized NS3/4A (SEQ. ID. No. 2); (2) codon-optimized HBcAg; (3) NS3/4A-HBcAg (SEQ. ID. No. 73); (4) mutant NS3/4A-HBcAg (SEQ. ID. No. 75); (5) NS3-NS4A/B junction-NS4-HBcAg (SEQ. ID. No. 77) (6) NS3-NS4A/B junction-NS4-NS4A/B junction-HBcAg (SEQ. ID. No. 79); and (5-11) NS3/4A- NS4A/B junction-HBcAg fragments (SEQ. ID Nos. 81, 83, 85, 87 and 89, respectively) (hereinafter Constructs 1-11, respectively).

Figure 2A:
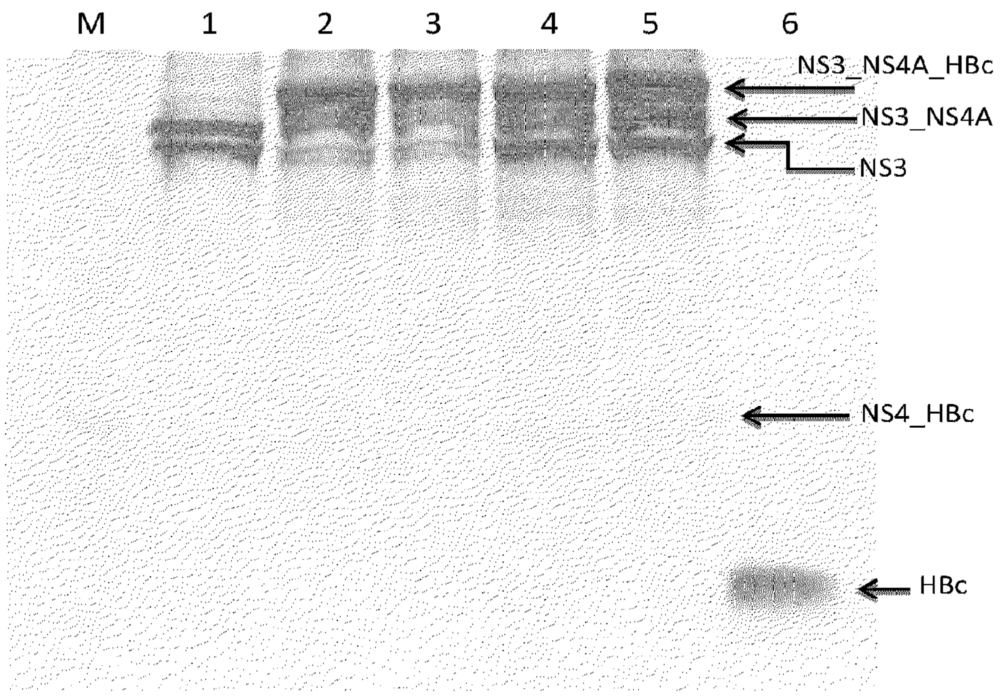
FIGS. 2(*a-b*) show the results from transcription and translation assays on nucleic acids that encode HBcAg and HCV NS3/N4A. The products were separated by gel electrophoresis.
Figure 2B:
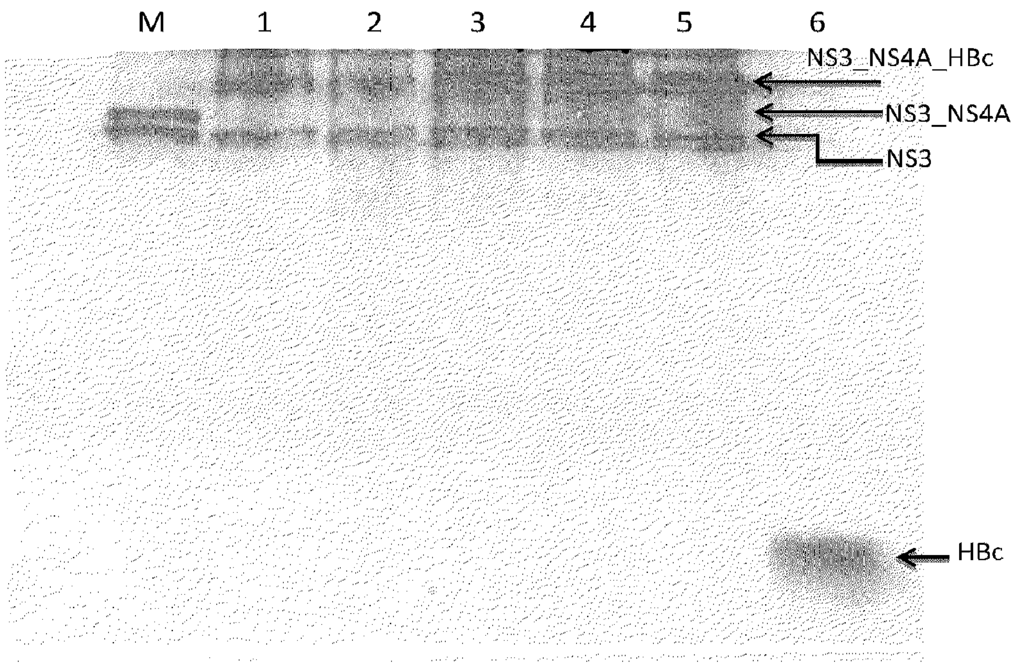

FIGS. 2*a-b* show the results of gel electrophoresis using 10% Tris-HCl SDS gel after 24 hours of exposure. The results confirm that constructs encoding cleavage sites were cleaved to form multiple, distinct proteins. For example, Construct 4 exhibits 2 sharp bands associated with two portions of the encoded polypeptide that are separated by a cleavage site. In contrast, nucleic acids lacking cleavage sites, such as Construct 2, exhibit only a single sharp band.

EXAMPLE 4

Constructs 1 and 4, as discussed in Example 3, were tested in mouse models to assay the ability to induce and immune response. Plasmids were grown in BL21 *E. coli* cells, and sequenced for accuracy. Plasmid DNA used for in vivo vaccination was purified using Qiagen DNA purification columns, according to the manufacturer's instructions (Qiagen GmbH, Hilden, FRG). The concentration of the resulting plasmid DNA was determined spectrophotometrically (Dynaquant, Pharmacia Biotech, Uppsala, Sweden) and the purified DNA was dissolved in sterile phosphate buffered saline (PBS) at a concentration of 1 mg/ml.

Two types of mice were tested, HLA-A2 transgenic mice (HHD) and HCV NS3/4A+HLA-A2 transgenic mice (H3). The HCV NS3/4A+HLA-A2 transgenic mouse model is a preferred animal model for therapeutic vaccination because it provides a partly human immune system that is dysfunctional due to a persistent presence of a viral antigen. Accordingly, this model is representative of chronic HCV infection in humans.

Mice were intra muscularly (i.m.) immunized with 50 μg of Construct 1 or 4 at 0 and 4 weeks. Meanwhile, four other mice groups were co-administered 50 μg of IL-12 or IL-21 along with Construct 1 or 4 at 0 and 4 weeks. Mice were sacrificed at week 6 and spleens harvested and analyzed for HCV-specific IFNγ production by ELISpot as described in Ahlen G, Soderholm J, Tjelle T E, et al. "In vivo Electroporation Enhances the Immunogenicity of Hepatitis C Virus Nonstructural3/4A DNA by Increased Local DNA Uptake, Protein Expression, Inflammation, and Infiltration of CD3+ cells," J. Immunol. (2007), which is hereby incorporated by reference in its entirety. Table 1 provided below shows a list of restricted peptides in the transgenic mice whose expression was detected using ELISpot.

| IDENTIFIER | RESTRICTED SEQUENCE | SEQ. ID. NO. |
|---|---|---|
| TP-5 | GLLGCIITSL | 90 |
| TP-6 | TGSPITYSTY | 91 |
| TP-7 | KLVALGVNAV | 92 |
| TP-9 | CINGVCWTV | 93 |
| TP-10 | LLCPAGHAV | 94 |
| TP-11 | ATMGFGAYM | 95 |
| TP-12 | YLVAYQATV | 96 |
| TP-13 | TLHGPTPLL | 97 |

Figure 3A:
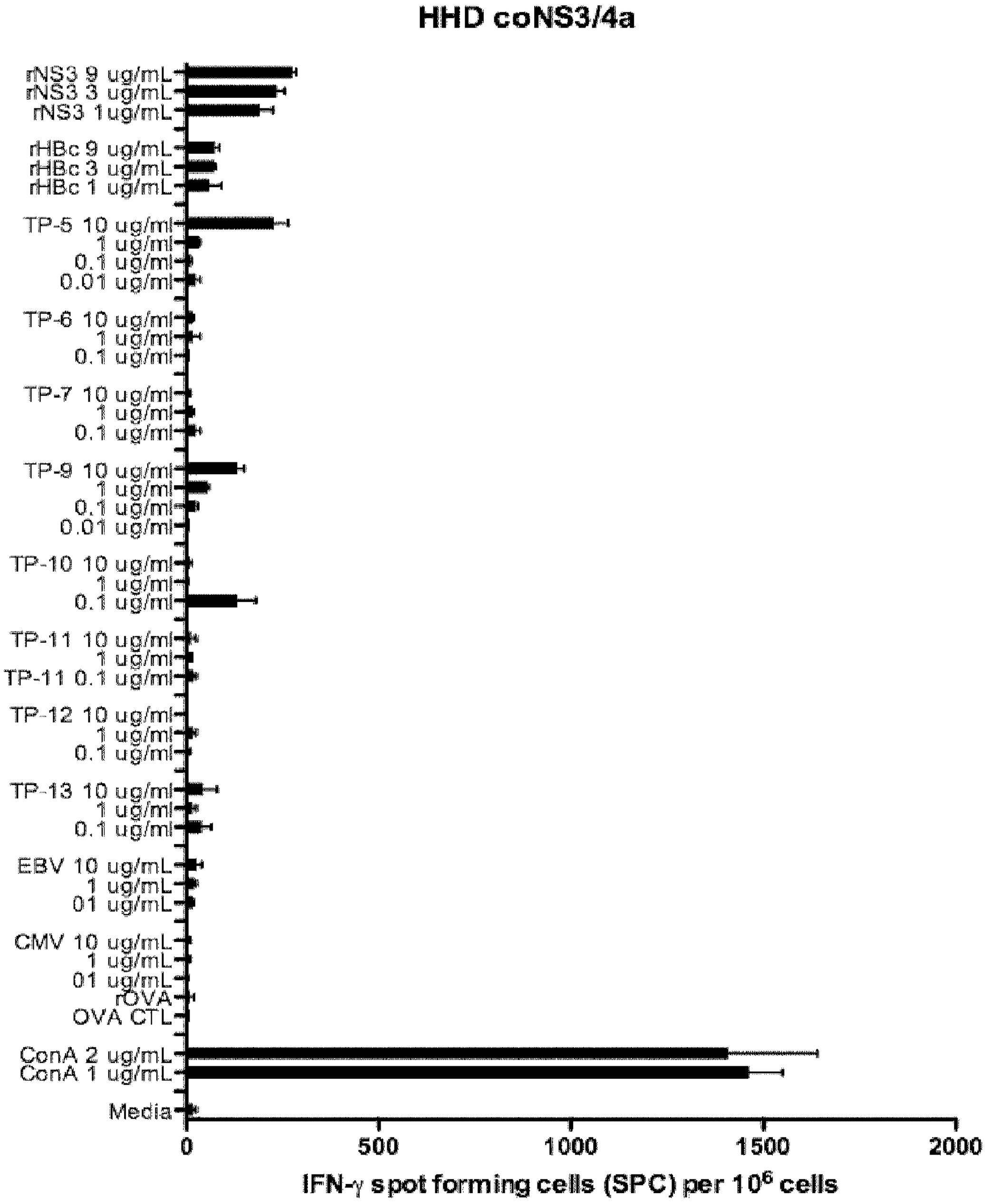
FIGS. 3(*a-e*) show the results from an ELISpot assay conducted on HLA-A2 transgenic mice, which had been administered nucleic acids that encode HBcAg and HCV NS3/N4A.
Figure 3B:
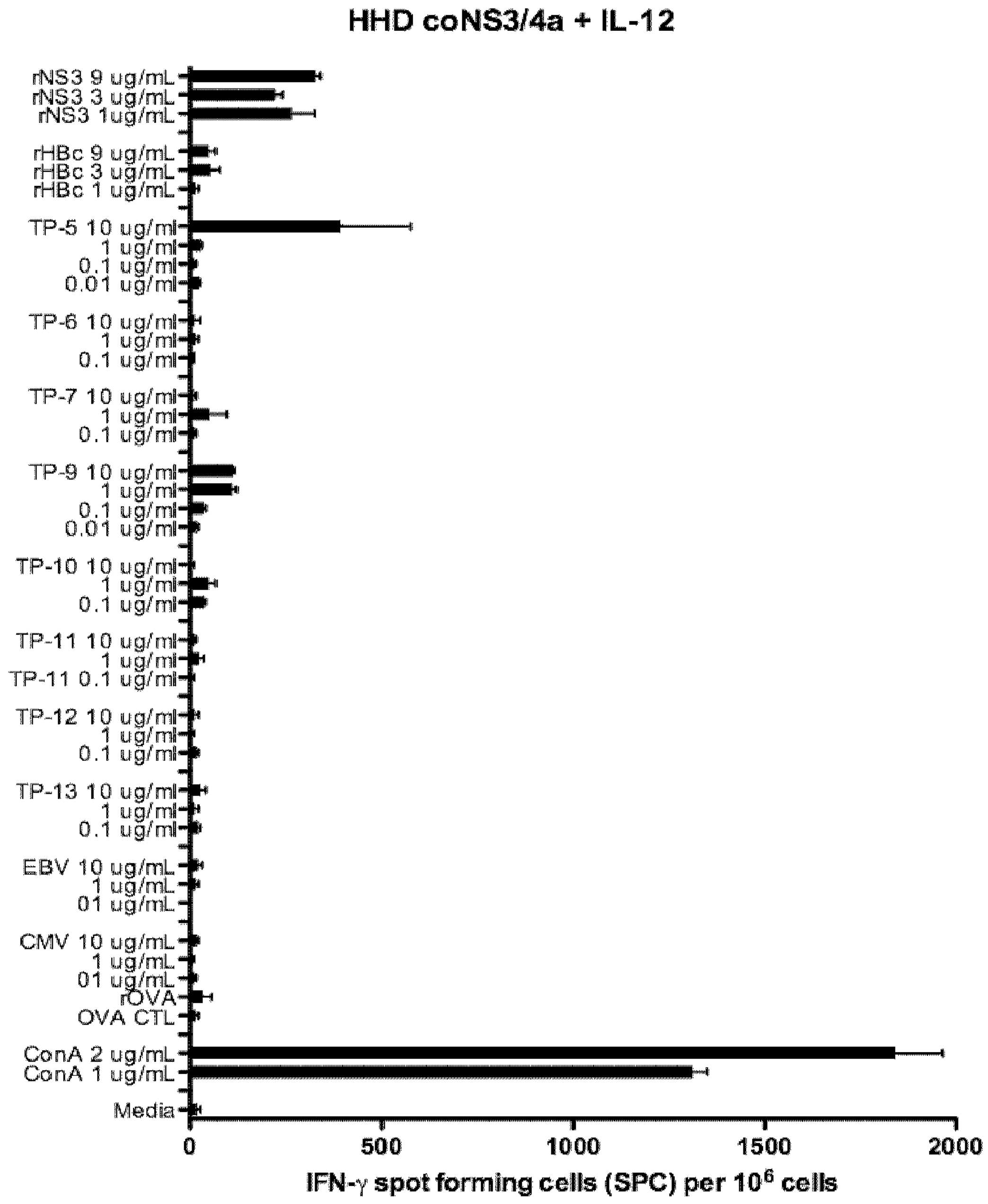
Figure 3C:
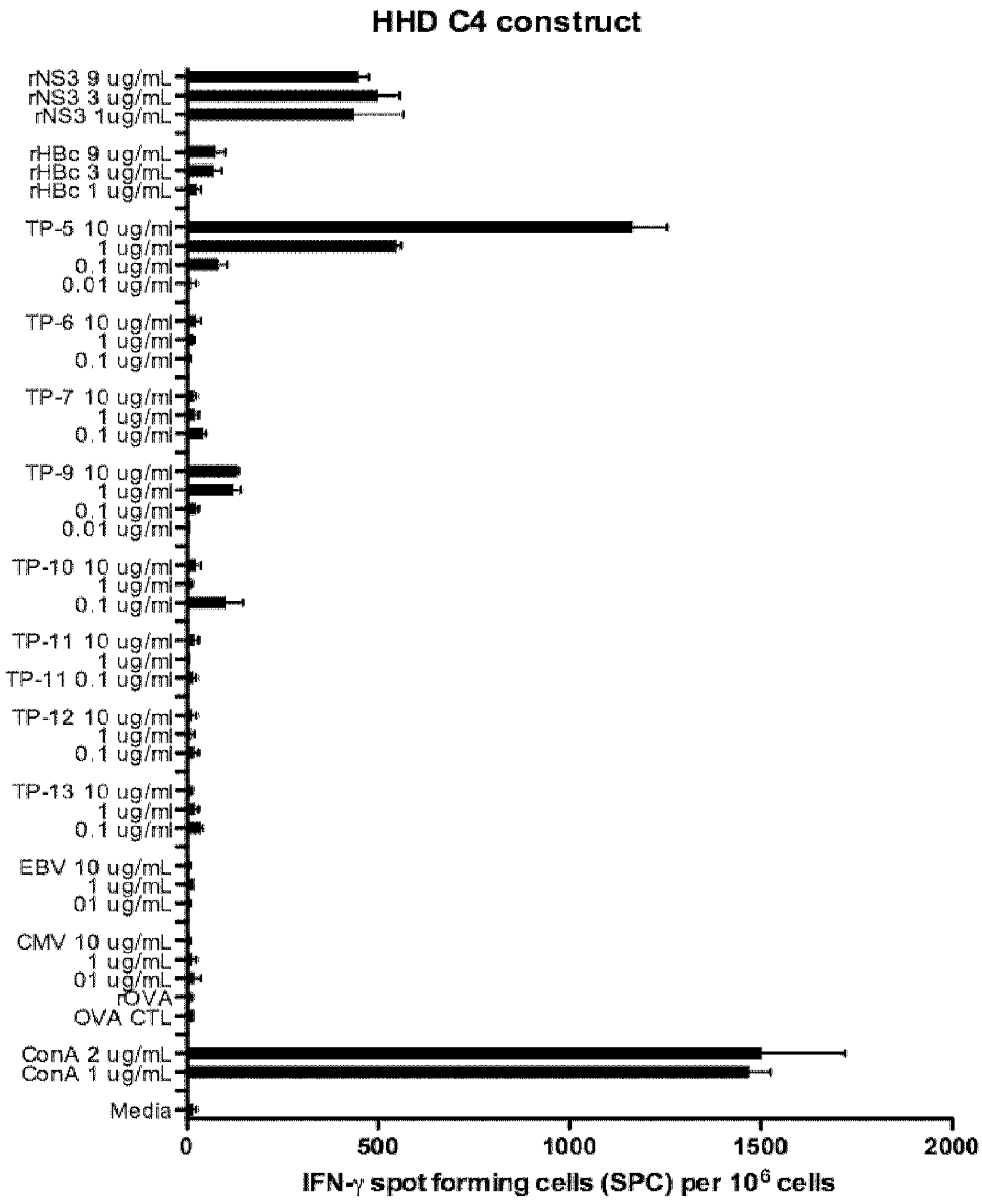
Figure 3D:
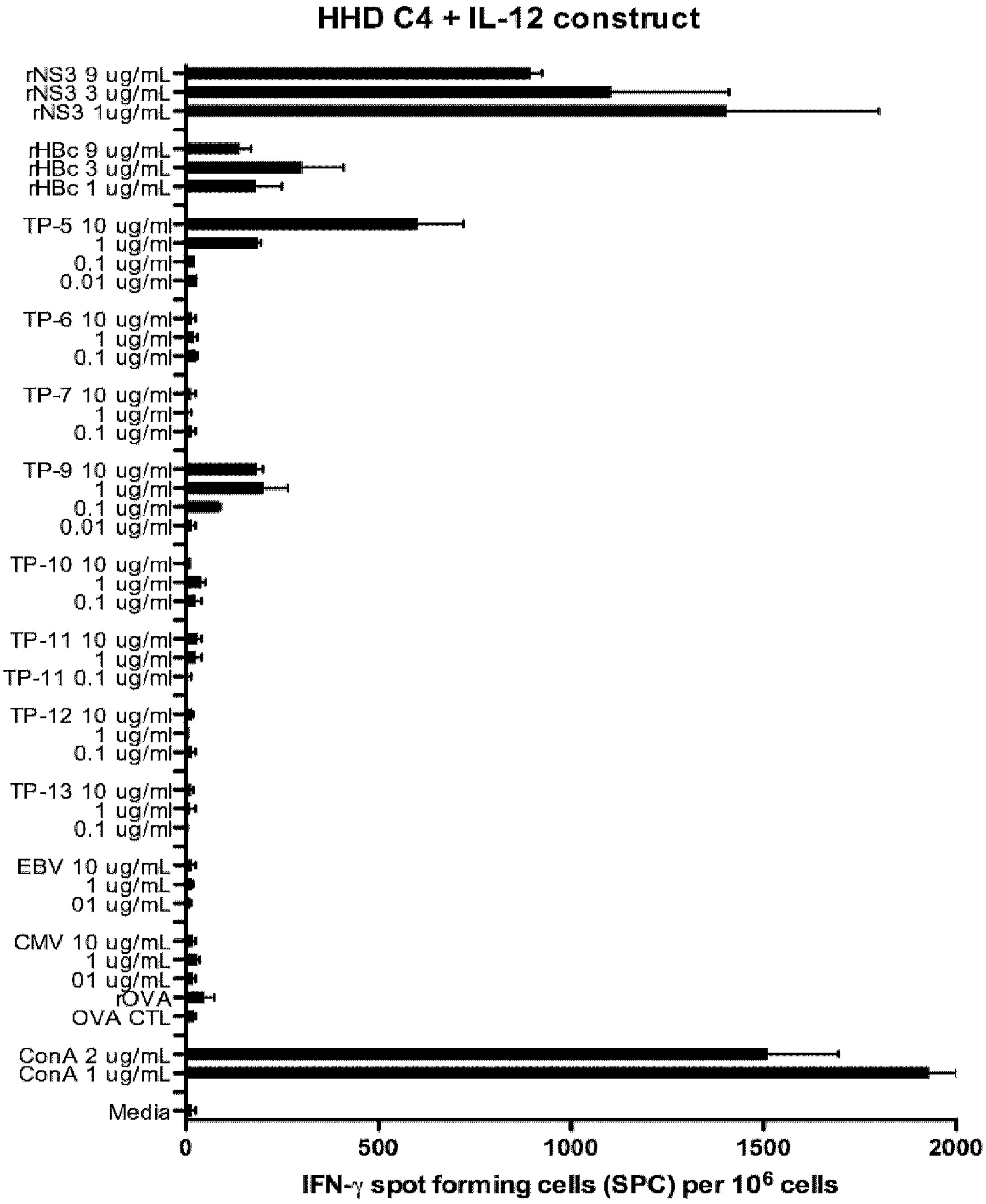
Figure 3E:
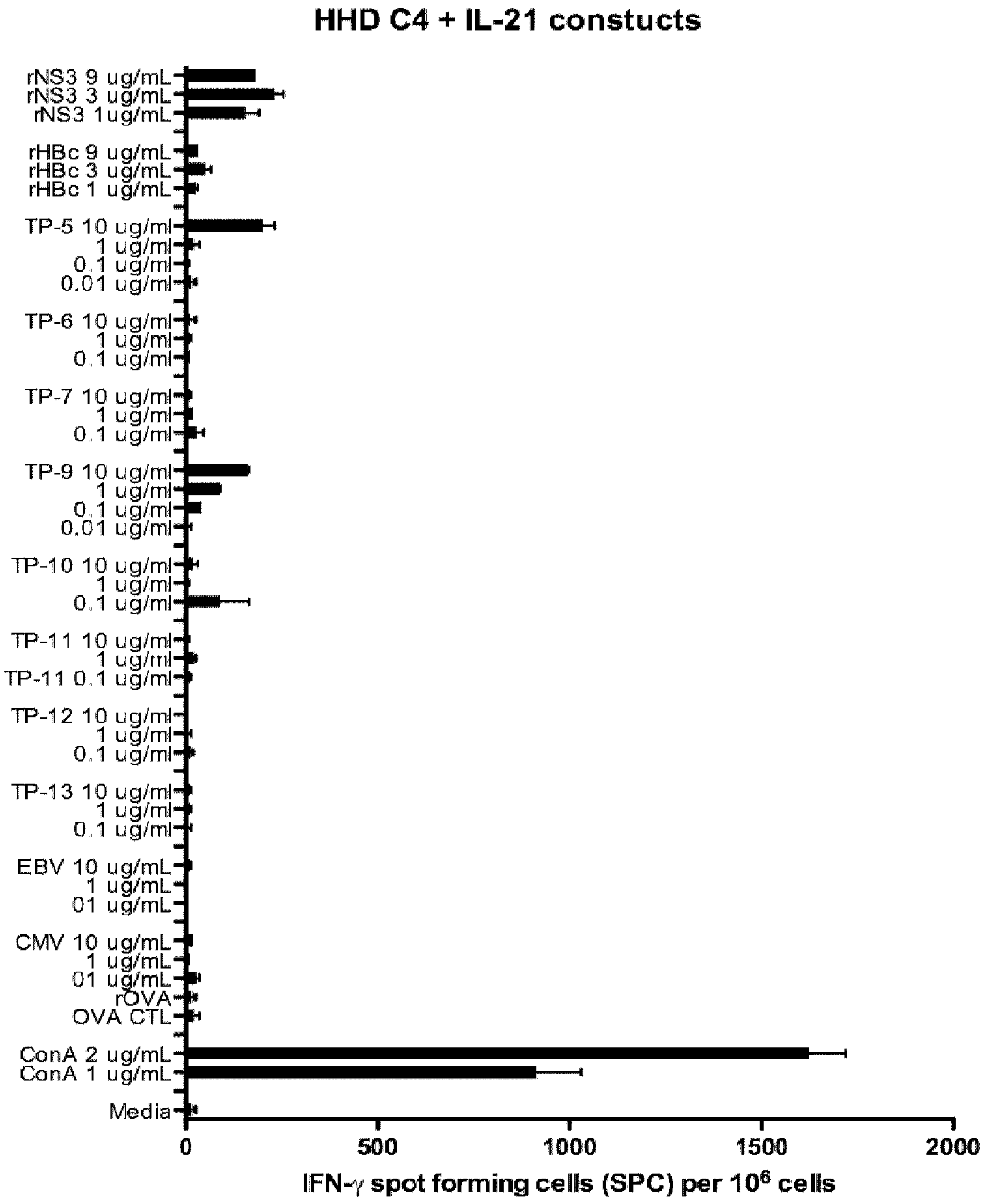
Figure 4A:
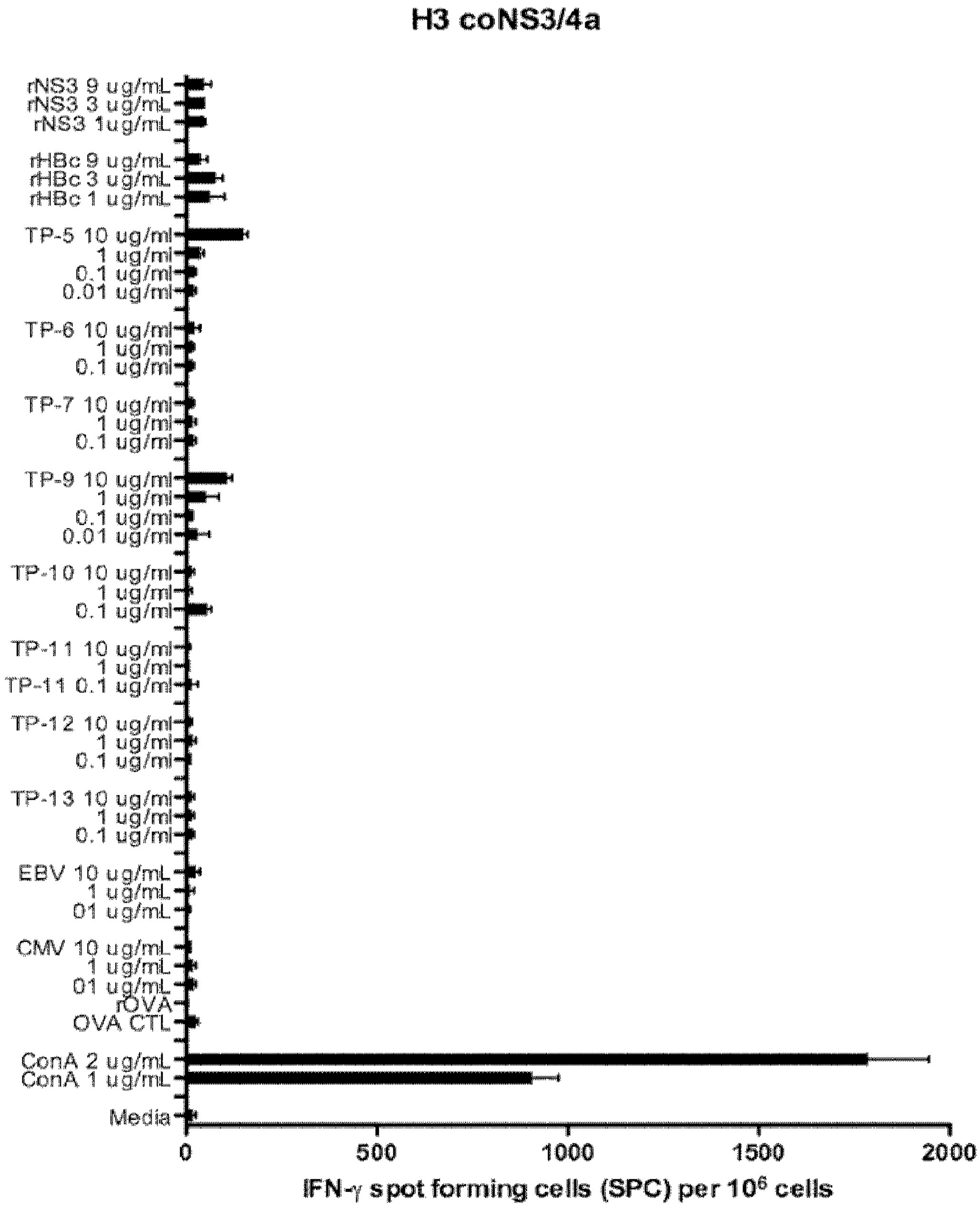
FIGS. 4(*a-e*) show the results of an ELISpot assay conducted on HCV NS3/4A+HLA-A2 transgenic mice, which had been administered nucleic acids that encode HBcAg and HCV NS3/N4A.
Figure 4B:
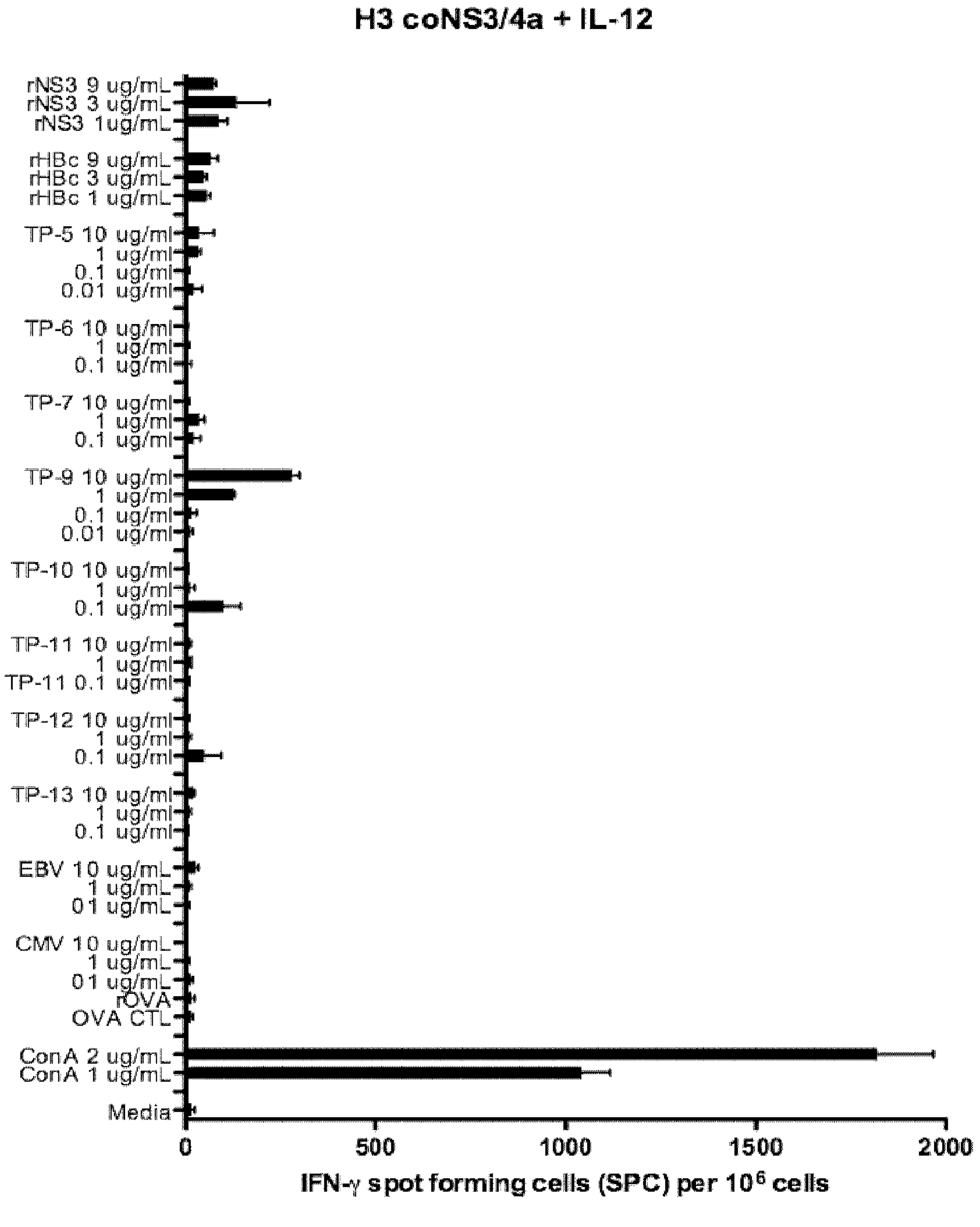
Figure 4C:
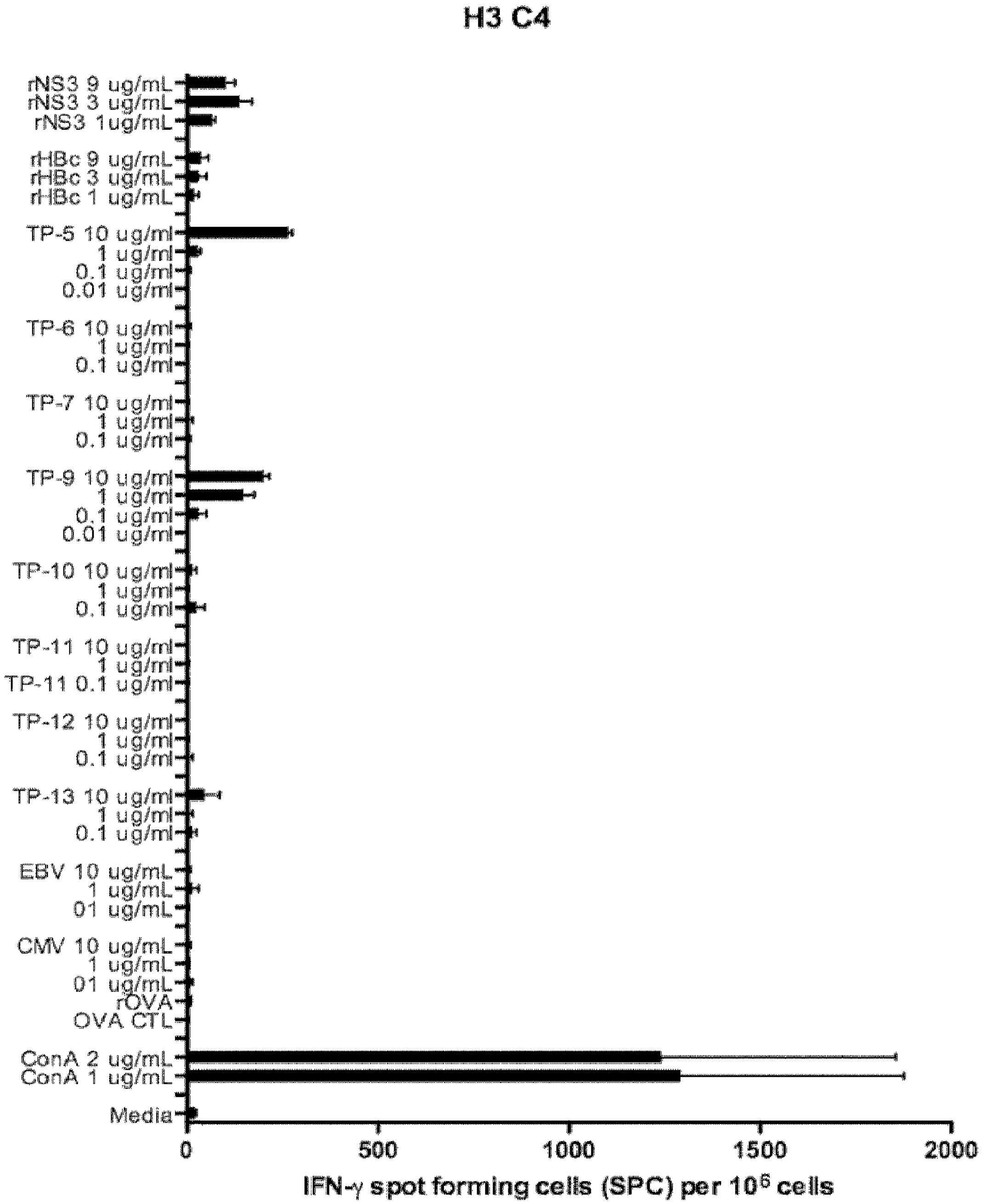

ELISpot results are shown in FIGS. 3*a-e* and 4*a-e* for the HHD and H3 animal models, respectively. More specifically, FIG. 3*a-c* shows the immune response from the administration of codon-optimized NS3/4A (Construct 1), codon-optimized NS3/4A coadministered with IL-12, and mutant NS3/4A-HBcAg (Construct 4), respectively, when administered to HHD mice. The adjuvant activity of HBcAg is demonstrated by the increased immune response of mice receiving Construct 4 relative to both Construct 1 and Construct 1 co-administered with IL-12. FIGS. 4*a-c* show the immune response from the administration of codon-optimized NS3/4A (Construct 1), codon-optimized NS3/4A coadministered with IL-12, and mutant NS3/4A-HBcAg (Construct 4), respectively, when administered to H3 mice. These results further demonstrate the adjuvant activity of HBcAg.

Figure 4D:
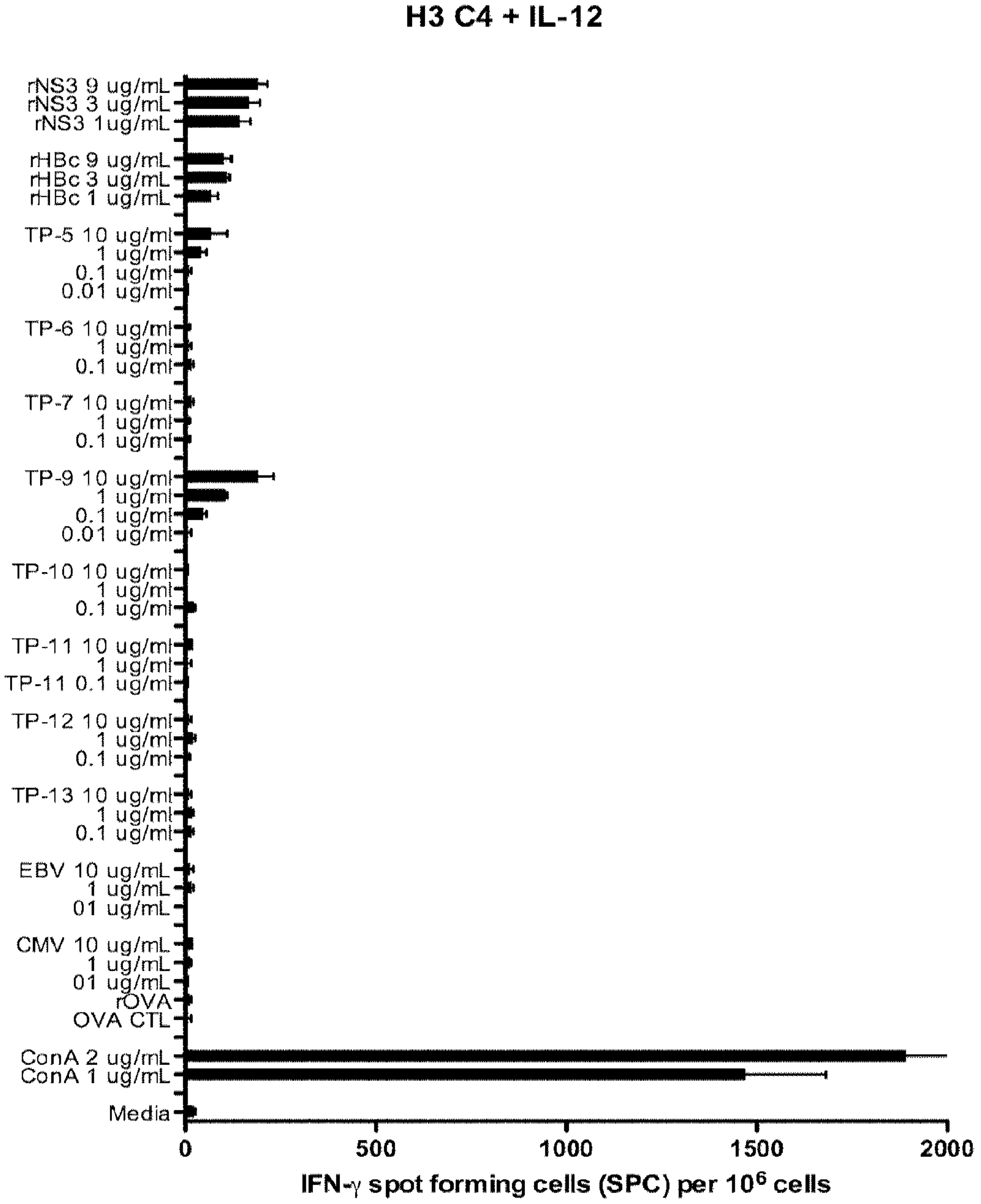
Figure 4E:
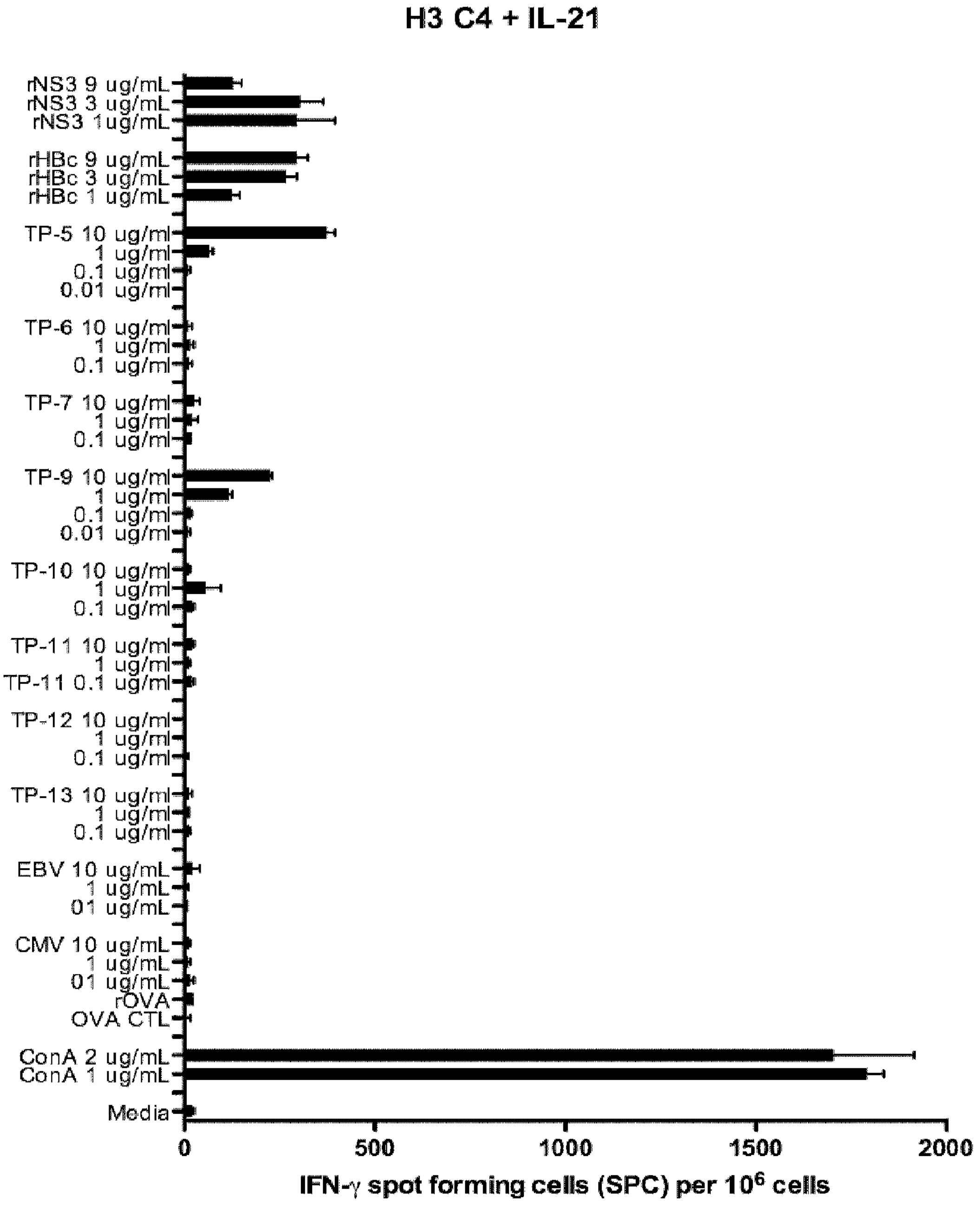

To further improve the immune response, mutant NS3/4A-HBcAg was co-administered with either IL-12 or IL-21 to HHD and H3 mice. FIGS. 3*d-e* show results in the HHD mouse model, and demonstrate the immune response is further increased by the addition of IL-12 or IL-21, relative to mutant NS3/4A-HBcAg administered alone (i.e., as shown in FIG. 3*c*). The results show IL-12 produced generally a greater immune response compared to IL-21. Finally, FIGS. 4*d-e* show the results in the H3 mouse model. Again, both IL-12 and IL-21 improved the immune response of mutant NS3/4A-HBcAg relative the administration of mutant NS3/4A-HBcAg alone (i.e., as shown in FIG. 4*c*). Most interestingly, IL-21 produced a generally greater immune response in H3 mouse compared to IL-12.

EXAMPLES 4-13

To further evaluate the adjuvant activity of HBcAg, both HHD and H3 transgenic mice are instramuscularly administered compositions having constructs encoding HBcAg and isolated constructs encoding an antigen. To prepare each construct, each sequence is independently cloned into a separate pVAX1 expression vector (Invitrogen, Carlsbad, Calif.). The plasmids are prepared generally using the same techniques as disclosed in Example 2.

Compositions are prepared by admixing a vector encoding codon-optimized HBcAg and a vector encoding an antigen in sterile phosphate buffered saline (PBS) at a concentration of 1 mg/ml. 50 μg of this mixture is administered intramuscularly to HHD and H3 mice using the same techniques and analyzed using ELISpot as described in Example 3. These results are compared to mice receiving antigen but without co-administered HBcAg.

Table 2 below lists the specific nucleic acids inserted into vectors and contained in the admixtures administered for Examples 4-13. Thus, for example, Example 4 includes the administration of a vector encoding codon-optimized stork HBcAg, and a vector encoding codon-optimized NS3/4A.

| EXAMPLE | HBcAg (SEQ. ID. No.) | ANTIGEN (SEQ. ID. NO.) |
|---|---|---|
| 4 | 20 | 2 |
| 5 | 22 | 2 |
| 6 | 20 | 8 |
| 7 | 22 | 8 |
| 8 | 20 | 10 |
| 9 | 22 | 10 |
| 10 | 20 | 12 |
| 11 | 22 | 12 |
| 12 | 20 | 16 |
| 13 | 22 | 16 |
| 14 | 20 | 18 |
| 15 | 22 | 18 |

It will be shown that the presence of HBcAg in the composition promotes a more robust immune response to the antigen in the subject, as compared to administration of a composition of antigen that excludes effective amounts of HBcAg.

EXAMPLES 14-43

Additional experiments to study the immunogenic properties of isolated nucleic acids encoding HBcAg joined to a heterologous protein can be performed. The procedures are generally the same as those described in Example 4, which briefly includes inserting the sequence into the pVAX1 plasmid and administering a composition of the plasmid to HHD and H3 transgenic mice. The immune response is determined using ELISpot and compared to the immune response resulting from administering plasmids encoding the antigen without HBcAg. The nucleic acids used in Examples 14-43 are shown below in Table 3.

| EXAMPLE | NUCLEIC ACID (SEQ. ID. NO.) |
|---|---|
| 14 | 24 |
| 15 | 26 |
| 16 | 28 |
| 17 | 30 |
| 18 | 32 |
| 19 | 34 |
| 20 | 36 |
| 21 | 38 |
| 22 | 40 |
| 23 | 42 |
| 24 | 44 |
| 25 | 46 |
| 26 | 48 |
| 27 | 50 |
| 28 | 52 |
| 29 | 54 |
| 30 | 56 |
| 31 | 58 |
| 32 | 60 |
| 33 | 62 |
| 34 | 64 |
| 35 | 66 |
| 36 | 68 |
| 37 | 81 |
| 38 | 83 |
| 49 | 85 |
| 40 | 87 |
| 41 | 89 |
| 42 | 103 |
| 43 | 105 |

It will be shown that the compositions having HBcAg joined to an antigen promote a more robust immune response to the antigen in the subject, as compared to administration of a composition of antigen that excludes effective amounts of HBcAg joined to the antigen.

What is claimed is:

1. An isolated nucleic acid comprising:

a nucleotide sequence encoding a fusion protein of a hepatitis B virus core antigen (HBcAg) from an avian hepatitis virus joined to a hepatitis C virus (HCV) antigen, wherein said HCV antigen comprises NS3/4A and, wherein said nucleotide sequence is codon optimized for expression in humans.

2. The isolated nucleic acid of claim 1, wherein said HCV antigen further comprises NS5A.

3. The isolated nucleic acid of claim 1, wherein one or more protein cleavage sites are encoded between the HBcAg portion and the NS3/4A antigen portion of said fusion protein.

4. The isolated nucleic acid of claim 3, wherein said one or more protein cleavage sites are included at a non-naturally occurring position with respect to the HBcAg.

5. The isolated nucleic acid of claim 3, wherein said one or more protein cleavage sites are NS3 protease cleavage sites.

6. The isolated nucleic acid of claim 1, wherein said HBcAg is from a hepatitis virus that infects a stork.

7. The isolated nucleic acid of claim 1, wherein said HBcAg is from a hepatitis virus that infects a heron.

8. An immunogenic composition comprising:

an isolated nucleic acid that comprises a nucleotide sequence encoding a fusion protein of a hepatitis B virus core antigen (HBcAg) from an avian hepatitis virus joined to a hepatitis C virus (HCV) antigen, wherein said nucleotide sequence is codon optimized for expression in humans and said HCV antigen comprises NS3/4A.

9. The immunogenic composition of claim 8, further comprising an adjuvant.

10. The immunogenic composition of claim 9, wherein said adjuvant is selected from the group consisting of: interleukin 2 (IL-2), interleukin 12 (IL-12), interleukin 15 (IL-15), and interleukin 21 (IL-21).

11. The immunogenic composition of claim 8, wherein said HCV antigen further comprises NS5A.

12. The immunogenic composition of claim 8, wherein one or more protein cleavage sites are encoded between the HBcAg portion and the NS3/4A antigen portion of said fusion protein.

13. The immunogenic composition of claim 8, wherein said one or more protein cleavage sites are included at a non-naturally occurring position with respect to the HBcAg.

14. The immunogenic composition of claim 8, wherein said one or more protein cleavage sites are NS3 protease cleavage sites.

15. The immunogenic composition of claim 8, wherein said HBcAg is from a hepatitis virus that infects a stork.

16. The immunogenic composition of claim 8, wherein said HBcAg is from a hepatitis virus that infects a heron.

17. A method of inducing an immune response to a hepatitis C virus (HCV) antigen in a subject comprising:

providing the nucleic acid of claim 1 or the immunogenic composition of claim 8 to a subject; and evaluating the immune response of said subject to said HCV antigen.

18. The method of claim 17, wherein the subject is infected with hepatitis B virus (HBV) or the subject that has antibodies specific for HBV.

* * * * *

SEQUENCE LISTING

```
<160> NUMBER OF SEQ ID NOS: 106

<210> SEQ ID NO 1
<211> LENGTH: 686
<212> TYPE: PRT
<213> ORGANISM: Artificial Sequence
<220> FEATURE:
<223> OTHER INFORMATION: Codon optimized HCV NS3-NS4A (active)

<400> SEQUENCE: 1

Met Ala Pro Ile Thr Ala Tyr Ala Gln Gln Thr Arg Gly Leu Leu Gly
 1              5                  10                  15
```

-continued

```
Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
```

-continued

```
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685


<210> SEQ ID NO 2
<211> LENGTH: 2061
<212> TYPE: DNA
<213> ORGANISM: Artificial Sequence
<220> FEATURE:
<223> OTHER INFORMATION: Codon optimized HCV NS3/4a (active)

<400> SEQUENCE: 2

atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgcccccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480

acccgcggcg tggccaaggc cgtggacttc atccccgtgg agagcctgga gaccaccatg     540

cgcagccccg tgttcagcga caacagcagc cccccccgccg tgccccagag ctaccaggtg     600

gcccacctgc acgcccccac cggcagcggc aagagcacca aggtgcccgc cgcctacgcc     660

gcccagggct acaaggtgct ggtgctgaac cccagcgtgg ccgccaccat gggcttcggc     720
```

-continued

```
gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccacccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgctg a                                             2061
```

<210> SEQ ID NO 3
<211> LENGTH: 18
<212> TYPE: PRT
<213> ORGANISM: Artificial Sequence
<220> FEATURE:
<223> OTHER INFORMATION: HCV NS3/4A junction

<400> SEQUENCE: 3

```
Ser Ala Asp Leu Glu Val Val Thr Ser Thr Trp Val Leu Val Gly Gly
 1               5                  10                  15

Val Leu
```

<210> SEQ ID NO 4
<211> LENGTH: 54
<212> TYPE: DNA
<213> ORGANISM: Artificial Sequence
<220> FEATURE:
<223> OTHER INFORMATION: HCV NS3/4A junction

<400> SEQUENCE: 4

```
agcgccgacc tggaggtggt gaccagcacc tgggtgctgg tgggcggcgt gctg          54
```

<210> SEQ ID NO 5
<211> LENGTH: 16
<212> TYPE: PRT
<213> ORGANISM: Artificial Sequence
<220> FEATURE:

-continued

<223> OTHER INFORMATION: HCV NS4A/B junction

<400> SEQUENCE: 5

```
Asp Glu Met Glu Glu Cys Ser Gln His Leu Pro Tyr Ile Glu Gln Gly
 1               5                  10                  15
```

<210> SEQ ID NO 6
<211> LENGTH: 48
<212> TYPE: DNA
<213> ORGANISM: Artificial Sequence
<220> FEATURE:
<223> OTHER INFORMATION: HCV NS4A/B junction

<400> SEQUENCE: 6

```
gacgagatgg aggagtgcag ccagcacctg ccctacatcg agcagggc                  48
```

<210> SEQ ID NO 7
<211> LENGTH: 449
<212> TYPE: PRT
<213> ORGANISM: Artificial Sequence
<220> FEATURE:
<223> OTHER INFORMATION: Codon optimized HCV NS5A genotype 1b

<400> SEQUENCE: 7

```
Met Gly Ser Gly Ser Trp Leu Arg Asp Val Trp Asp Trp Ile Cys Thr
 1               5                  10                  15

Val Leu Thr Asp Phe Lys Thr Trp Leu Gln Ser Lys Leu Leu Pro Lys
            20                  25                  30

Leu Pro Gly Val Pro Phe Phe Ser Cys Gln Arg Gly Tyr Lys Gly Val
        35                  40                  45

Trp Arg Gly Asp Gly Ile Met Gln Thr Thr Cys Pro Cys Gly Ala Gln
    50                  55                  60

Ile Thr Gly His Val Lys Asn Gly Ser Met Arg Ile Val Gly Pro Lys
65                  70                  75                  80

Thr Cys Ser Asn Thr Trp His Gly Thr Phe Pro Ile Asn Ala Tyr Thr
                85                  90                  95

Thr Gly Pro Cys Thr Pro Ser Pro Ala Pro Asn Tyr Ser Arg Ala Leu
            100                 105                 110

Trp Arg Val Ala Ala Glu Glu Tyr Val Glu Ile Thr Arg Val Gly Asp
        115                 120                 125

Phe His Tyr Val Thr Gly Met Thr Thr Asp Asn Val Lys Cys Pro Cys
    130                 135                 140

Gln Val Pro Ala Pro Glu Phe Phe Thr Glu Leu Asp Gly Val Arg Leu
145                 150                 155                 160

His Arg Tyr Ala Pro Ala Cys Arg Pro Leu Leu Arg Glu Asp Val Thr
                165                 170                 175

Phe Gln Val Gly Leu Asn Gln Tyr Leu Val Gly Ser Gln Leu Pro Cys
            180                 185                 190

Glu Pro Glu Pro Asp Val Ala Val Leu Thr Ser Met Leu Thr Asp Pro
        195                 200                 205

Ser His Ile Thr Ala Glu Thr Ala Lys Arg Arg Leu Ala Arg Gly Ser
    210                 215                 220

Pro Pro Ser Leu Ala Ser Ser Ser Ala Ser Gln Leu Ser Ala Pro Ser
225                 230                 235                 240

Leu Lys Ala Thr Cys Thr Thr His His Asp Ser Pro Asp Ala Asp Leu
                245                 250                 255

Ile Glu Ala Asn Leu Leu Trp Arg Gln Glu Met Gly Gly Asn Ile Thr
            260                 265                 270
```

```
Arg Val Glu Ser Glu Asn Lys Val Val Ile Leu Asp Ser Phe Asp Pro
        275                 280                 285

Leu Arg Ala Glu Glu Asp Glu Arg Glu Val Ser Val Ala Ala Glu Ile
    290                 295                 300

Leu Arg Lys Ser Lys Lys Phe Pro Pro Ala Leu Pro Ile Trp Ala Arg
305                 310                 315                 320

Pro Asp Tyr Asn Pro Pro Leu Leu Glu Ser Trp Lys Ser Pro Asp Tyr
                325                 330                 335

Val Pro Pro Ala Val His Gly Cys Pro Leu Pro Pro Thr Thr Gly Pro
            340                 345                 350

Pro Ile Pro Pro Pro Arg Lys Lys Arg Thr Val Val Leu Thr Glu Ser
        355                 360                 365

Thr Val Ser Ser Ala Leu Ala Glu Leu Ala Thr Lys Thr Phe Gly Ser
    370                 375                 380

Ser Gly Ser Ser Ala Val Asp Ser Gly Thr Ala Thr Ala Pro Pro Asp
385                 390                 395                 400

Gln Thr Ser Asp Asp Gly Asp Lys Glu Ser Asp Ile Glu Ser Tyr Ser
                405                 410                 415

Ser Met Pro Pro Leu Glu Gly Glu Pro Gly Asp Pro Asp Leu Ser Asp
            420                 425                 430

Gly Ser Trp Ser Thr Val Ser Gly Glu Ala Gly Asp Asp Ile Val Cys
        435                 440                 445

Cys


<210> SEQ ID NO 8
<211> LENGTH: 1350
<212> TYPE: DNA
<213> ORGANISM: Artificial Sequence
<220> FEATURE:
<223> OTHER INFORMATION: Codon optimized HCV NS5A genotype 1b

<400> SEQUENCE: 8

atgggatctg gaagctggct gagggatgtt tgggattgga tttgtaccgt cctcaccgac      60

ttcaaaacct ggctccagtc caagctgctg ccaaagctgc ccggagtgcc attcttctcc     120

tgtcagaggg gctataaagg cgtgtggagg ggcgatggaa ttatgcagac tacttgcccc     180

tgtggagctc aaattactgg gcacgttaag aatggctcca tgcggattgt tggcccaaaa     240

acctgttcca acacctggca cggaaccttc cctattaacg cttacaccac cggaccttgc     300

actccttccc ccgcacctaa ttattcccgg gctctctggc gggtggcagc agaggaatat     360

gtcgaaatta ccagagtcgg cgacttccac tacgtcacag gaatgactac agacaacgtt     420

aaatgtccct gccaagtgcc cgctccagag ttctttaccg aactcgacgg ggttaggctc     480

cacagatacg cacccgcctg ccggccactg ctgcgggaag acgtcacatt ccaggtcggg     540

ctgaaccagt acctggtggg ctctcagctg ccttgtgagc ctgagcccga cgtggcagtt     600

ctcaccagca tgctcaccga tcctagccac atcaccgctg agacagccaa acgccgcctg     660

gctagagggt cccctccctc tctggccagc tccagcgcta gccagctctc cgcaccaagc     720

ctgaaagcca catgcactac acaccacgat agccccgacg cagacctgat tgaagccaac     780

ctcctctgga gacaggaaat gggcggaaac atcactaggg tcgaatccga gaataaagtg     840

gttattctgg atagcttcga cccactcagg gcagaggaag atgagagaga ggttagcgtg     900

gccgctgaga ttctccgcaa gtccaaaaag ttccctcccg cactgcccat ttgggcaagg     960

cccgattaca atcctccact gctcgagagc tggaagtccc ctgactacgt gccaccagcc    1020

gtccacggat gccctctgcc ccctaccaca ggaccaccaa ttccaccccc tagaaagaaa    1080
```

-continued cggaccgtgg ttctgactga gtccaccgtg tcctctgcac tcgctgagct ggcaaccaag 1140
acctttggat ccagcggatc ctccgcagtc gactccggca ccgctaccgc cccacccgat 1200
caaacctctg acgatggaga caaggagagc gatattgagt cctattccag catgccccca 1260
ctcgagggag aacccggcga ccccgacctg agcgatgggt cctggagcac tgtgagcggg 1320
gaagcagggg acgacattgt ctgttgctga 1350

<210> SEQ ID NO 9
<211> LENGTH: 183
<212> TYPE: PRT
<213> ORGANISM: Artificial Sequence
<220> FEATURE:
<223> OTHER INFORMATION: Codon optimized HBV HBcAg subtype ayw

<400> SEQUENCE: 9

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Glu Ala Leu Glu Ser Pro Glu His Cys
35 40 45

Ser Pro His His Thr Ala Leu Arg Gln Ala Ile Leu Cys Trp Gly Glu
50 55 60

Leu Met Thr Leu Ala Thr Trp Val Gly Val Asn Leu Glu Asp Pro Ala
65 70 75 80

Ser Arg Asp Leu Val Val Ser Tyr Val Asn Thr Asn Met Gly Leu Lys
85 90 95

Phe Arg Gln Leu Leu Trp Phe His Ile Ser Cys Leu Thr Phe Gly Arg
100 105 110

Glu Thr Val Ile Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Ser Pro Arg Arg Arg Thr
145 150 155 160

Pro Ser Pro Arg Arg Arg Arg Ser Gln Ser Pro Arg Arg Arg Arg Ser
165 170 175

Gln Ser Arg Glu Ser Gln Cys
180

<210> SEQ ID NO 10
<211> LENGTH: 552
<212> TYPE: DNA
<213> ORGANISM: Artificial Sequence
<220> FEATURE:
<223> OTHER INFORMATION: Codon optimized HBV HBcAg subtype ayw

<400> SEQUENCE: 10
atggacatcg acccctacaa ggagttcggc gccaccgtgg agctgctgag cttcctgccc 60
agcgacttct tccccagcgt gagagacctg ctggacaccg ccagcgccct gtacagagag 120
gccctggaga gccccgagca ctgcagcccc caccacaccg ccctgagaca ggccatcctg 180
tgctggggcg agctgatgac cctggccacc tgggtgggcg tgaacctgga ggaccccgcc 240
agcagagacc tggtggtgag ctacgtgaac accaacatgg gcctgaagtt cagacagctg 300
ctgtggttcc acatcagctg cctgaccttc ggcagagaga ccgtgatcga gtacctggtg 360
agcttcggcg tgtggatcag aacccccccc gcctacagac cccccaacgc ccccatcctg 420

```
agcaccctgc ccgagaccac cgtggtgaga agaagaggca gaagccccag aagaagaacc    480

cccagcccca gaagaagaag aagccagagc cccagaagaa gaagaagcca gagcagagag    540

agccagtgct ag                                                        552
```

<210> SEQ ID NO 11
<211> LENGTH: 212
<212> TYPE: PRT
<213> ORGANISM: Artificial Sequence
<220> FEATURE:
<223> OTHER INFORMATION: Codon optimized HBV HBeAg subtype ayw

<400> SEQUENCE: 11

```
Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 12
<211> LENGTH: 639
<212> TYPE: DNA
<213> ORGANISM: Artificial Sequence
<220> FEATURE:
<223> OTHER INFORMATION: Codon optimized HBV HBeAg subtype ayw

<400> SEQUENCE: 12

```
atgcagctgt tccacctgtg cctgatcatc agctgcagct gccccaccgt gcaggccagc     60

aagctgtgcc tgggctggct gtggggcatg gacatcgacc cctacaagga gttcggcgcc    120

accgccgagc tgctgagctt cctgcccagc gacttcttcc ccagcgtgag agacctgctg    180

gacaccgcca gcgccctgta cagagaggcc ctggagagcc ccgagcactg cagcccccac    240

cacaccgccc tgagacaggc catcctgtgc tggggcgagc tgatgaccct ggccacctgg    300

gtgggcgtga acctggagga ccccgccagc agagacctgg tggtgagcta cgtgaacacc    360
```

-continued

```
aacatgggcc tgaagttcag acagctgctg tggttccaca tcagctgcct gaccttcggc    420

agagagaccg tgatcgagta cctggtgagc ttcggcgtgt ggatcagaac cccccccgcc    480

tacagacccc ccaacgcccc catcctgagc accctgcccg agaccaccgt ggtgagaaga    540

agaggcagaa gccccagaag aagaaccccc agccccagaa gaagaagaag ccagagcccc    600

agaagaagaa gaagccagag cagagagagc cagtgctag                           639


<210> SEQ ID NO 13
<211> LENGTH: 212
<212> TYPE: PRT
<213> ORGANISM: Artificial Sequence
<220> FEATURE:
<223> OTHER INFORMATION: Codon optimized HBV HBeAg subtype ayw

<400> SEQUENCE: 13

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Leu Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 14
<211> LENGTH: 639
<212> TYPE: DNA
<213> ORGANISM: Artificial Sequence
<220> FEATURE:
<223> OTHER INFORMATION: Codon optimized HBV HBeAg subtype ayw

<400> SEQUENCE: 14

atgcagctgt tccacctgtg cctgatcatc agctgcagct gccccaccgt gcaggccagc     60

aagctgtgcc tgggctggct gtggggcctg gacatcgacc cctacaagga gttcggcgcc    120

accgccgagc tgctgagctt cctgcccagc gacttcttcc ccagcgtgag agacctgctg    180

gacaccgcca gcgccctgta cagagaggcc ctggagagcc ccgagcactg cagcccccac    240
```

```
cacaccgccc tgagacaggc catcctgtgc tggggcgagc tgatgaccct ggccacctgg    300

gtgggcgtga acctggagga ccccgccagc agagacctgg tggtgagcta cgtgaacacc    360

aacatgggcc tgaagttcag acagctgctg tggttccaca tcagctgcct gaccttcggc    420

agagagaccg tgatcgagta cctggtgagc ttcggcgtgt ggatcagaac cccccccgcc    480

tacagacccc ccaacgcccc catcctgagc accctgcccg agaccaccgt ggtgagaaga    540

agaggcagaa gccccagaag aagaaccccc agccccagaa gaagaagaag ccagagcccc    600

agaagaagaa gaagccagag cagagagagc cagtgctag                           639


<210> SEQ ID NO 15
<211> LENGTH: 386
<212> TYPE: PRT
<213> ORGANISM: Artificial Sequence
<220> FEATURE:
<223> OTHER INFORMATION: Codon optimized Ovalbumin

<400> SEQUENCE: 15

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
```

```
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385


<210> SEQ ID NO 16
<211> LENGTH: 1161
<212> TYPE: DNA
<213> ORGANISM: Artificial Sequence
<220> FEATURE:
<223> OTHER INFORMATION: Codon optimized Ovalbumin

<400> SEQUENCE: 16

atgggcagca tcggcgccgc cagcatggag ttctgcttcg acgtgttcaa ggagctgaag     60

gtgcaccacg ccaacgagaa catcttctac tgccccatcg ccatcatgag cgccctggcc    120

atggtgtacc tgggcgccaa ggacagcacc cgcacccaga tcaacaaggt ggtgcgcttc    180

gacaagctgc ccggcttcgg cgacagcatc gaggcccagt gcggcaccag cgtgaacgtg    240

cacagcagcc tgcgcgacat cctgaaccag atcaccaagc ccaacgacgt gtacagcttc    300

agcctggcca gccgcctgta cgccgaggag cgctacccca tcctgcccga gtacctgcag    360

tgcgtgaagg agctgtaccg cggcggcctg gagcccatca acttccagac cgccgccgac    420

caggcccgcg agctgatcaa cagctgggtg gagagccaga ccaacggcat catccgcaac    480

gtgctgcagc ccagcagcgt ggacagccag accgccatgg tgctggtgaa cgccatcgtg    540

ttcaagggcc tgtgggagaa ggccttcaag gacgaggaca cccaggccat gcccttccgc    600

gtgaccgagc aggagagcaa gcccgtgcag atgatgtacc agatcggcct gttccgcgtg    660

gccagcatgg ccagcgagaa gatgaagatc ctggagctgc ccttcgccag cggcaccatg    720

agcatgctgg tgctgctgcc cgacgaggtg agcggcctgg agcagctgga gagcatcatc    780

aacttcgaga agctgaccga gtggaccagc agcaacgtga tggaggagcg caagatcaag    840

gtgtacctgc cccgcatgaa gatggaggag aagtacaacc tgaccagcgt gctgatggcc    900

atgggcatca ccgacgtgtt cagcagcagc gccaacctga gcggcatcag cagcgccgag    960

agcctgaaga tcagccaggc cgtgcacgcc gcccacgccg agatcaacga ggccggccgc   1020

gaggtggtgg gcagcgccga ggccggcgtg gacgccgcca gcgtgagcga ggagttccgc   1080

gccgaccacc ccttcctgtt ctgcatcaag cacatcgcca ccaacgccgt gctgttcttc   1140

ggccgctgcg tgagccccta a                                             1161


<210> SEQ ID NO 17
<211> LENGTH: 160
<212> TYPE: PRT
<213> ORGANISM: Artificial Sequence
<220> FEATURE:
<223> OTHER INFORMATION: Codon optimized BetvI (Birch)

<400> SEQUENCE: 17
```

```
Met Gly Val Phe Asn Tyr Glu Thr Glu Thr Thr Ser Val Ile Pro Ala
 1               5                  10                  15

Ala Arg Leu Phe Lys Ala Phe Ile Leu Asp Gly Asp Asn Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160


<210> SEQ ID NO 18
<211> LENGTH: 483
<212> TYPE: DNA
<213> ORGANISM: Artificial Sequence
<220> FEATURE:
<223> OTHER INFORMATION: Codon optimized BetvI (Birch)

<400> SEQUENCE: 18

atgggcgtct tcaattacga aaccgagaca actagtgtga tcccagctgc acgccttttt      60

aaggccttca ttcttgatgg agacaacctt gtgccaaagg tggctcccca agctattagt     120

agcgtcgaaa acatcgaggg aaatggcgga ccgggaacca tcaaaaagat caactttccg     180

gagggcttcc ctttcaagta cgttaaggac agggttgatg aagttgatca tacaaatttt     240

aagtacaact actccgtgat cgagggcggc cccgttggag atactctgga aaagatcagc     300

aacgagatta agatcgtggc tacacccgat ggcgggtgtg tgcttaagat ctccaacaaa     360

tatcatacca aagggaacca cgaggttaag gctgaacagg tgaaggcatc aaaggagatg     420

ggagagaccc tcctccgagc ggtggagtct tacttgctcg cacacagcga tgcttacaat     480

tag                                                                   483


<210> SEQ ID NO 19
<211> LENGTH: 262
<212> TYPE: PRT
<213> ORGANISM: Artificial Sequence
<220> FEATURE:
<223> OTHER INFORMATION: Codon optimized Stork HBcAg

<400> SEQUENCE: 19

Met Asp Val Asn Ala Ser Arg Ala Leu Ala Asn Val Tyr Asp Leu Pro
 1               5                  10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60
```

-continued

```
Gln Gly Met Ser Gln Ile Ala Asp Ala Leu Arg Ala Val Ile Pro Pro
65                  70                  75                  80

Thr Thr Thr Pro Val Pro Asp Gly Tyr Leu Ile Ser His Asn Glu Ala
                85                  90                  95

Gln Glu Leu Pro Leu Asn Asp Leu Phe Val Leu Gln Glu Glu Arg Ile
            100                 105                 110

Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ser Asn
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Ser Arg Asn Gln Thr Lys Gly Val Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Gly Arg Arg Ser Ser Pro Ser
225                 230                 235                 240

Gln Arg Ala Gly Ser Pro Ile Pro Arg Asn Arg Glu Asn Gln Ser Arg
                245                 250                 255

Ser Ser Ser Pro Arg Glu
            260
```

<210> SEQ ID NO 20
<211> LENGTH: 789
<212> TYPE: DNA
<213> ORGANISM: Artificial Sequence
<220> FEATURE:
<223> OTHER INFORMATION: Codon optimized Stork HBcAg

<400> SEQUENCE: 20

```
atggacgtga acgccagcag agccctggcc aacgtgtacg acctgcccga cgacttcttc      60

ccccagatcg acgacctggt gagagacgcc aaggacgccc tggagcccta ctggaaggcc     120

gagaccatca agaagcacgt gctgatcgcc acccacttcg tggacttgat cgaggacttc     180

tggcagacca cccagggcat gagccagatc gccgacgccc tgagagccgt gatccccccc     240

accaccaccc ccgtgcccga cggctacctg atcagccaca acgaggccca ggagctcccc     300

ctgaacgacc tgttcgtgct gcaggaggag agaatcgtga acttccagcc cgactacccc     360

atcaccgcca gaattcacac ccacctgaga gtgtacacca agctgaacga gcaggccctg     420

gacaaggcca gaagactgct gtggtggcac tacaactgcc tgctgtgggg cgagagcaac     480

gtgaccaact acatcagcag actgagaacc tggctgagca cccccgagaa gtacagaggc     540

aaggacgccc ccaccatcga ggccatcacc agacccatcc aggtggccca gggcagcaga     600

aaccagacca agggcgtgag aaagcccaga ggcctggagc ccagaagaag aaaggtgaag     660

accaccgtgg tgtacggcag aagaagaagc aagagcagag gcagaagaag cagccccagc     720

cagagagccg gcagccccat ccccagaaac agagagaacc agagcagaag cagcagcccc     780

agagagtga                                                             789
```

<210> SEQ ID NO 21
<211> LENGTH: 262

<212> TYPE: PRT
<213> ORGANISM: Artificial Sequence
<220> FEATURE:
<223> OTHER INFORMATION: Codon optimized Heron HBcAg

<400> SEQUENCE: 21

```
Met Asp Val Asn Ala Ser Arg Ala Leu Ala Asn Val Tyr Asp Leu Pro
 1               5                  10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Val Pro Val Pro Glu Gly Phe Leu Ile Thr His Ser Glu Ala
                85                  90                  95

Glu Glu Leu Pro Leu Asn Asp Leu Phe Ser Leu Gln Glu Glu Arg Ile
            100                 105                 110

Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Gly Arg Asn Gln Thr Lys Gly Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Gly Arg Arg Ser Ser Pro Ser
225                 230                 235                 240

Gln Arg Ala Gly Ser Pro Leu Pro Arg Asn Arg Gly Asn Gln Thr Arg
                245                 250                 255

Ser Pro Ser Pro Arg Glu
            260
```

<210> SEQ ID NO 22
<211> LENGTH: 789
<212> TYPE: DNA
<213> ORGANISM: Artificial Sequence
<220> FEATURE:
<223> OTHER INFORMATION: Codon optimized Heron HBcAg

<400> SEQUENCE: 22

```
atggacgtga acgccagcag agccctggcc aacgtgtacg acctgcccga cgacttcttc     60

ccccagatcg acgacctggt gagagacgcc aaggacgccc tggagcccta ctggaaggcc    120

gagaccatca agaagcacgt gctgatcgcc acccacttcg tggacttgat cgaggacttc    180

tggcagacca cccagggcat gagccagatc gccgacgccc tgagagccgt gatccccccc    240

accaccgtgc ccgtgcccga gggcttcctg atcacccaca gcgaggccga ggagctcccc    300

ctgaacgacc tgttcagtct gcaggaggag agaatcgtga acttccagcc cgactacccc    360
```

```
atcaccgcca gaattcacac ccacctgaga gtgtacacca agctgaacga gcaggccctg    420

gacaaggcca gaagactgct gtggtggcac tacaactgcc tgctgtgggg cgaggccacc    480

gtgaccaact acatcagcag actgagaacc tggctgagca cccccgagaa gtacagaggc    540

aaggacgccc ccaccatcga ggccatcacc agacccatcc aggtggccca gggcggcaga    600

aaccagacca agggcaccag aaagcccaga ggcctggagc ccagaagaag aaaggtgaag    660

accaccgtgg tgtacggcag aagaagaagc aagagcagag gcagaagaag cagcccccagc    720

cagagagccg gcagcccccct gcccagaaac agaggcaacc agaccagaag ccccagcccc    780

agagagtga                                                            789
```

<210> SEQ ID NO 23
<211> LENGTH: 948
<212> TYPE: PRT
<213> ORGANISM: Artificial Sequence
<220> FEATURE:
<223> OTHER INFORMATION: Codon optimized HCV NS3/4A-Stork core

<400> SEQUENCE: 23

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285
```

-continued

```
Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Val Asn Ala Ser Arg Ala Leu Ala Asn Val Tyr Asp Leu Pro Asp Asp
    690                 695                 700

Phe Phe Pro Gln Ile Asp Asp Leu Val Arg Asp Ala Lys Asp Ala Leu
705                 710                 715                 720
```

```
Glu Pro Tyr Trp Lys Ala Glu Thr Ile Lys Lys His Val Leu Ile Ala
                725                 730                 735

Thr His Phe Val Asp Leu Ile Glu Asp Phe Trp Gln Thr Thr Gln Gly
            740                 745                 750

Met Ser Gln Ile Ala Asp Ala Leu Arg Ala Val Ile Pro Pro Thr Thr
        755                 760                 765

Thr Pro Val Pro Asp Gly Tyr Leu Ile Ser His Asn Glu Ala Gln Glu
    770                 775                 780

Leu Pro Leu Asn Asp Leu Phe Val Leu Gln Glu Glu Arg Ile Val Asn
785                 790                 795                 800

Phe Gln Pro Asp Tyr Pro Ile Thr Ala Arg Ile His Thr His Leu Arg
                805                 810                 815

Val Tyr Thr Lys Leu Asn Glu Gln Ala Leu Asp Lys Ala Arg Arg Leu
            820                 825                 830

Leu Trp Trp His Tyr Asn Cys Leu Leu Trp Gly Glu Ser Asn Val Thr
        835                 840                 845

Asn Tyr Ile Ser Arg Leu Arg Thr Trp Leu Ser Thr Pro Glu Lys Tyr
    850                 855                 860

Arg Gly Lys Asp Ala Pro Thr Ile Glu Ala Ile Thr Arg Pro Ile Gln
865                 870                 875                 880

Val Ala Gln Gly Ser Arg Asn Gln Thr Lys Gly Val Arg Lys Pro Arg
                885                 890                 895

Gly Leu Glu Pro Arg Arg Arg Lys Val Lys Thr Thr Val Val Tyr Gly
            900                 905                 910

Arg Arg Arg Ser Lys Ser Arg Gly Arg Arg Ser Ser Pro Ser Gln Arg
        915                 920                 925

Ala Gly Ser Pro Ile Pro Arg Asn Arg Glu Asn Gln Ser Arg Ser Ser
    930                 935                 940

Ser Pro Arg Glu
945
```

<210> SEQ ID NO 24
<211> LENGTH: 2847
<212> TYPE: DNA
<213> ORGANISM: Artificial Sequence
<220> FEATURE:
<223> OTHER INFORMATION: Codon optimized HCV NS3/4A-Stork HBcAg

<400> SEQUENCE: 24

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720
```

-continued

```
gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg  1800

taccgcctgg gcgccgtgca gaacgaggtg accctgaccc accccgtgac caagtacatc   1860

atgacctgca tgagcgccga cctggaggtg gtgaccccca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacgtgaac gccagcagag ccctggccaa cgtgtacgac   2100

ctgcccgacg acttcttccc ccagatcgac gacctggtga gagacgccaa ggacgccctg   2160

gagccctact ggaaggccga gaccatcaag aagcacgtgc tgatcgccac ccacttcgtg   2220

gacttgatcg aggacttctg gcagaccacc cagggcatga gccagatcgc cgacgccctg   2280

agagccgtga tcccccccac caccaccccc gtgcccgacg gctacctgat cagccacaac   2340

gaggcccagg agctccccct gaacgacctg ttcgtgctgc aggaggagag aatcgtgaac   2400

ttccagcccg actaccccat caccgccaga attcacaccc acctgagagt gtacaccaag   2460

ctgaacgagc aggccctgga caaggccaga agactgctgt ggtggcacta caactgcctg   2520

ctgtggggcg agagcaacgt gaccaactac atcagcagac tgagaacctg gctgagcacc   2580

cccgagaagt acagaggcaa ggacgccccc accatcgagg ccatcaccag acccatccag   2640

gtggcccagg gcagcagaaa ccagaccaag ggcgtgagaa agcccagagg cctggagccc   2700

agaagaagaa aggtgaagac caccgtggtg tacggcagaa gaagaagcaa gagcagaggc   2760

agaagaagca gccccagcca gagagccggc agccccatcc ccagaaacag agagaaccag   2820

agcagaagca gcagccccag agagtga                                       2847
```

<210> SEQ ID NO 25
<211> LENGTH: 948
<212> TYPE: PRT
<213> ORGANISM: Artificial Sequence
<220> FEATURE:
<223> OTHER INFORMATION: Codon optimized mutant NS3/4A-Stork HBcAg -continued

<400> SEQUENCE: 25

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr Ala Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Ala Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415
```

```
Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Val Asn Ala Ser Arg Ala Leu Ala Asn Val Tyr Asp Leu Pro Asp Asp
    690                 695                 700

Phe Phe Pro Gln Ile Asp Asp Leu Val Arg Asp Ala Lys Asp Ala Leu
705                 710                 715                 720

Glu Pro Tyr Trp Lys Ala Glu Thr Ile Lys Lys His Val Leu Ile Ala
                725                 730                 735

Thr His Phe Val Asp Leu Ile Glu Asp Phe Trp Gln Thr Thr Gln Gly
            740                 745                 750

Met Ser Gln Ile Ala Asp Ala Leu Arg Ala Val Ile Pro Pro Thr Thr
        755                 760                 765

Thr Pro Val Pro Asp Gly Tyr Leu Ile Ser His Asn Glu Ala Gln Glu
    770                 775                 780

Leu Pro Leu Asn Asp Leu Phe Val Leu Gln Glu Glu Arg Ile Val Asn
785                 790                 795                 800

Phe Gln Pro Asp Tyr Pro Ile Thr Ala Arg Ile His Thr His Leu Arg
                805                 810                 815

Val Tyr Thr Lys Leu Asn Glu Gln Ala Leu Asp Lys Ala Arg Arg Leu
            820                 825                 830

Leu Trp Trp His Tyr Asn Cys Leu Leu Trp Gly Glu Ser Asn Val Thr
        835                 840                 845
```

```
Asn Tyr Ile Ser Arg Leu Arg Thr Trp Leu Ser Thr Pro Glu Lys Tyr
    850                 855                 860

Arg Gly Lys Asp Ala Pro Thr Ile Glu Ala Ile Thr Arg Pro Ile Gln
865                 870                 875                 880

Val Ala Gln Gly Ser Arg Asn Gln Thr Lys Gly Val Arg Lys Pro Arg
                885                 890                 895

Gly Leu Glu Pro Arg Arg Arg Lys Val Lys Thr Thr Val Val Tyr Gly
            900                 905                 910

Arg Arg Arg Ser Lys Ser Arg Gly Arg Arg Ser Ser Pro Ser Gln Arg
        915                 920                 925

Ala Gly Ser Pro Ile Pro Arg Asn Arg Glu Asn Gln Ser Arg Ser Ser
    930                 935                 940

Ser Pro Arg Glu
945


<210> SEQ ID NO 26
<211> LENGTH: 2847
<212> TYPE: DNA
<213> ORGANISM: Artificial Sequence
<220> FEATURE:
<223> OTHER INFORMATION: Codon optimized mutant NS3/4A-Stork HBcAg

<400> SEQUENCE: 26

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta cgccggcgcc    180

ggcacccgca ccatcgccag ccccaagggc cccgtgatcc agatgtacac caacgtggac    240

caggccctgg tgggctggcc cgcccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440
```

-continued gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800 taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcat ggacgtgaac gccagcagag ccctggccaa cgtgtacgac 2100
ctgcccgacg acttcttccc ccagatcgac gacctggtga gagacgccaa ggacgccctg 2160
gagccctact ggaaggccga gaccatcaag aagcacgtgc tgatcgccac ccacttcgtg 2220
gacttgatcg aggacttctg gcagaccacc cagggcatga gccagatcgc cgacgccctg 2280
agagccgtga tccccccac caccaccccc gtgcccgacg gctacctgat cagccacaac 2340
gaggcccagg agctcccccct gaacgacctg ttcgtgctgc aggaggagag aatcgtgaac 2400
ttccagcccg actaccccat caccgccaga attcacaccc acctgagagt gtacaccaag 2460
ctgaacgagc aggccctgga caaggccaga agactgctgt ggtggcacta caactgcctg 2520
ctgtggggcg agagcaacgt gaccaactac atcagcagac tgagaacctg gctgagcacc 2580
cccgagaagt acagaggcaa ggacgccccc accatcgagg ccatcaccag acccatccag 2640
gtggcccagg gcagcagaaa ccagaccaag ggcgtgagaa agcccagagg cctggagccc 2700
agaagaagaa aggtgaagac caccgtggtg tacggcagaa gaagaagcaa gagcagaggc 2760
agaagaagca gccccagcca gagagccggc agccccatcc ccagaaacag agagaaccag 2820
agcagaagca gcagccccag agagtga 2847

<210> SEQ ID NO 27
<211> LENGTH: 948
<212> TYPE: PRT
<213> ORGANISM: Artificial Sequence
<220> FEATURE:
<223> OTHER INFORMATION: Codon optimized NS3/4A-Stork HBcAg

<400> SEQUENCE: 27

Met Ala Pro Ile Thr Ala Tyr Ala Gln Gln Thr Arg Gly Leu Leu Gly
1 5 10 15

Cys Ile Ile Thr Ser Leu Thr Gly Arg Asp Lys Asn Gln Val Glu Gly
20 25 30

Glu Val Gln Ile Val Ser Thr Ala Ala Gln Thr Phe Leu Ala Thr Cys
35 40 45

Ile Asn Gly Val Cys Trp Thr Val Tyr His Gly Ala Gly Thr Arg Thr
50 55 60

Ile Ala Ser Pro Lys Gly Pro Val Ile Gln Met Tyr Thr Asn Val Asp
65 70 75 80

Gln Asp Leu Val Gly Trp Pro Ala Pro Gln Gly Ala Arg Ser Leu Thr
85 90 95

Pro Cys Thr Cys Gly Ser Ser Asp Leu Tyr Leu Val Thr Arg His Ala
100 105 110

Asp Val Ile Pro Val Arg Arg Arg Gly Asp Gly Arg Gly Ser Leu Leu

-continued

```
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540
```

-continued

```
Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Val Asn Ala Ser Arg Ala Leu Ala Asn Val Tyr Asp Leu Pro Asp Asp
    690                 695                 700

Phe Phe Pro Gln Ile Asp Asp Leu Val Arg Asp Ala Lys Asp Ala Leu
705                 710                 715                 720

Glu Pro Tyr Trp Lys Ala Glu Thr Ile Lys Lys His Val Leu Ile Ala
                725                 730                 735

Thr His Phe Val Asp Leu Ile Glu Asp Phe Trp Gln Thr Thr Gln Gly
            740                 745                 750

Met Ser Gln Ile Ala Asp Ala Leu Arg Ala Val Ile Pro Pro Thr Thr
        755                 760                 765

Thr Pro Val Pro Asp Gly Tyr Leu Ile Ser His Asn Glu Ala Gln Glu
    770                 775                 780

Leu Pro Leu Asn Asp Leu Phe Val Leu Gln Glu Glu Arg Ile Val Asn
785                 790                 795                 800

Phe Gln Pro Asp Tyr Pro Ile Thr Ala Arg Ile His Thr His Leu Arg
                805                 810                 815

Val Tyr Thr Lys Leu Asn Glu Gln Ala Leu Asp Lys Ala Arg Arg Leu
            820                 825                 830

Leu Trp Trp His Tyr Asn Cys Leu Leu Trp Gly Glu Ser Asn Val Thr
        835                 840                 845

Asn Tyr Ile Ser Arg Leu Arg Thr Trp Leu Ser Thr Pro Glu Lys Tyr
    850                 855                 860

Arg Gly Lys Asp Ala Pro Thr Ile Glu Ala Ile Thr Arg Pro Ile Gln
865                 870                 875                 880

Val Ala Gln Gly Ser Arg Asn Gln Thr Lys Gly Val Arg Lys Pro Arg
                885                 890                 895

Gly Leu Glu Pro Arg Arg Arg Lys Val Lys Thr Thr Val Val Tyr Gly
            900                 905                 910

Arg Arg Arg Ser Lys Ser Arg Gly Arg Arg Ser Ser Pro Ser Gln Arg
        915                 920                 925

Ala Gly Ser Pro Ile Pro Arg Asn Arg Glu Asn Gln Ser Arg Ser Ser
    930                 935                 940

Ser Pro Arg Glu
945
```

<210> SEQ ID NO 28

<211> LENGTH: 2847
<212> TYPE: DNA
<213> ORGANISM: Artificial Sequence
<220> FEATURE:
<223> OTHER INFORMATION: Codon optimized NS3/4A-Stork HBcAg
<400> SEQUENCE: 28
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta ccacggcgcc 180
ggcacccgca ccatcgccag ccccaagggc cccgtgatcc agatgtacac caacgtggac 240
caggacctgg tgggctggcc cgccccccag ggcgcccgca gcctgacccc ctgcacctgc 300
ggcagcagcg acctgtacct ggtgacccgc cacgccgacg tgatccccgt gcgccgccgc 360
ggcgacggcc gcggcagcct gctgagcccc cgccccatca gctacctgaa gggcagcagc 420
ggcggccccc tgctgtgccc cgccggccac gccgtgggca tcttccgcgc cgccgtgtgc 480
acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccaccccccc cggcagcgtg accgtgcccc accccaacat cgaggaggtg 1020
gccctgagca ccaccggcga gatccccttc tacggcaagg ccatccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggcccccggc 1440
gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800 taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcat ggacgtgaac gccagcagag ccctggccaa cgtgtacgac 2100
ctgcccgacg acttcttccc ccagatcgac gacctggtga gagacgccaa ggacgccctg 2160

```
gagccctact ggaaggccga gaccatcaag aagcacgtgc tgatcgccac ccacttcgtg   2220

gacttgatcg aggacttctg gcagaccacc cagggcatga gccagatcgc cgacgccctg   2280

agagccgtga tcccccccac caccaccccc gtgcccgacg gctacctgat cagccacaac   2340

gaggcccagg agctccccct gaacgacctg ttcgtgctgc aggaggagag aatcgtgaac   2400

ttccagcccg actaccccat caccgccaga attcacaccc acctgagagt gtacaccaag   2460

ctgaacgagc aggccctgga caaggccaga agactgctgt ggtggcacta caactgcctg   2520

ctgtggggcg agagcaacgt gaccaactac atcagcagac tgagaacctg gctgagcacc   2580

cccgagaagt acagaggcaa ggacgccccc accatcgagg ccatcaccag acccatccag   2640

gtggcccagg gcagcagaaa ccagaccaag ggcgtgagaa agcccagagg cctggagccc   2700

agaagaagaa aggtgaagac caccgtggtg tacggcagaa gaagaagcaa gagcagaggc   2760

agaagaagca gccccagcca gagagccggc agccccatcc ccagaaacag agagaaccag   2820

agcagaagca gcagccccag agagtga                                       2847
```

<210> SEQ ID NO 29
<211> LENGTH: 958
<212> TYPE: PRT
<213> ORGANISM: Artificial Sequence
<220> FEATURE:
<223> OTHER INFORMATION: Codon optimized NS3/4A-4Bjunct-Stork HBcAg

<400> SEQUENCE: 29

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
```

```
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670
```

-continued

```
Arg Glu Val Leu Tyr Arg Glu Phe Asp Glu Met Glu Glu Cys Ser Gln
        675                 680                 685

His Leu Pro Tyr Ile Glu Gln Gly Met Asp Val Asn Ala Ser Arg Ala
    690                 695                 700

Leu Ala Asn Val Tyr Asp Leu Pro Asp Asp Phe Phe Pro Gln Ile Asp
705                 710                 715                 720

Asp Leu Val Arg Asp Ala Lys Asp Ala Leu Glu Pro Tyr Trp Lys Ala
                725                 730                 735

Glu Thr Ile Lys Lys His Val Leu Ile Ala Thr His Phe Val Asp Leu
            740                 745                 750

Ile Glu Asp Phe Trp Gln Thr Thr Gln Gly Met Ser Gln Ile Ala Asp
        755                 760                 765

Ala Leu Arg Ala Val Ile Pro Pro Thr Thr Thr Pro Val Pro Asp Gly
    770                 775                 780

Tyr Leu Ile Ser His Asn Glu Ala Gln Glu Leu Pro Leu Asn Asp Leu
785                 790                 795                 800

Phe Val Leu Gln Glu Glu Arg Ile Val Asn Phe Gln Pro Asp Tyr Pro
                805                 810                 815

Ile Thr Ala Arg Ile His Thr His Leu Arg Val Tyr Thr Lys Leu Asn
            820                 825                 830

Glu Gln Ala Leu Asp Lys Ala Arg Arg Leu Leu Trp Trp His Tyr Asn
        835                 840                 845

Cys Leu Leu Trp Gly Glu Ser Asn Val Thr Asn Tyr Ile Ser Arg Leu
    850                 855                 860

Arg Thr Trp Leu Ser Thr Pro Glu Lys Tyr Arg Gly Lys Asp Ala Pro
865                 870                 875                 880

Thr Ile Glu Ala Ile Thr Arg Pro Ile Gln Val Ala Gln Gly Ser Arg
                885                 890                 895

Asn Gln Thr Lys Gly Val Arg Lys Pro Arg Gly Leu Glu Pro Arg Arg
            900                 905                 910

Arg Lys Val Lys Thr Thr Val Val Tyr Gly Arg Arg Arg Ser Lys Ser
        915                 920                 925

Arg Gly Arg Arg Ser Ser Pro Ser Gln Arg Ala Gly Ser Pro Ile Pro
    930                 935                 940

Arg Asn Arg Glu Asn Gln Ser Arg Ser Ser Ser Pro Arg Glu
945                 950                 955
```

<210> SEQ ID NO 30
<211> LENGTH: 2877
<212> TYPE: DNA
<213> ORGANISM: Artificial Sequence
<220> FEATURE:
<223> OTHER INFORMATION: Codon optimized NS3/4A-4Bjunct-Stork HBcAg

<400> SEQUENCE: 30

```
atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgcccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480
```

-continued

```
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcat ggacgtgaac   2100
gccagcagag ccctggccaa cgtgtacgac ctgcccgacg acttcttccc ccagatcgac   2160
gacctggtga gagacgccaa ggacgccctg gagccctact ggaaggccga gaccatcaag   2220
aagcacgtgc tgatcgccac ccacttcgtg gacttgatcg aggacttctg gcagaccacc   2280
cagggcatga gccagatcgc cgacgccctg agagccgtga tcccccccac caccaccccc   2340
gtgcccgacg gctacctgat cagccacaac gaggcccagg agctccccct gaacgacctg   2400
ttcgtgctgc aggaggagag aatcgtgaac ttccagcccg actaccccat caccgccaga   2460
attcacaccc acctgagagt gtacaccaag ctgaacgagc aggccctgga caaggccaga   2520
agactgctgt ggtggcacta caactgcctg ctgtggggcg agagcaacgt gaccaactac   2580
atcagcagac tgagaacctg gctgagcacc cccgagaagt acagaggcaa ggacgccccc   2640
accatcgagg ccatcaccag acccatccag gtggcccagg gcagcagaaa ccagaccaag   2700
ggcgtgagaa agcccagagg cctggagccc agaagaagaa aggtgaagac caccgtggtg   2760
tacggcagaa gaagaagcaa gagcagaggc agaagaagca gccccagcca gagagccggc   2820
agccccatcc ccagaaacag agagaaccag agcagaagca gcagccccag agagtga      2877
```

<210> SEQ ID NO 31
<211> LENGTH: 948
<212> TYPE: PRT
<213> ORGANISM: Artificial Sequence
<220> FEATURE:
<223> OTHER INFORMATION: Codon optimized HCV NS3/4A-Heron HBcAg

<400> SEQUENCE: 31

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
```

-continued

```
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Val Asn Ala Ser Arg Ala Leu Ala Asn Val Tyr Asp Leu Pro Asp Asp
    690                 695                 700

Phe Phe Pro Gln Ile Asp Asp Leu Val Arg Asp Ala Lys Asp Ala Leu
705                 710                 715                 720

Glu Pro Tyr Trp Lys Ala Glu Thr Ile Lys Lys His Val Leu Ile Ala
                725                 730                 735

Thr His Phe Val Asp Leu Ile Glu Asp Phe Trp Gln Thr Thr Gln Gly
            740                 745                 750

Met Ser Gln Ile Ala Asp Ala Leu Arg Ala Val Ile Pro Pro Thr Thr
        755                 760                 765

Val Pro Val Pro Glu Gly Phe Leu Ile Thr His Ser Glu Ala Glu Glu
    770                 775                 780

Leu Pro Leu Asn Asp Leu Phe Ser Leu Gln Glu Glu Arg Ile Val Asn
785                 790                 795                 800
```

-continued

```
Phe Gln Pro Asp Tyr Pro Ile Thr Ala Arg Ile His Thr His Leu Arg
                805                 810                 815

Val Tyr Thr Lys Leu Asn Glu Gln Ala Leu Asp Lys Ala Arg Arg Leu
            820                 825                 830

Leu Trp Trp His Tyr Asn Cys Leu Leu Trp Gly Glu Ala Thr Val Thr
        835                 840                 845

Asn Tyr Ile Ser Arg Leu Arg Thr Trp Leu Ser Thr Pro Glu Lys Tyr
    850                 855                 860

Arg Gly Lys Asp Ala Pro Thr Ile Glu Ala Ile Thr Arg Pro Ile Gln
865                 870                 875                 880

Val Ala Gln Gly Gly Arg Asn Gln Thr Lys Gly Thr Arg Lys Pro Arg
                885                 890                 895

Gly Leu Glu Pro Arg Arg Arg Lys Val Lys Thr Thr Val Val Tyr Gly
            900                 905                 910

Arg Arg Arg Ser Lys Ser Arg Gly Arg Arg Ser Ser Pro Ser Gln Arg
        915                 920                 925

Ala Gly Ser Pro Leu Pro Arg Asn Arg Gly Asn Gln Thr Arg Ser Pro
    930                 935                 940

Ser Pro Arg Glu
945
```

<210> SEQ ID NO 32
<211> LENGTH: 2847
<212> TYPE: DNA
<213> ORGANISM: Artificial Sequence
<220> FEATURE:
<223> OTHER INFORMATION: Codon optimized HCV NS3/4A-Heron HBcAg

<400> SEQUENCE: 32

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatcccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200
```

-continued

```
atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac ccccctgctg   1800

taccgcctgg gcgccgtgca gaacgaggtg accctgaccc accccgtgac caagtacatc   1860

atgacctgca tgagcgccga cctggaggtg gtgaccccca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacgtgaac gccagcagag ccctggccaa cgtgtacgac   2100

ctgcccgacg acttcttccc ccagatcgac gacctggtga gagacgccaa ggacgccctg   2160

gagccctact ggaaggccga gaccatcaag aagcacgtgc tgatcgccac ccacttcgtg   2220

gacttgatcg aggacttctg gcagaccacc cagggcatga gccagatcgc cgacgccctg   2280

agagccgtga tccccccccac caccgtgccc gtgcccgagg gcttcctgat cacccacagc   2340

gaggccgagg agctcccccct gaacgacctg ttcagtctgc aggaggagag aatcgtgaac   2400

ttccagcccg actaccccat caccgccaga attcacaccc acctgagagt gtacaccaag   2460

ctgaacgagc aggccctgga caaggccaga agactgctgt ggtggcacta caactgcctg   2520

ctgtggggcg aggccaccgt gaccaactac atcagcagac tgagaacctg gctgagcacc   2580

cccgagaagt acagaggcaa ggacgccccc accatcgagg ccatcaccag acccatccag   2640

gtggcccagg gcggcagaaa ccagaccaag ggcaccagaa agcccagagg cctggagccc   2700

agaagaagaa aggtgaagac caccgtggtg tacggcagaa gaagaagcaa gagcagaggc   2760

agaagaagca gccccagcca gagagccggc agccccctgc ccagaaacag aggcaaccag   2820

accagaagcc ccagccccag agagtga                                       2847
```

<210> SEQ ID NO 33
<211> LENGTH: 948
<212> TYPE: PRT
<213> ORGANISM: Artificial Sequence
<220> FEATURE:
<223> OTHER INFORMATION: Codon optimized mutant NS3/4A-Heron HBcAg

<400> SEQUENCE: 33

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr Ala Gly Ala Gly Thr Arg Thr
    50                  55                  60

Ile Ala Ser Pro Lys Gly Pro Val Ile Gln Met Tyr Thr Asn Val Asp
65                  70                  75                  80
```

-continued

```
Gln Ala Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
```

```
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Val Asn Ala Ser Arg Ala Leu Ala Asn Val Tyr Asp Leu Pro Asp Asp
    690                 695                 700

Phe Phe Pro Gln Ile Asp Asp Leu Val Arg Asp Ala Lys Asp Ala Leu
705                 710                 715                 720

Glu Pro Tyr Trp Lys Ala Glu Thr Ile Lys Lys His Val Leu Ile Ala
                725                 730                 735

Thr His Phe Val Asp Leu Ile Glu Asp Phe Trp Gln Thr Thr Gln Gly
            740                 745                 750

Met Ser Gln Ile Ala Asp Ala Leu Arg Ala Val Ile Pro Pro Thr Thr
        755                 760                 765

Val Pro Val Pro Glu Gly Phe Leu Ile Thr His Ser Glu Ala Glu Glu
    770                 775                 780

Leu Pro Leu Asn Asp Leu Phe Ser Leu Gln Glu Glu Arg Ile Val Asn
785                 790                 795                 800

Phe Gln Pro Asp Tyr Pro Ile Thr Ala Arg Ile His Thr His Leu Arg
                805                 810                 815

Val Tyr Thr Lys Leu Asn Glu Gln Ala Leu Asp Lys Ala Arg Arg Leu
            820                 825                 830

Leu Trp Trp His Tyr Asn Cys Leu Leu Trp Gly Glu Ala Thr Val Thr
        835                 840                 845

Asn Tyr Ile Ser Arg Leu Arg Thr Trp Leu Ser Thr Pro Glu Lys Tyr
    850                 855                 860

Arg Gly Lys Asp Ala Pro Thr Ile Glu Ala Ile Thr Arg Pro Ile Gln
865                 870                 875                 880

Val Ala Gln Gly Gly Arg Asn Gln Thr Lys Gly Thr Arg Lys Pro Arg
                885                 890                 895

Gly Leu Glu Pro Arg Arg Arg Lys Val Lys Thr Thr Val Val Tyr Gly
            900                 905                 910

Arg Arg Arg Ser Lys Ser Arg Gly Arg Arg Ser Ser Pro Ser Gln Arg
        915                 920                 925
```

-continued

```
Ala Gly Ser Pro Leu Pro Arg Asn Arg Gly Asn Gln Thr Arg Ser Pro
    930                 935                 940

Ser Pro Arg Glu
945
```

<210> SEQ ID NO 34
<211> LENGTH: 2847
<212> TYPE: DNA
<213> ORGANISM: Artificial Sequence
<220> FEATURE:
<223> OTHER INFORMATION: Codon optimized mutant NS3/4A-Heron HBcAg

<400> SEQUENCE: 34

```
atggccccca tcaccgccta cgcccagcag acccgcggcc tgctgggctg catcatcacc     60
agcctgaccg gccgcgacaa gaaccaggtg gagggcgagg tgcagatcgt gagcaccgcc    120
gcccagacct tcctggccac ctgcatcaac ggcgtgtgct ggaccgtgta cgccggcgcc    180
ggcacccgca ccatcgccag ccccaagggc cccgtgatcc agatgtacac caacgtggac    240
caggccctgg tgggctggcc cgccccccag ggcgcccgca gcctgacccc ctgcacctgc    300
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatcccct ggaggccatc    1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac ccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
```

-continued

```
gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacgtgaac gccagcagag ccctggccaa cgtgtacgac   2100

ctgcccgacg acttcttccc ccagatcgac gacctggtga gagacgccaa ggacgccctg   2160

gagccctact ggaaggccga gaccatcaag aagcacgtgc tgatcgccac ccacttcgtg   2220

gacttgatcg aggacttctg gcagaccacc cagggcatga gccagatcgc cgacgccctg   2280

agagccgtga tccccccac caccgtgccc gtgcccgagg gcttcctgat cacccacagc   2340

gaggccgagg agctccccct gaacgacctg ttcagtctgc aggaggagag aatcgtgaac   2400

ttccagcccg actaccccat caccgccaga attcacaccc acctgagagt gtacaccaag   2460

ctgaacgagc aggccctgga caaggccaga agactgctgt ggtggcacta caactgcctg   2520

ctgtggggcg aggccaccgt gaccaactac atcagcagac tgagaacctg gctgagcacc   2580

cccgagaagt acagaggcaa ggacgccccc accatcgagg ccatcaccag acccatccag   2640

gtggcccagg gcggcagaaa ccagaccaag ggcaccagaa agcccagagg cctggagccc   2700

agaagaagaa aggtgaagac caccgtggtg tacggcagaa gaagaagcaa gagcagaggc   2760

agaagaagca gccccagcca gagagccggc agccccctgc ccagaaacag aggcaaccag   2820

accagaagcc ccagccccag agagtga                                       2847
```

<210> SEQ ID NO 35
<211> LENGTH: 948
<212> TYPE: PRT
<213> ORGANISM: Artificial Sequence
<220> FEATURE:
<223> OTHER INFORMATION: Codon optimized NS3/4A-Heron HBcAg

<400> SEQUENCE: 35

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205
```

```
Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
```

625 630 635 640

Val Leu Ala Ala Leu Ala Ala Tyr Cys Leu Ser Thr Gly Cys Val Val
645 650 655

Ile Val Gly Arg Ile Val Leu Ser Gly Lys Pro Ala Ile Ile Pro Asp
660 665 670

Arg Glu Val Leu Tyr Arg Glu Phe Asp Glu Met Glu Glu Cys Met Asp
675 680 685

Val Asn Ala Ser Arg Ala Leu Ala Asn Val Tyr Asp Leu Pro Asp Asp
690 695 700

Phe Phe Pro Gln Ile Asp Asp Leu Val Arg Asp Ala Lys Asp Ala Leu
705 710 715 720

Glu Pro Tyr Trp Lys Ala Glu Thr Ile Lys Lys His Val Leu Ile Ala
725 730 735

Thr His Phe Val Asp Leu Ile Glu Asp Phe Trp Gln Thr Thr Gln Gly
740 745 750

Met Ser Gln Ile Ala Asp Ala Leu Arg Ala Val Ile Pro Pro Thr Thr
755 760 765

Val Pro Val Pro Glu Gly Phe Leu Ile Thr His Ser Glu Ala Glu Glu
770 775 780

Leu Pro Leu Asn Asp Leu Phe Ser Leu Gln Glu Glu Arg Ile Val Asn
785 790 795 800

Phe Gln Pro Asp Tyr Pro Ile Thr Ala Arg Ile His Thr His Leu Arg
805 810 815

Val Tyr Thr Lys Leu Asn Glu Gln Ala Leu Asp Lys Ala Arg Arg Leu
820 825 830

Leu Trp Trp His Tyr Asn Cys Leu Leu Trp Gly Glu Ala Thr Val Thr
835 840 845

Asn Tyr Ile Ser Arg Leu Arg Thr Trp Leu Ser Thr Pro Glu Lys Tyr
850 855 860

Arg Gly Lys Asp Ala Pro Thr Ile Glu Ala Ile Thr Arg Pro Ile Gln
865 870 875 880

Val Ala Gln Gly Gly Arg Asn Gln Thr Lys Gly Thr Arg Lys Pro Arg
885 890 895

Gly Leu Glu Pro Arg Arg Arg Lys Val Lys Thr Thr Val Val Tyr Gly
900 905 910

Arg Arg Arg Ser Lys Ser Arg Gly Arg Arg Ser Ser Pro Ser Gln Arg
915 920 925

Ala Gly Ser Pro Leu Pro Arg Asn Arg Gly Asn Gln Thr Arg Ser Pro
930 935 940

Ser Pro Arg Glu
945

<210> SEQ ID NO 36
<211> LENGTH: 2847
<212> TYPE: DNA
<213> ORGANISM: Artificial Sequence
<220> FEATURE:
<223> OTHER INFORMATION: Codon optimized NS3/4A-Heron HBcAg

<400> SEQUENCE: 36
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta ccacggcgcc 180
ggcacccgca ccatcgccag ccccaagggc cccgtgatcc agatgtacac caacgtggac 240

-continued

```
caggacctgg tgggctggcc cgccccccag ggcgcccgca gcctgacccc ctgcacctgc    300
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccacccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcat ggacgtgaac gccagcagag ccctggccaa cgtgtacgac   2100
ctgcccgacg acttcttccc ccagatcgac gacctggtga gagacgccaa ggacgccctg   2160
gagccctact ggaaggccga gaccatcaag aagcacgtgc tgatcgccac ccacttcgtg   2220
gacttgatcg aggacttctg gcagaccacc cagggcatga gccagatcgc cgacgccctg   2280
agagccgtga tcccccccac caccgtgccc gtgcccgagg gcttcctgat cacccacagc   2340
gaggccgagg agctcccccct gaacgacctg ttcagtctgc aggaggagag aatcgtgaac   2400
ttccagcccg actaccccat caccgccaga attcacaccc acctgagagt gtacaccaag   2460
ctgaacgagc aggccctgga caaggccaga agactgctgt ggtggcacta caactgcctg   2520
ctgtggggcg aggccaccgt gaccaactac atcagcagac tgagaacctg gctgagcacc   2580
cccgagaagt acagaggcaa ggacgccccc accatcgagg ccatcaccag acccatccag   2640
```

-continued

```
gtggcccagg gcggcagaaa ccagaccaag ggcaccagaa agcccagagg cctggagccc   2700

agaagaagaa aggtgaagac caccgtggtg tacggcagaa gaagaagcaa gagcagaggc   2760

agaagaagca gccccagcca gagagccggc agccccctgc ccagaaacag aggcaaccag   2820

accagaagcc ccagccccag agagtga                                       2847


<210> SEQ ID NO 37
<211> LENGTH: 958
<212> TYPE: PRT
<213> ORGANISM: Artificial Sequence
<220> FEATURE:
<223> OTHER INFORMATION: Codon optimized NS3/4A-4B junct-Heron HBcAg

<400> SEQUENCE: 37

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335
```

```
Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Val Asn Ala Ser Arg Ala
    690                 695                 700

Leu Ala Asn Val Tyr Asp Leu Pro Asp Asp Phe Phe Pro Gln Ile Asp
705                 710                 715                 720

Asp Leu Val Arg Asp Ala Lys Asp Ala Leu Glu Pro Tyr Trp Lys Ala
                725                 730                 735

Glu Thr Ile Lys Lys His Val Leu Ile Ala Thr His Phe Val Asp Leu
            740                 745                 750

Ile Glu Asp Phe Trp Gln Thr Thr Gln Gly Met Ser Gln Ile Ala Asp
```

-continued

```
        755                 760                 765

Ala Leu Arg Ala Val Ile Pro Pro Thr Thr Val Pro Val Pro Glu Gly
    770                 775                 780

Phe Leu Ile Thr His Ser Glu Ala Glu Glu Leu Pro Leu Asn Asp Leu
785                 790                 795                 800

Phe Ser Leu Gln Glu Glu Arg Ile Val Asn Phe Gln Pro Asp Tyr Pro
                805                 810                 815

Ile Thr Ala Arg Ile His Thr His Leu Arg Val Tyr Thr Lys Leu Asn
            820                 825                 830

Glu Gln Ala Leu Asp Lys Ala Arg Arg Leu Leu Trp Trp His Tyr Asn
        835                 840                 845

Cys Leu Leu Trp Gly Glu Ala Thr Val Thr Asn Tyr Ile Ser Arg Leu
    850                 855                 860

Arg Thr Trp Leu Ser Thr Pro Glu Lys Tyr Arg Gly Lys Asp Ala Pro
865                 870                 875                 880

Thr Ile Glu Ala Ile Thr Arg Pro Ile Gln Val Ala Gln Gly Gly Arg
                885                 890                 895

Asn Gln Thr Lys Gly Thr Arg Lys Pro Arg Gly Leu Glu Pro Arg Arg
            900                 905                 910

Arg Lys Val Lys Thr Thr Val Val Tyr Gly Arg Arg Arg Ser Lys Ser
        915                 920                 925

Arg Gly Arg Arg Ser Ser Pro Ser Gln Arg Ala Gly Ser Pro Leu Pro
    930                 935                 940

Arg Asn Arg Gly Asn Gln Thr Arg Ser Pro Ser Pro Arg Glu
945                 950                 955
```

<210> SEQ ID NO 38
<211> LENGTH: 2877
<212> TYPE: DNA
<213> ORGANISM: Artificial Sequence
<220> FEATURE:
<223> OTHER INFORMATION: Codon optimized NS3/4A-4B junct-Heron HBcAg

<400> SEQUENCE: 38

```
atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgccccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480

acccgcggcg tggccaaggc cgtggacttc atccccgtgg agagcctgga gaccaccatg     540

cgcagccccg tgttcagcga caacagcagc ccccccgccg tgccccagag ctaccaggtg     600

gcccacctgc acgcccccac cggcagcggc aagagcacca aggtgcccgc cgcctacgcc     660

gcccagggct acaaggtgct ggtgctgaac cccagcgtgg ccgccaccat gggcttcggc     720

gcctacatga gcaaggccca cggcatcgac cccaacatcc gcaccggcgt gcgcaccatc     780

accaccggca gccccatcac ctacagcacc tacggcaagt tcctggccga cggcggctgc     840

agcggcggcg cctacgacat catcatctgc gacgagtgcc acagcaccga cgccaccagc     900

atcctgggca tcggcaccgt gctggaccag gccgagaccg ccggcgcccg cctgaccgtg     960
```

```
ctggccaccg ccaccccccc cggcagcgtg accgtgcccc accccaacat cgaggaggtg   1020

gccctgagca ccaccggcga gatccccttc tacggcaagg ccatcccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcat ggacgtgaac   2100

gccagcagag ccctggccaa cgtgtacgac ctgcccgacg acttcttccc ccagatcgac   2160

gacctggtga gagacgccaa ggacgccctg gagccctact ggaaggccga gaccatcaag   2220

aagcacgtgc tgatcgccac ccacttcgtg gacttgatcg aggacttctg gcagaccacc   2280

cagggcatga gccagatcgc cgacgccctg agagccgtga tcccccccac caccgtgccc   2340

gtgcccgagg gcttcctgat cacccacagc gaggccgagg agctcccccct gaacgacctg   2400

ttcagtctgc aggaggagag aatcgtgaac ttccagcccg actaccccat caccgccaga   2460

attcacaccc acctgagagt gtacaccaag ctgaacgagc aggccctgga caaggccaga   2520

agactgctgt ggtggcacta caactgcctg ctgtggggcg aggccaccgt gaccaactac   2580

atcagcagac tgagaacctg gctgagcacc cccgagaagt acagaggcaa ggacgccccc   2640

accatcgagg ccatcaccag acccatccag gtggcccagg gcggcagaaa ccagaccaag   2700

ggcaccagaa agcccagagg cctggagccc agaagaagaa aggtgaagac caccgtggtg   2760

tacggcagaa gaagaagcaa gagcagaggc agaagaagca gccccagcca gagagccggc   2820

agccccctgc ccagaaacag aggcaaccag accagaagcc ccagccccag agagtga      2877
```

<210> SEQ ID NO 39
<211> LENGTH: 711
<212> TYPE: PRT
<213> ORGANISM: Artificial Sequence
<220> FEATURE:
<223> OTHER INFORMATION: Codon optimized HCV NS5A-Stork HBcAg

<400> SEQUENCE: 39

```
Met Gly Ser Gly Ser Trp Leu Arg Asp Val Trp Asp Trp Ile Cys Thr
 1               5                  10                  15

Val Leu Thr Asp Phe Lys Thr Trp Leu Gln Ser Lys Leu Leu Pro Lys
            20                  25                  30
```

```
Leu Pro Gly Val Pro Phe Phe Ser Cys Gln Arg Gly Tyr Lys Gly Val
        35                  40                  45

Trp Arg Gly Asp Gly Ile Met Gln Thr Thr Cys Pro Cys Gly Ala Gln
    50                  55                  60

Ile Thr Gly His Val Lys Asn Gly Ser Met Arg Ile Val Gly Pro Lys
65                  70                  75                  80

Thr Cys Ser Asn Thr Trp His Gly Thr Phe Pro Ile Asn Ala Tyr Thr
                85                  90                  95

Thr Gly Pro Cys Thr Pro Ser Pro Ala Pro Asn Tyr Ser Arg Ala Leu
            100                 105                 110

Trp Arg Val Ala Ala Glu Glu Tyr Val Glu Ile Thr Arg Val Gly Asp
        115                 120                 125

Phe His Tyr Val Thr Gly Met Thr Thr Asp Asn Val Lys Cys Pro Cys
    130                 135                 140

Gln Val Pro Ala Pro Glu Phe Phe Thr Glu Leu Asp Gly Val Arg Leu
145                 150                 155                 160

His Arg Tyr Ala Pro Ala Cys Arg Pro Leu Leu Arg Glu Asp Val Thr
                165                 170                 175

Phe Gln Val Gly Leu Asn Gln Tyr Leu Val Gly Ser Gln Leu Pro Cys
            180                 185                 190

Glu Pro Glu Pro Asp Val Ala Val Leu Thr Ser Met Leu Thr Asp Pro
        195                 200                 205

Ser His Ile Thr Ala Glu Thr Ala Lys Arg Arg Leu Ala Arg Gly Ser
    210                 215                 220

Pro Pro Ser Leu Ala Ser Ser Ser Ala Ser Gln Leu Ser Ala Pro Ser
225                 230                 235                 240

Leu Lys Ala Thr Cys Thr Thr His His Asp Ser Pro Asp Ala Asp Leu
                245                 250                 255

Ile Glu Ala Asn Leu Leu Trp Arg Gln Glu Met Gly Gly Asn Ile Thr
            260                 265                 270

Arg Val Glu Ser Glu Asn Lys Val Val Ile Leu Asp Ser Phe Asp Pro
        275                 280                 285

Leu Arg Ala Glu Glu Asp Glu Arg Glu Val Ser Val Ala Ala Glu Ile
    290                 295                 300

Leu Arg Lys Ser Lys Lys Phe Pro Pro Ala Leu Pro Ile Trp Ala Arg
305                 310                 315                 320

Pro Asp Tyr Asn Pro Pro Leu Leu Glu Ser Trp Lys Ser Pro Asp Tyr
                325                 330                 335

Val Pro Pro Ala Val His Gly Cys Pro Leu Pro Pro Thr Thr Gly Pro
            340                 345                 350

Pro Ile Pro Pro Pro Arg Lys Lys Arg Thr Val Val Leu Thr Glu Ser
        355                 360                 365

Thr Val Ser Ser Ala Leu Ala Glu Leu Ala Thr Lys Thr Phe Gly Ser
    370                 375                 380

Ser Gly Ser Ser Ala Val Asp Ser Gly Thr Ala Thr Ala Pro Pro Asp
385                 390                 395                 400

Gln Thr Ser Asp Asp Gly Asp Lys Glu Ser Asp Ile Glu Ser Tyr Ser
                405                 410                 415

Ser Met Pro Pro Leu Glu Gly Glu Pro Gly Asp Pro Asp Leu Ser Asp
            420                 425                 430

Gly Ser Trp Ser Thr Val Ser Gly Glu Ala Gly Asp Asp Ile Val Cys
        435                 440                 445

Cys Met Asp Val Asn Ala Ser Arg Ala Leu Ala Asn Val Tyr Asp Leu
    450                 455                 460
```

```
Pro Asp Asp Phe Phe Pro Gln Ile Asp Asp Leu Val Arg Asp Ala Lys
465                 470                 475                 480

Asp Ala Leu Glu Pro Tyr Trp Lys Ala Glu Thr Ile Lys Lys His Val
                485                 490                 495

Leu Ile Ala Thr His Phe Val Asp Leu Ile Glu Asp Phe Trp Gln Thr
            500                 505                 510

Thr Gln Gly Met Ser Gln Ile Ala Asp Ala Leu Arg Ala Val Ile Pro
        515                 520                 525

Pro Thr Thr Thr Pro Val Pro Asp Gly Tyr Leu Ile Ser His Asn Glu
    530                 535                 540

Ala Gln Glu Leu Pro Leu Asn Asp Leu Phe Val Leu Gln Glu Glu Arg
545                 550                 555                 560

Ile Val Asn Phe Gln Pro Asp Tyr Pro Ile Thr Ala Arg Ile His Thr
                565                 570                 575

His Leu Arg Val Tyr Thr Lys Leu Asn Glu Gln Ala Leu Asp Lys Ala
            580                 585                 590

Arg Arg Leu Leu Trp Trp His Tyr Asn Cys Leu Leu Trp Gly Glu Ser
        595                 600                 605

Asn Val Thr Asn Tyr Ile Ser Arg Leu Arg Thr Trp Leu Ser Thr Pro
    610                 615                 620

Glu Lys Tyr Arg Gly Lys Asp Ala Pro Thr Ile Glu Ala Ile Thr Arg
625                 630                 635                 640

Pro Ile Gln Val Ala Gln Gly Ser Arg Asn Gln Thr Lys Gly Val Arg
                645                 650                 655

Lys Pro Arg Gly Leu Glu Pro Arg Arg Arg Lys Val Lys Thr Thr Val
            660                 665                 670

Val Tyr Gly Arg Arg Arg Ser Lys Ser Arg Gly Arg Arg Ser Ser Pro
        675                 680                 685

Ser Gln Arg Ala Gly Ser Pro Ile Pro Arg Asn Arg Glu Asn Gln Ser
    690                 695                 700

Arg Ser Ser Ser Pro Arg Glu
705                 710
```

<210> SEQ ID NO 40
<211> LENGTH: 2136
<212> TYPE: DNA
<213> ORGANISM: Artificial Sequence
<220> FEATURE:
<223> OTHER INFORMATION: Codon optimized HCV NS5A-Stork HBcAg

<400> SEQUENCE: 40

```
atgggatctg gaagctggct gagggatgtt tgggattgga tttgtaccgt cctcaccgac      60

ttcaaaacct ggctccagtc caagctgctg ccaaagctgc ccggagtgcc attcttctcc     120

tgtcagaggg gctataaagg cgtgtggagg ggcgatggaa ttatgcagac tacttgcccc     180

tgtggagctc aaattactgg gcacgttaag aatggctcca tgcggattgt tggcccaaaa     240

acctgttcca acacctggca cggaaccttc cctattaacg cttacaccac cggaccttgc     300

actccttccc ccgcacctaa ttattcccgg gctctctggc gggtggcagc agaggaatat     360

gtcgaaatta ccagagtcgg cgacttccac tacgtcacag gaatgactac agacaacgtt     420

aaatgtccct gccaagtgcc cgctccagag ttctttaccg aactcgacgg ggttaggctc     480

cacagatacg cacccgcctg ccggccactg ctgcgggaag acgtcacatt ccaggtcggg     540

ctgaaccagt acctggtggg ctctcagctg ccttgtgagc ctgagcccga cgtggcagtt     600

ctcaccagca tgctcaccga tcctagccac atcaccgctg agacagccaa acgccgcctg     660
```

```
gctagagggt cccctccctc tctggccagc tccagcgcta gccagctctc cgcaccaagc    720

ctgaaagcca catgcactac acaccacgat agccccgacg cagacctgat tgaagccaac    780

ctcctctgga gacaggaaat gggcggaaac atcactaggg tcgaatccga gaataaagtg    840

gttattctgg atagcttcga cccactcagg gcagaggaag atgagagaga ggttagcgtg    900

gccgctgaga ttctccgcaa gtccaaaaag ttccctcccg cactgcccat ttggcaagg     960

cccgattaca atcctccact gctcgagagc tggaagtccc ctgactacgt gccaccagcc   1020

gtccacggat gccctctgcc ccctaccaca ggaccaccaa ttccaccccc tagaaagaaa   1080

cggaccgtgg ttctgactga gtccaccgtg tcctctgcac tcgctgagct ggcaaccaag   1140

acctttggat ccagcggatc ctccgcagtc gactccggca ccgctaccgc cccacccgat   1200

caaacctctg acgatggaga caaggagagc gatattgagt cctattccag catgccccca   1260

ctcgagggag aacccggcga ccccgacctg agcgatgggt cctggagcac tgtgagcggg   1320

gaagcagggg acgacattgt ctgttgcatg gacgtgaacg ccagcagagc cctggccaac   1380

gtgtacgacc tgcccgacga cttcttcccc cagatcgacg acctggtgag agacgccaag   1440

gacgccctgg agccctactg gaaggccgag accatcaaga agcacgtgct gatcgccacc   1500

cacttcgtgg acttgatcga ggacttctgg cagaccaccc agggcatgag ccagatcgcc   1560

gacgccctga gagccgtgat cccccccacc accacccccg tgcccgacgg ctacctgatc   1620

agccacaacg aggcccagga gctccccctg aacgacctgt tcgtgctgca ggaggagaga   1680

atcgtgaact tccagcccga ctaccccatc accgccagaa ttcacaccca cctgagagtg   1740

tacaccaagc tgaacgagca ggccctggac aaggccagaa gactgctgtg gtggcactac   1800

aactgcctgc tgtggggcga gagcaacgtg accaactaca tcagcagact gagaacctgg   1860

ctgagcaccc ccgagaagta cagaggcaag gacgccccca ccatcgaggc catcaccaga   1920

cccatccagg tggcccaggg cagcagaaac cagaccaagg gcgtgagaaa gcccagaggc   1980

ctggagccca gaagaagaaa ggtgaagacc accgtggtgt acggcagaag aagaagcaag   2040

agcagaggca gaagaagcag ccccagccag agagccggca gccccatccc cagaaacaga   2100

gagaaccaga gcagaagcag cagccccaga gagtga                              2136
```

<210> SEQ ID NO 41
<211> LENGTH: 711
<212> TYPE: PRT
<213> ORGANISM: Artificial Sequence
<220> FEATURE:
<223> OTHER INFORMATION: Codon optimized HCV NS5A-Heron HBcAg

<400> SEQUENCE: 41

```
Met Gly Ser Gly Ser Trp Leu Arg Asp Val Trp Asp Trp Ile Cys Thr
 1               5                  10                  15

Val Leu Thr Asp Phe Lys Thr Trp Leu Gln Ser Lys Leu Leu Pro Lys
            20                  25                  30

Leu Pro Gly Val Pro Phe Phe Ser Cys Gln Arg Gly Tyr Lys Gly Val
        35                  40                  45

Trp Arg Gly Asp Gly Ile Met Gln Thr Thr Cys Pro Cys Gly Ala Gln
    50                  55                  60

Ile Thr Gly His Val Lys Asn Gly Ser Met Arg Ile Val Gly Pro Lys
65                  70                  75                  80

Thr Cys Ser Asn Thr Trp His Gly Thr Phe Pro Ile Asn Ala Tyr Thr
                85                  90                  95

Thr Gly Pro Cys Thr Pro Ser Pro Ala Pro Asn Tyr Ser Arg Ala Leu
```

```
            100                 105                 110

Trp Arg Val Ala Ala Glu Glu Tyr Val Glu Ile Thr Arg Val Gly Asp
        115                 120                 125

Phe His Tyr Val Thr Gly Met Thr Thr Asp Asn Val Lys Cys Pro Cys
    130                 135                 140

Gln Val Pro Ala Pro Glu Phe Phe Thr Glu Leu Asp Gly Val Arg Leu
145                 150                 155                 160

His Arg Tyr Ala Pro Ala Cys Arg Pro Leu Leu Arg Glu Asp Val Thr
                165                 170                 175

Phe Gln Val Gly Leu Asn Gln Tyr Leu Val Gly Ser Gln Leu Pro Cys
            180                 185                 190

Glu Pro Glu Pro Asp Val Ala Val Leu Thr Ser Met Leu Thr Asp Pro
        195                 200                 205

Ser His Ile Thr Ala Glu Thr Ala Lys Arg Arg Leu Ala Arg Gly Ser
    210                 215                 220

Pro Pro Ser Leu Ala Ser Ser Ser Ala Ser Gln Leu Ser Ala Pro Ser
225                 230                 235                 240

Leu Lys Ala Thr Cys Thr Thr His His Asp Ser Pro Asp Ala Asp Leu
                245                 250                 255

Ile Glu Ala Asn Leu Leu Trp Arg Gln Glu Met Gly Gly Asn Ile Thr
            260                 265                 270

Arg Val Glu Ser Glu Asn Lys Val Val Ile Leu Asp Ser Phe Asp Pro
        275                 280                 285

Leu Arg Ala Glu Glu Asp Glu Arg Glu Val Ser Val Ala Ala Glu Ile
    290                 295                 300

Leu Arg Lys Ser Lys Lys Phe Pro Pro Ala Leu Pro Ile Trp Ala Arg
305                 310                 315                 320

Pro Asp Tyr Asn Pro Pro Leu Leu Glu Ser Trp Lys Ser Pro Asp Tyr
                325                 330                 335

Val Pro Pro Ala Val His Gly Cys Pro Leu Pro Pro Thr Thr Gly Pro
            340                 345                 350

Pro Ile Pro Pro Pro Arg Lys Lys Arg Thr Val Val Leu Thr Glu Ser
        355                 360                 365

Thr Val Ser Ser Ala Leu Ala Glu Leu Ala Thr Lys Thr Phe Gly Ser
    370                 375                 380

Ser Gly Ser Ser Ala Val Asp Ser Gly Thr Ala Thr Ala Pro Pro Asp
385                 390                 395                 400

Gln Thr Ser Asp Asp Gly Asp Lys Glu Ser Asp Ile Glu Ser Tyr Ser
                405                 410                 415

Ser Met Pro Pro Leu Glu Gly Glu Pro Gly Asp Pro Asp Leu Ser Asp
            420                 425                 430

Gly Ser Trp Ser Thr Val Ser Gly Glu Ala Gly Asp Asp Ile Val Cys
        435                 440                 445

Cys Met Asp Val Asn Ala Ser Arg Ala Leu Ala Asn Val Tyr Asp Leu
    450                 455                 460

Pro Asp Asp Phe Phe Pro Gln Ile Asp Asp Leu Val Arg Asp Ala Lys
465                 470                 475                 480

Asp Ala Leu Glu Pro Tyr Trp Lys Ala Glu Thr Ile Lys Lys His Val
                485                 490                 495

Leu Ile Ala Thr His Phe Val Asp Leu Ile Glu Asp Phe Trp Gln Thr
            500                 505                 510

Thr Gln Gly Met Ser Gln Ile Ala Asp Ala Leu Arg Ala Val Ile Pro
        515                 520                 525
```

-continued

```
Pro Thr Thr Val Pro Val Pro Glu Gly Phe Leu Ile Thr His Ser Glu
    530                 535                 540

Ala Glu Glu Leu Pro Leu Asn Asp Leu Phe Ser Leu Gln Glu Glu Arg
545                 550                 555                 560

Ile Val Asn Phe Gln Pro Asp Tyr Pro Ile Thr Ala Arg Ile His Thr
                565                 570                 575

His Leu Arg Val Tyr Thr Lys Leu Asn Glu Gln Ala Leu Asp Lys Ala
            580                 585                 590

Arg Arg Leu Leu Trp Trp His Tyr Asn Cys Leu Leu Trp Gly Glu Ala
        595                 600                 605

Thr Val Thr Asn Tyr Ile Ser Arg Leu Arg Thr Trp Leu Ser Thr Pro
    610                 615                 620

Glu Lys Tyr Arg Gly Lys Asp Ala Pro Thr Ile Glu Ala Ile Thr Arg
625                 630                 635                 640

Pro Ile Gln Val Ala Gln Gly Gly Arg Asn Gln Thr Lys Gly Thr Arg
                645                 650                 655

Lys Pro Arg Gly Leu Glu Pro Arg Arg Arg Lys Val Lys Thr Thr Val
            660                 665                 670

Val Tyr Gly Arg Arg Arg Ser Lys Ser Arg Gly Arg Arg Ser Ser Pro
        675                 680                 685

Ser Gln Arg Ala Gly Ser Pro Leu Pro Arg Asn Arg Gly Asn Gln Thr
    690                 695                 700

Arg Ser Pro Ser Pro Arg Glu
705                 710
```

<210> SEQ ID NO 42
<211> LENGTH: 2136
<212> TYPE: DNA
<213> ORGANISM: Artificial Sequence
<220> FEATURE:
<223> OTHER INFORMATION: Codon optimized HCV NS5A-Heron HBcAg

<400> SEQUENCE: 42

```
atgggatctg gaagctggct gagggatgtt tgggattgga tttgtaccgt cctcaccgac     60

ttcaaaacct ggctccagtc caagctgctg ccaaagctgc ccggagtgcc attcttctcc    120

tgtcagaggg gctataaagg cgtgtggagg ggcgatggaa ttatgcagac tacttgcccc    180

tgtggagctc aaattactgg gcacgttaag aatggctcca tgcggattgt tggcccaaaa    240

acctgttcca acacctggca cggaaccttc cctattaacg cttacaccac cggaccttgc    300

actccttccc ccgcacctaa ttattcccgg gctctctggc gggtggcagc agaggaatat    360

gtcgaaatta ccagagtcgg cgacttccac tacgtcacag gaatgactac agacaacgtt    420

aaatgtccct gccaagtgcc cgctccagag ttctttaccg aactcgacgg ggttaggctc    480

cacagatacg cacccgcctg ccggccactg ctgcgggaag acgtcacatt ccaggtcggg    540

ctgaaccagt acctggtggg ctctcagctg ccttgtgagc ctgagcccga cgtggcagtt    600

ctcaccagca tgctcaccga tcctagccac atcaccgctg agacagccaa acgccgcctg    660

gctagagggt cccctccctc tctggccagc tccagcgcta gccagctctc cgcaccaagc    720

ctgaaagcca catgcactac acaccacgat agccccgacg cagacctgat tgaagccaac    780

ctcctctgga gacaggaaat gggcggaaac atcactaggg tcgaatccga gaataaagtg    840

gttattctgg atagcttcga cccactcagg gcagaggaag atgagagaga ggttagcgtg    900

gccgctgaga ttctccgcaa gtccaaaaag ttccctcccg cactgcccat ttgggcaagg    960

cccgattaca atcctccact gctcgagagc tggaagtccc ctgactacgt gccaccagcc   1020
```

-continued

```
gtccacggat gccctctgcc ccctaccaca ggaccaccaa ttccaccccc tagaaagaaa   1080

cggaccgtgg ttctgactga gtccaccgtg tcctctgcac tcgctgagct ggcaaccaag   1140

acctttggat ccagcggatc ctccgcagtc gactccggca ccgctaccgc cccacccgat   1200

caaacctctg acgatggaga caaggagagc gatattgagt cctattccag catgccccca   1260

ctcgagggag aacccggcga ccccgacctg agcgatgggt cctggagcac tgtgagcggg   1320

gaagcagggg acgacattgt ctgttgcatg gacgtgaacg ccagcagagc cctggccaac   1380

gtgtacgacc tgcccgacga cttcttcccc cagatcgacg acctggtgag agacgccaag   1440

gacgccctgg agccctactg gaaggccgag accatcaaga agcacgtgct gatcgccacc   1500

cacttcgtgg acttgatcga ggacttctgg cagaccaccc agggcatgag ccagatcgcc   1560

gacgccctga gagccgtgat ccccccacc accgtgcccg tgcccgaggg cttcctgatc   1620

acccacagcg aggccgagga gctccccctg aacgacctgt tcagtctgca ggaggagaga   1680

atcgtgaact tccagcccga ctaccccatc accgccagaa ttcacaccca cctgagagtg   1740

tacaccaagc tgaacgagca ggccctggac aaggccagaa gactgctgtg gtggcactac   1800

aactgcctgc tgtggggcga ggccaccgtg accaactaca tcagcagact gagaacctgg   1860

ctgagcaccc ccgagaagta cagaggcaag gacgccccca ccatcgaggc catcaccaga   1920

cccatccagg tggcccaggg cggcagaaac cagaccaagg gcaccagaaa gcccagaggc   1980

ctggagccca gaagaagaaa ggtgaagacc accgtggtgt acggcagaag aagaagcaag   2040

agcagaggca gaagaagcag ccccagccag agagccggca gccccctgcc cagaaacaga   2100

ggcaaccaga ccagaagccc cagccccaga gagtga                             2136
```

<210> SEQ ID NO 43
<211> LENGTH: 474
<212> TYPE: PRT
<213> ORGANISM: Artificial Sequence
<220> FEATURE:
<223> OTHER INFORMATION: Codon optimized HBV HBeAg-Stork HBcAg

<400> SEQUENCE: 43

```
Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

```
Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys Met Asp Val Asn Ala Ser Arg Ala Leu Ala Asn Val
    210                 215                 220

Tyr Asp Leu Pro Asp Asp Phe Phe Pro Gln Ile Asp Asp Leu Val Arg
225                 230                 235                 240

Asp Ala Lys Asp Ala Leu Glu Pro Tyr Trp Lys Ala Glu Thr Ile Lys
                245                 250                 255

Lys His Val Leu Ile Ala Thr His Phe Val Asp Leu Ile Glu Asp Phe
            260                 265                 270

Trp Gln Thr Thr Gln Gly Met Ser Gln Ile Ala Asp Ala Leu Arg Ala
        275                 280                 285

Val Ile Pro Pro Thr Thr Thr Pro Val Pro Asp Gly Tyr Leu Ile Ser
    290                 295                 300

His Asn Glu Ala Gln Glu Leu Pro Leu Asn Asp Leu Phe Val Leu Gln
305                 310                 315                 320

Glu Glu Arg Ile Val Asn Phe Gln Pro Asp Tyr Pro Ile Thr Ala Arg
                325                 330                 335

Ile His Thr His Leu Arg Val Tyr Thr Lys Leu Asn Glu Gln Ala Leu
            340                 345                 350

Asp Lys Ala Arg Arg Leu Leu Trp Trp His Tyr Asn Cys Leu Leu Trp
        355                 360                 365

Gly Glu Ser Asn Val Thr Asn Tyr Ile Ser Arg Leu Arg Thr Trp Leu
    370                 375                 380

Ser Thr Pro Glu Lys Tyr Arg Gly Lys Asp Ala Pro Thr Ile Glu Ala
385                 390                 395                 400

Ile Thr Arg Pro Ile Gln Val Ala Gln Gly Ser Arg Asn Gln Thr Lys
                405                 410                 415

Gly Val Arg Lys Pro Arg Gly Leu Glu Pro Arg Arg Arg Lys Val Lys
            420                 425                 430

Thr Thr Val Val Tyr Gly Arg Arg Arg Ser Lys Ser Arg Gly Arg Arg
        435                 440                 445

Ser Ser Pro Ser Gln Arg Ala Gly Ser Pro Ile Pro Arg Asn Arg Glu
    450                 455                 460

Asn Gln Ser Arg Ser Ser Ser Pro Arg Glu
465                 470
```

<210> SEQ ID NO 44
<211> LENGTH: 1425
<212> TYPE: DNA
<213> ORGANISM: Artificial Sequence
<220> FEATURE:
<223> OTHER INFORMATION: Codon optimized HBV HBeAg-Stork HBcAg

<400> SEQUENCE: 44

```
atgcagctgt tccacctgtg cctgatcatc agctgcagct gccccaccgt gcaggccagc      60

aagctgtgcc tgggctggct gtggggcatg gacatcgacc cctacaagga gttcggcgcc     120

accgccgagc tgctgagctt cctgcccagc gacttcttcc ccagcgtgag agacctgctg     180

gacaccgcca gcgccctgta cagagaggcc ctggagagcc ccgagcactg cagcccccac     240

cacaccgccc tgagacaggc catcctgtgc tggggcgagc tgatgaccct ggccacctgg     300

gtgggcgtga acctggagga ccccgccagc agagacctgg tggtgagcta cgtgaacacc     360
```

```
aacatgggcc tgaagttcag acagctgctg tggttccaca tcagctgcct gaccttcggc    420

agagagaccg tgatcgagta cctggtgagc ttcggcgtgt ggatcagaac cccccccgcc    480

tacagacccc ccaacgcccc catcctgagc accctgcccg agaccaccgt ggtgagaaga    540

agaggcagaa gccccagaag aagaaccccc agccccagaa gaagaagaag ccagagcccc    600

agaagaagaa gaagccagag cagagagagc cagtgcatgg acgtgaacgc cagcagagcc    660

ctggccaacg tgtacgacct gcccgacgac ttcttccccc agatcgacga cctggtgaga    720

gacgccaagg acgccctgga gccctactgg aaggccgaga ccatcaagaa gcacgtgctg    780

atcgccaccc acttcgtgga cttgatcgag gacttctggc agaccaccca gggcatgagc    840

cagatcgccg acgccctgag agccgtgatc ccccccacca ccacccccgt gcccgacggc    900

tacctgatca gccacaacga ggcccaggag ctcccccctga acgacctgtt cgtgctgcag    960

gaggagagaa tcgtgaactt ccagcccgac taccccatca ccgccagaat tcacacccac   1020

ctgagagtgt acaccaagct gaacgagcag gccctggaca aggccagaag actgctgtgg   1080

tggcactaca actgcctgct gtggggcgag agcaacgtga ccaactacat cagcagactg   1140

agaacctggc tgagcacccc cgagaagtac agaggcaagg acgcccccac catcgaggcc   1200

atcaccagac ccatccaggt ggcccagggc agcagaaacc agaccaaggg cgtgagaaag   1260

cccagaggcc tggagcccag aagaagaaag gtgaagacca ccgtggtgta cggcagaaga   1320

agaagcaaga gcagaggcag aagaagcagc cccagccaga gagccggcag ccccatcccc   1380

agaaacagag agaaccagag cagaagcagc agccccagag agtga                   1425
```

<210> SEQ ID NO 45
<211> LENGTH: 474
<212> TYPE: PRT
<213> ORGANISM: Artificial Sequence
<220> FEATURE:
<223> OTHER INFORMATION: Codon optimized HBV HBeAg-Stork HBcAg

<400> SEQUENCE: 45

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Leu Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
```

```
            180                 185                 190

Arg Arg Arg Arg Ser Gln Ser Pro Arg Arg Arg Arg Ser Gln Ser Arg
        195                 200                 205

Glu Ser Gln Cys Met Asp Val Asn Ala Ser Arg Ala Leu Ala Asn Val
    210                 215                 220

Tyr Asp Leu Pro Asp Asp Phe Phe Pro Gln Ile Asp Asp Leu Val Arg
225                 230                 235                 240

Asp Ala Lys Asp Ala Leu Glu Pro Tyr Trp Lys Ala Glu Thr Ile Lys
                245                 250                 255

Lys His Val Leu Ile Ala Thr His Phe Val Asp Leu Ile Glu Asp Phe
            260                 265                 270

Trp Gln Thr Thr Gln Gly Met Ser Gln Ile Ala Asp Ala Leu Arg Ala
        275                 280                 285

Val Ile Pro Pro Thr Thr Thr Pro Val Pro Asp Gly Tyr Leu Ile Ser
    290                 295                 300

His Asn Glu Ala Gln Glu Leu Pro Leu Asn Asp Leu Phe Val Leu Gln
305                 310                 315                 320

Glu Glu Arg Ile Val Asn Phe Gln Pro Asp Tyr Pro Ile Thr Ala Arg
                325                 330                 335

Ile His Thr His Leu Arg Val Tyr Thr Lys Leu Asn Glu Gln Ala Leu
            340                 345                 350

Asp Lys Ala Arg Arg Leu Leu Trp Trp His Tyr Asn Cys Leu Leu Trp
        355                 360                 365

Gly Glu Ser Asn Val Thr Asn Tyr Ile Ser Arg Leu Arg Thr Trp Leu
    370                 375                 380

Ser Thr Pro Glu Lys Tyr Arg Gly Lys Asp Ala Pro Thr Ile Glu Ala
385                 390                 395                 400

Ile Thr Arg Pro Ile Gln Val Ala Gln Gly Ser Arg Asn Gln Thr Lys
                405                 410                 415

Gly Val Arg Lys Pro Arg Gly Leu Glu Pro Arg Arg Arg Lys Val Lys
            420                 425                 430

Thr Thr Val Val Tyr Gly Arg Arg Arg Ser Lys Ser Arg Gly Arg Arg
        435                 440                 445

Ser Ser Pro Ser Gln Arg Ala Gly Ser Pro Ile Pro Arg Asn Arg Glu
    450                 455                 460

Asn Gln Ser Arg Ser Ser Ser Pro Arg Glu
465                 470


<210> SEQ ID NO 46
<211> LENGTH: 1425
<212> TYPE: DNA
<213> ORGANISM: Artificial Sequence
<220> FEATURE:
<223> OTHER INFORMATION: Codon optimized HBV HBeAg-Stork HBcAg

<400> SEQUENCE: 46

atgcagctgt tccacctgtg cctgatcatc agctgcagct gccccaccgt gcaggccagc      60

aagctgtgcc tgggctggct gtggggcctg gacatcgacc cctacaagga gttcggcgcc     120

accgccgagc tgctgagctt cctgcccagc gacttcttcc ccagcgtgag agacctgctg     180

gacaccgcca gcgccctgta cagagaggcc ctggagagcc ccgagcactg cagcccccac     240

cacaccgccc tgagacaggc catcctgtgc tggggcgagc tgatgaccct ggccacctgg     300

gtgggcgtga acctggagga ccccgccagc agagacctgg tggtgagcta cgtgaacacc     360

aacatgggcc tgaagttcag acagctgctg tggttccaca tcagctgcct gaccttcggc     420
```

-continued

```
agagagaccg tgatcgagta cctggtgagc ttcggcgtgt ggatcagaac cccccccgcc    480

tacagacccc ccaacgcccc catcctgagc accctgcccg agaccaccgt ggtgagaaga    540

agaggcagaa gccccagaag aagaaccccc agccccagaa gaagaagaag ccagagcccc    600

agaagaagaa gaagccagag cagagagagc cagtgcatgg acgtgaacgc cagcagagcc    660

ctggccaacg tgtacgacct gcccgacgac ttcttccccc agatcgacga cctggtgaga    720

gacgccaagg acgccctgga gccctactgg aaggccgaga ccatcaagaa gcacgtgctg    780

atcgccaccc acttcgtgga cttgatcgag gacttctggc agaccaccca gggcatgagc    840

cagatcgccg acgccctgag agccgtgatc ccccccacca ccacccccgt gcccgacggc    900

tacctgatca gccacaacga ggcccaggag ctcccccctga acgacctgtt cgtgctgcag    960

gaggagagaa tcgtgaactt ccagcccgac taccccatca ccgccagaat tcacacccac   1020

ctgagagtgt acaccaagct gaacgagcag gccctggaca aggccagaag actgctgtgg   1080

tggcactaca actgcctgct gtggggcgag agcaacgtga ccaactacat cagcagactg   1140

agaacctggc tgagcacccc cgagaagtac agaggcaagg acgcccccac catcgaggcc   1200

atcaccagac ccatccaggt ggcccagggc agcagaaacc agaccaaggg cgtgagaaag   1260

cccagaggcc tggagcccag aagaagaaag gtgaagacca ccgtggtgta cggcagaaga   1320

agaagcaaga gcagaggcag aagaagcagc cccagccaga gagccggcag ccccatcccc   1380

agaaacagag agaaccagag cagaagcagc agccccagag agtga                   1425
```

<210> SEQ ID NO 47
<211> LENGTH: 474
<212> TYPE: PRT
<213> ORGANISM: Artificial Sequence
<220> FEATURE:
<223> OTHER INFORMATION: Codon optimized HBV HBeAg-Heron HBcAg

<400> SEQUENCE: 47

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190
```

```
Arg Arg Arg Arg Ser Gln Ser Pro Arg Arg Arg Arg Ser Gln Ser Arg
        195                 200                 205

Glu Ser Gln Cys Met Asp Val Asn Ala Ser Arg Ala Leu Ala Asn Val
    210                 215                 220

Tyr Asp Leu Pro Asp Asp Phe Phe Pro Gln Ile Asp Asp Leu Val Arg
225                 230                 235                 240

Asp Ala Lys Asp Ala Leu Glu Pro Tyr Trp Lys Ala Glu Thr Ile Lys
                245                 250                 255

Lys His Val Leu Ile Ala Thr His Phe Val Asp Leu Ile Glu Asp Phe
            260                 265                 270

Trp Gln Thr Thr Gln Gly Met Ser Gln Ile Ala Asp Ala Leu Arg Ala
        275                 280                 285

Val Ile Pro Pro Thr Thr Val Pro Val Pro Glu Gly Phe Leu Ile Thr
    290                 295                 300

His Ser Glu Ala Glu Glu Leu Pro Leu Asn Asp Leu Phe Ser Leu Gln
305                 310                 315                 320

Glu Glu Arg Ile Val Asn Phe Gln Pro Asp Tyr Pro Ile Thr Ala Arg
                325                 330                 335

Ile His Thr His Leu Arg Val Tyr Thr Lys Leu Asn Glu Gln Ala Leu
            340                 345                 350

Asp Lys Ala Arg Arg Leu Leu Trp Trp His Tyr Asn Cys Leu Leu Trp
        355                 360                 365

Gly Glu Ala Thr Val Thr Asn Tyr Ile Ser Arg Leu Arg Thr Trp Leu
    370                 375                 380

Ser Thr Pro Glu Lys Tyr Arg Gly Lys Asp Ala Pro Thr Ile Glu Ala
385                 390                 395                 400

Ile Thr Arg Pro Ile Gln Val Ala Gln Gly Gly Arg Asn Gln Thr Lys
                405                 410                 415

Gly Thr Arg Lys Pro Arg Gly Leu Glu Pro Arg Arg Arg Lys Val Lys
            420                 425                 430

Thr Thr Val Val Tyr Gly Arg Arg Arg Ser Lys Ser Arg Gly Arg Arg
        435                 440                 445

Ser Ser Pro Ser Gln Arg Ala Gly Ser Pro Leu Pro Arg Asn Arg Gly
    450                 455                 460

Asn Gln Thr Arg Ser Pro Ser Pro Arg Glu
465                 470
```

<210> SEQ ID NO 48
<211> LENGTH: 1425
<212> TYPE: DNA
<213> ORGANISM: Artificial Sequence
<220> FEATURE:
<223> OTHER INFORMATION: Codon optimized HBV HBeAg-Heron HBcAg

<400> SEQUENCE: 48

```
atgcagctgt tccacctgtg cctgatcatc agctgcagct gccccaccgt gcaggccagc      60

aagctgtgcc tgggctggct gtggggcatg gacatcgacc cctacaagga gttcggcgcc     120

accgccgagc tgctgagctt cctgcccagc gacttcttcc ccagcgtgag agacctgctg     180

gacaccgcca gcgccctgta cagagaggcc ctggagagcc ccgagcactg cagcccccac     240

cacaccgccc tgagacaggc catcctgtgc tggggcgagc tgatgaccct ggccacctgg     300

gtgggcgtga acctggagga ccccgccagc agagacctgg tggtgagcta cgtgaacacc     360

aacatgggcc tgaagttcag acagctgctg tggttccaca tcagctgcct gaccttcggc     420

agagagaccg tgatcgagta cctggtgagc ttcggcgtgt ggatcagaac cccccccgcc     480
```

-continued

```
tacagacccc ccaacgcccc catcctgagc accctgcccg agaccaccgt ggtgagaaga    540

agaggcagaa gccccagaag aagaaccccc agccccagaa gaagaagaag ccagagcccc    600

agaagaagaa gaagccagag cagagagagc cagtgcatgg acgtgaacgc cagcagagcc    660

ctggccaacg tgtacgacct gcccgacgac ttcttccccc agatcgacga cctggtgaga    720

gacgccaagg acgccctgga gccctactgg aaggccgaga ccatcaagaa gcacgtgctg    780

atcgccaccc acttcgtgga cttgatcgag gacttctggc agaccaccca gggcatgagc    840

cagatcgccg acgccctgag agccgtgatc ccccccacca ccgtgcccgt gcccgagggc    900

ttcctgatca cccacagcga ggccgaggag ctcccccctga acgacctgtt cagtctgcag    960

gaggagagaa tcgtgaactt ccagcccgac taccccatca ccgccagaat tcacacccac   1020

ctgagagtgt acaccaagct gaacgagcag gccctggaca aggccagaag actgctgtgg   1080

tggcactaca actgcctgct gtggggcgag gccaccgtga ccaactacat cagcagactg   1140

agaacctggc tgagcacccc cgagaagtac agaggcaagg acgcccccac catcgaggcc   1200

atcaccagac ccatccaggt ggcccagggc ggcagaaacc agaccaaggg caccagaaag   1260

cccagaggcc tggagcccag aagaagaaag gtgaagacca ccgtggtgta cggcagaaga   1320

agaagcaaga gcagaggcag aagaagcagc cccagccaga gagccggcag ccccctgccc   1380

agaaacagag gcaaccagac cagaagcccc agccccagag agtga                   1425
```

```
<210> SEQ ID NO 49
<211> LENGTH: 474
<212> TYPE: PRT
<213> ORGANISM: Artificial Sequence
<220> FEATURE:
<223> OTHER INFORMATION: Codon optimized HBV HBeAg-Heron HBcAg

<400> SEQUENCE: 49

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Leu Asp Ile
            20                  25                  30

Asp Pro Tyr Lys Glu Phe Gly Ala Thr Ala Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

```
Glu Ser Gln Cys Met Asp Val Asn Ala Ser Arg Ala Leu Ala Asn Val
    210                 215                 220

Tyr Asp Leu Pro Asp Asp Phe Phe Pro Gln Ile Asp Asp Leu Val Arg
225                 230                 235                 240

Asp Ala Lys Asp Ala Leu Glu Pro Tyr Trp Lys Ala Glu Thr Ile Lys
                245                 250                 255

Lys His Val Leu Ile Ala Thr His Phe Val Asp Leu Ile Glu Asp Phe
            260                 265                 270

Trp Gln Thr Thr Gln Gly Met Ser Gln Ile Ala Asp Ala Leu Arg Ala
        275                 280                 285

Val Ile Pro Pro Thr Thr Val Pro Val Pro Glu Gly Phe Leu Ile Thr
    290                 295                 300

His Ser Glu Ala Glu Glu Leu Pro Leu Asn Asp Leu Phe Ser Leu Gln
305                 310                 315                 320

Glu Glu Arg Ile Val Asn Phe Gln Pro Asp Tyr Pro Ile Thr Ala Arg
                325                 330                 335

Ile His Thr His Leu Arg Val Tyr Thr Lys Leu Asn Glu Gln Ala Leu
            340                 345                 350

Asp Lys Ala Arg Arg Leu Leu Trp Trp His Tyr Asn Cys Leu Leu Trp
        355                 360                 365

Gly Glu Ala Thr Val Thr Asn Tyr Ile Ser Arg Leu Arg Thr Trp Leu
    370                 375                 380

Ser Thr Pro Glu Lys Tyr Arg Gly Lys Asp Ala Pro Thr Ile Glu Ala
385                 390                 395                 400

Ile Thr Arg Pro Ile Gln Val Ala Gln Gly Gly Arg Asn Gln Thr Lys
                405                 410                 415

Gly Thr Arg Lys Pro Arg Gly Leu Glu Pro Arg Arg Arg Lys Val Lys
            420                 425                 430

Thr Thr Val Val Tyr Gly Arg Arg Arg Ser Lys Ser Arg Gly Arg Arg
        435                 440                 445

Ser Ser Pro Ser Gln Arg Ala Gly Ser Pro Leu Pro Arg Asn Arg Gly
    450                 455                 460

Asn Gln Thr Arg Ser Pro Ser Pro Arg Glu
465                 470
```

```
<210> SEQ ID NO 50
<211> LENGTH: 1425
<212> TYPE: DNA
<213> ORGANISM: Artificial Sequence
<220> FEATURE:
<223> OTHER INFORMATION: Codon optimized HBV HBeAg-Heron HBcAg

<400> SEQUENCE: 50

atgcagctgt tccacctgtg cctgatcatc agctgcagct gccccaccgt gcaggccagc      60

aagctgtgcc tgggctggct gtggggcctg gacatcgacc cctacaagga gttcggcgcc     120

accgccgagc tgctgagctt cctgcccagc gacttcttcc ccagcgtgag agacctgctg     180

gacaccgcca gcgccctgta cagagaggcc ctggagagcc ccgagcactg cagcccccac     240

cacaccgccc tgagacaggc catcctgtgc tggggcgagc tgatgaccct ggccacctgg     300

gtgggcgtga acctggagga ccccgccagc agagacctgg tggtgagcta cgtgaacacc     360

aacatgggcc tgaagttcag acagctgctg tggttccaca tcagctgcct gaccttcggc     420

agagagaccg tgatcgagta cctggtgagc ttcggcgtgt ggatcagaac cccccccgcc     480

tacagacccc ccaacgcccc catcctgagc accctgcccg agaccaccgt ggtgagaaga     540
```

-continued

```
agaggcagaa gccccagaag aagaaccccc agccccagaa gaagaagaag ccagagcccc    600

agaagaagaa gaagccagag cagagagagc cagtgcatgg acgtgaacgc cagcagagcc    660

ctggccaacg tgtacgacct gcccgacgac ttcttccccc agatcgacga cctggtgaga    720

gacgccaagg acgccctgga gccctactgg aaggccgaga ccatcaagaa gcacgtgctg    780

atcgccaccc acttcgtgga cttgatcgag gacttctggc agaccaccca gggcatgagc    840

cagatcgccg acgccctgag agccgtgatc ccccccacca ccgtgcccgt gcccgagggc    900

ttcctgatca cccacagcga ggccgaggag ctcccccctga acgacctgtt cagtctgcag    960

gaggagagaa tcgtgaactt ccagcccgac taccccatca ccgccagaat tcacacccac   1020

ctgagagtgt acaccaagct gaacgagcag gccctggaca aggccagaag actgctgtgg   1080

tggcactaca actgcctgct gtggggcgag gccaccgtga ccaactacat cagcagactg   1140

agaacctggc tgagcacccc cgagaagtac agaggcaagg acgcccccac catcgaggcc   1200

atcaccagac ccatccaggt ggcccagggc ggcagaaacc agaccaaggg caccagaaag   1260

cccagaggcc tggagcccag aagaagaaag gtgaagacca ccgtggtgta cggcagaaga   1320

agaagcaaga gcagaggcag aagaagcagc cccagccaga gagccggcag cccccctgccc   1380

agaaacagag gcaaccagac cagaagcccc agccccagag agtga                  1425
```

<210> SEQ ID NO 51
<211> LENGTH: 445
<212> TYPE: PRT
<213> ORGANISM: Artificial Sequence
<220> FEATURE:
<223> OTHER INFORMATION: Codon optimized HBV HBcAg-Stork HBcAg

<400> SEQUENCE: 51

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Asp Val Asn Ala Ser Arg Ala Leu
            180                 185                 190

Ala Asn Val Tyr Asp Leu Pro Asp Asp Phe Phe Pro Gln Ile Asp Asp
        195                 200                 205

Leu Val Arg Asp Ala Lys Asp Ala Leu Glu Pro Tyr Trp Lys Ala Glu
```

-continued

```
    210                 215                 220

Thr Ile Lys Lys His Val Leu Ile Ala Thr His Phe Val Asp Leu Ile
225                 230                 235                 240

Glu Asp Phe Trp Gln Thr Thr Gln Gly Met Ser Gln Ile Ala Asp Ala
                245                 250                 255

Leu Arg Ala Val Ile Pro Pro Thr Thr Thr Pro Val Pro Asp Gly Tyr
            260                 265                 270

Leu Ile Ser His Asn Glu Ala Gln Glu Leu Pro Leu Asn Asp Leu Phe
        275                 280                 285

Val Leu Gln Glu Glu Arg Ile Val Asn Phe Gln Pro Asp Tyr Pro Ile
    290                 295                 300

Thr Ala Arg Ile His Thr His Leu Arg Val Tyr Thr Lys Leu Asn Glu
305                 310                 315                 320

Gln Ala Leu Asp Lys Ala Arg Arg Leu Leu Trp Trp His Tyr Asn Cys
                325                 330                 335

Leu Leu Trp Gly Glu Ser Asn Val Thr Asn Tyr Ile Ser Arg Leu Arg
            340                 345                 350

Thr Trp Leu Ser Thr Pro Glu Lys Tyr Arg Gly Lys Asp Ala Pro Thr
        355                 360                 365

Ile Glu Ala Ile Thr Arg Pro Ile Gln Val Ala Gln Gly Ser Arg Asn
    370                 375                 380

Gln Thr Lys Gly Val Arg Lys Pro Arg Gly Leu Glu Pro Arg Arg Arg
385                 390                 395                 400

Lys Val Lys Thr Thr Val Val Tyr Gly Arg Arg Arg Ser Lys Ser Arg
                405                 410                 415

Gly Arg Arg Ser Ser Pro Ser Gln Arg Ala Gly Ser Pro Ile Pro Arg
            420                 425                 430

Asn Arg Glu Asn Gln Ser Arg Ser Ser Ser Pro Arg Glu
        435                 440                 445
```

<210> SEQ ID NO 52
<211> LENGTH: 1338
<212> TYPE: DNA
<213> ORGANISM: Artificial Sequence
<220> FEATURE:
<223> OTHER INFORMATION: Codon optimized HBV HBcAg-Stork HBcAg

<400> SEQUENCE: 52

```
atggacatcg acccctacaa ggagttcggc gccaccgtgg agctgctgag cttcctgccc     60

agcgacttct tccccagcgt gagagacctg ctggacaccg ccagcgccct gtacagagag    120

gccctggaga gccccgagca ctgcagcccc caccacaccg ccctgagaca ggccatcctg    180

tgctggggcg agctgatgac cctggccacc tgggtgggcg tgaacctgga ggaccccgcc    240

agcagagacc tggtggtgag ctacgtgaac accaacatgg gcctgaagtt cagacagctg    300

ctgtggttcc acatcagctg cctgaccttc ggcagagaga ccgtgatcga gtacctggtg    360

agcttcggcg tgtggatcag aacccccccc gcctacagac cccccaacgc ccccatcctg    420

agcaccctgc ccgagaccac cgtggtgaga agaagaggca gaagccccag aagaagaacc    480

cccagcccca gaagaagaag aagccagagc cccagaagaa gaagaagcca gagcagagag    540

agccagtgca tggacgtgaa cgccagcaga gccctggcca acgtgtacga cctgcccgac    600

gacttcttcc cccagatcga cgacctggtg agagacgcca aggacgccct ggagccctac    660

tggaaggccg agaccatcaa gaagcacgtg ctgatcgcca cccacttcgt ggacttgatc    720

gaggacttct ggcagaccac ccagggcatg agccagatcg ccgacgccct gagagccgtg    780
```

-continued

```
atcccccca ccaccacccc cgtgcccgac ggctacctga tcagccacaa cgaggcccag    840

gagctccccc tgaacgacct gttcgtgctg caggaggaga gaatcgtgaa cttccagccc    900

gactacccca tcaccgccag aattcacacc cacctgagag tgtacaccaa gctgaacgag    960

caggccctgg acaaggccag aagactgctg tggtggcact acaactgcct gctgtggggc   1020

gagagcaacg tgaccaacta catcagcaga ctgagaacct ggctgagcac ccccgagaag   1080

tacagaggca aggacgcccc caccatcgag gccatcacca gacccatcca ggtggcccag   1140

ggcagcagaa accagaccaa gggcgtgaga aagcccagag gcctggagcc cagaagaaga   1200

aaggtgaaga ccaccgtggt gtacggcaga agaagaagca agagcagagg cagaagaagc   1260

agccccagcc agagagccgg cagccccatc cccagaaaca gagagaacca gagcagaagc   1320

agcagcccca gagagtga                                                 1338
```

```
<210> SEQ ID NO 53
<211> LENGTH: 445
<212> TYPE: PRT
<213> ORGANISM: Artificial Sequence
<220> FEATURE:
<223> OTHER INFORMATION: Codon optimized HBV HBcAg-Heron core

<400> SEQUENCE: 53

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Asp Val Asn Ala Ser Arg Ala Leu
            180                 185                 190

Ala Asn Val Tyr Asp Leu Pro Asp Asp Phe Phe Pro Gln Ile Asp Asp
        195                 200                 205

Leu Val Arg Asp Ala Lys Asp Ala Leu Glu Pro Tyr Trp Lys Ala Glu
    210                 215                 220

Thr Ile Lys Lys His Val Leu Ile Ala Thr His Phe Val Asp Leu Ile
225                 230                 235                 240

Glu Asp Phe Trp Gln Thr Thr Gln Gly Met Ser Gln Ile Ala Asp Ala
                245                 250                 255

Leu Arg Ala Val Ile Pro Pro Thr Thr Val Pro Val Pro Glu Gly Phe
            260                 265                 270
```

```
Leu Ile Thr His Ser Glu Ala Glu Glu Leu Pro Leu Asn Asp Leu Phe
        275                 280                 285

Ser Leu Gln Glu Glu Arg Ile Val Asn Phe Gln Pro Asp Tyr Pro Ile
    290                 295                 300

Thr Ala Arg Ile His Thr His Leu Arg Val Tyr Thr Lys Leu Asn Glu
305                 310                 315                 320

Gln Ala Leu Asp Lys Ala Arg Arg Leu Leu Trp Trp His Tyr Asn Cys
                325                 330                 335

Leu Leu Trp Gly Glu Ala Thr Val Thr Asn Tyr Ile Ser Arg Leu Arg
            340                 345                 350

Thr Trp Leu Ser Thr Pro Glu Lys Tyr Arg Gly Lys Asp Ala Pro Thr
        355                 360                 365

Ile Glu Ala Ile Thr Arg Pro Ile Gln Val Ala Gln Gly Gly Arg Asn
    370                 375                 380

Gln Thr Lys Gly Thr Arg Lys Pro Arg Gly Leu Glu Pro Arg Arg Arg
385                 390                 395                 400

Lys Val Lys Thr Thr Val Val Tyr Gly Arg Arg Arg Ser Lys Ser Arg
                405                 410                 415

Gly Arg Arg Ser Ser Pro Ser Gln Arg Ala Gly Ser Pro Leu Pro Arg
            420                 425                 430

Asn Arg Gly Asn Gln Thr Arg Ser Pro Ser Pro Arg Glu
        435                 440                 445


<210> SEQ ID NO 54
<211> LENGTH: 1338
<212> TYPE: DNA
<213> ORGANISM: Artificial Sequence
<220> FEATURE:
<223> OTHER INFORMATION: Codon optimized HBV HBcAg-Heron core

<400> SEQUENCE: 54

atggacatcg acccctacaa ggagttcggc gccaccgtgg agctgctgag cttcctgccc      60

agcgacttct tccccagcgt gagagacctg ctggacaccg ccagcgccct gtacagagag     120

gccctggaga gccccgagca ctgcagcccc caccacaccg ccctgagaca ggccatcctg     180

tgctggggcg agctgatgac cctggccacc tgggtgggcg tgaacctgga ggaccccgcc     240

agcagagacc tggtggtgag ctacgtgaac accaacatgg gcctgaagtt cagacagctg     300

ctgtggttcc acatcagctg cctgaccttc ggcagagaga ccgtgatcga gtacctggtg     360

agcttcggcg tgtggatcag aacccccccc gcctacagac cccccaacgc ccccatcctg     420

agcaccctgc ccgagaccac cgtggtgaga agaagaggca gaagccccag aagaagaacc     480

cccagcccca gaagaagaag aagccagagc cccagaagaa gaagaagcca gagcagagag     540

agccagtgca tggacgtgaa cgccagcaga gccctggcca acgtgtacga cctgcccgac     600

gacttcttcc cccagatcga cgacctggtg agagacgcca aggacgccct ggagccctac     660

tggaaggccg agaccatcaa gaagcacgtg ctgatcgcca cccacttcgt ggacttgatc     720

gaggacttct ggcagaccac ccagggcatg agccagatcg ccgacgccct gagagccgtg     780

atcccccccca ccaccgtgcc cgtgcccgag ggcttcctga tcacccacag cgaggccgag     840

gagctccccc tgaacgacct gttcagtctg caggaggaga gaatcgtgaa cttccagccc     900

gactacccca tcaccgccag aattcacacc cacctgagag tgtacaccaa gctgaacgag     960

caggccctgg acaaggccag aagactgctg tggtggcact acaactgcct gctgtggggc    1020

gaggccaccg tgaccaacta catcagcaga ctgagaacct ggctgagcac ccccgagaag    1080
```

-continued

```
tacagaggca aggacgcccc caccatcgag gccatcacca gacccatcca ggtggcccag   1140

ggcggcagaa accagaccaa gggcaccaga aagcccagag gcctggagcc cagaagaaga   1200

aaggtgaaga ccaccgtggt gtacggcaga agaagaagca agagcagagg cagaagaagc   1260

agccccagcc agagagccgg cagccccctg cccagaaaca gaggcaacca gaccagaagc   1320

cccagcccca gagagtga                                                  1338
```

```
<210> SEQ ID NO 55
<211> LENGTH: 422
<212> TYPE: PRT
<213> ORGANISM: Artificial Sequence
<220> FEATURE:
<223> OTHER INFORMATION: Codon optimized BetvI (Birch)-Stork HBcAg

<400> SEQUENCE: 55

Met Gly Val Phe Asn Tyr Glu Thr Glu Thr Thr Ser Val Ile Pro Ala
 1               5                  10                  15

Ala Arg Leu Phe Lys Ala Phe Ile Leu Asp Gly Asp Asn Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

Met Asp Val Asn Ala Ser Arg Ala Leu Ala Asn Val Tyr Asp Leu Pro
                165                 170                 175

Asp Asp Phe Phe Pro Gln Ile Asp Asp Leu Val Arg Asp Ala Lys Asp
            180                 185                 190

Ala Leu Glu Pro Tyr Trp Lys Ala Glu Thr Ile Lys Lys His Val Leu
        195                 200                 205

Ile Ala Thr His Phe Val Asp Leu Ile Glu Asp Phe Trp Gln Thr Thr
    210                 215                 220

Gln Gly Met Ser Gln Ile Ala Asp Ala Leu Arg Ala Val Ile Pro Pro
225                 230                 235                 240

Thr Thr Thr Pro Val Pro Asp Gly Tyr Leu Ile Ser His Asn Glu Ala
                245                 250                 255

Gln Glu Leu Pro Leu Asn Asp Leu Phe Val Leu Gln Glu Glu Arg Ile
            260                 265                 270

Val Asn Phe Gln Pro Asp Tyr Pro Ile Thr Ala Arg Ile His Thr His
        275                 280                 285

Leu Arg Val Tyr Thr Lys Leu Asn Glu Gln Ala Leu Asp Lys Ala Arg
    290                 295                 300

Arg Leu Leu Trp Trp His Tyr Asn Cys Leu Leu Trp Gly Glu Ser Asn
305                 310                 315                 320
```

-continued

```
Val Thr Asn Tyr Ile Ser Arg Leu Arg Thr Trp Leu Ser Thr Pro Glu
                325                 330                 335

Lys Tyr Arg Gly Lys Asp Ala Pro Thr Ile Glu Ala Ile Thr Arg Pro
            340                 345                 350

Ile Gln Val Ala Gln Gly Ser Arg Asn Gln Thr Lys Gly Val Arg Lys
        355                 360                 365

Pro Arg Gly Leu Glu Pro Arg Arg Arg Lys Val Lys Thr Thr Val Val
    370                 375                 380

Tyr Gly Arg Arg Arg Ser Lys Ser Arg Gly Arg Arg Ser Ser Pro Ser
385                 390                 395                 400

Gln Arg Ala Gly Ser Pro Ile Pro Arg Asn Arg Glu Asn Gln Ser Arg
                405                 410                 415

Ser Ser Ser Pro Arg Glu
            420


<210> SEQ ID NO 56
<211> LENGTH: 1269
<212> TYPE: DNA
<213> ORGANISM: Artificial Sequence
<220> FEATURE:
<223> OTHER INFORMATION: Codon optimized BetvI (Birch)-Stork HBcAg

<400> SEQUENCE: 56

atgggcgtct tcaattacga aaccgagaca actagtgtga tcccagctgc acgccttttt      60

aaggccttca ttcttgatgg agacaacctt gtgccaaagg tggctcccca agctattagt     120

agcgtcgaaa acatcgaggg aaatggcgga ccgggaacca tcaaaaagat caactttccg     180

gagggcttcc ctttcaagta cgttaaggac agggttgatg aagttgatca tacaaatttt     240

aagtacaact actccgtgat cgagggcggc cccgttggag atactctgga aaagatcagc     300

aacgagatta agatcgtggc tacacccgat ggcgggtgtg tgcttaagat ctccaacaaa     360

tatcatacca aagggaacca cgaggttaag gctgaacagg tgaaggcatc aaaggagatg     420

ggagagaccc tcctccgagc ggtggagtct tacttgctcg cacacagcga tgcttacaat     480

atggacgtga acgccagcag agccctggcc aacgtgtacg acctgcccga cgacttcttc     540

ccccagatcg acgacctggt gagagacgcc aaggacgccc tggagcccta ctggaaggcc     600

gagaccatca agaagcacgt gctgatcgcc acccacttcg tggacttgat cgaggacttc     660

tggcagacca cccagggcat gagccagatc gccgacgccc tgagagccgt gatccccccc     720

accaccaccc ccgtgcccga cggctacctg atcagccaca acgaggccca ggagctcccc     780

ctgaacgacc tgttcgtgct gcaggaggag agaatcgtga acttccagcc cgactacccc     840

atcaccgcca gaattcacac ccacctgaga gtgtacacca agctgaacga gcaggccctg     900

gacaaggcca gaagactgct gtggtggcac tacaactgcc tgctgtgggg cgagagcaac     960

gtgaccaact acatcagcag actgagaacc tggctgagca cccccgagaa gtacagaggc    1020

aaggacgccc ccaccatcga ggccatcacc agacccatcc aggtggccca gggcagcaga    1080

aaccagacca agggcgtgag aaagcccaga ggcctggagc ccagaagaag aaaggtgaag    1140

accaccgtgg tgtacggcag aagaagaagc aagagcagag gcagaagaag cagccccagc    1200

cagagagccg gcagccccat ccccagaaac agagagaacc agagcagaag cagcagcccc    1260

agagagtga                                                            1269


<210> SEQ ID NO 57
<211> LENGTH: 422
<212> TYPE: PRT
<213> ORGANISM: Artificial Sequence
```

<220> FEATURE:
<223> OTHER INFORMATION: Codon optimized BetvI (Birch)-Heron HBcAg

<400> SEQUENCE: 57

```
Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

Met Asp Val Asn Ala Ser Arg Ala Leu Ala Asn Val Tyr Asp Leu Pro
                165                 170                 175

Asp Asp Phe Phe Pro Gln Ile Asp Asp Leu Val Arg Asp Ala Lys Asp
            180                 185                 190

Ala Leu Glu Pro Tyr Trp Lys Ala Glu Thr Ile Lys Lys His Val Leu
        195                 200                 205

Ile Ala Thr His Phe Val Asp Leu Ile Glu Asp Phe Trp Gln Thr Thr
    210                 215                 220

Gln Gly Met Ser Gln Ile Ala Asp Ala Leu Arg Ala Val Ile Pro Pro
225                 230                 235                 240

Thr Thr Val Pro Val Pro Glu Gly Phe Leu Ile Thr His Ser Glu Ala
                245                 250                 255

Glu Glu Leu Pro Leu Asn Asp Leu Phe Ser Leu Gln Glu Glu Arg Ile
            260                 265                 270

Val Asn Phe Gln Pro Asp Tyr Pro Ile Thr Ala Arg Ile His Thr His
        275                 280                 285

Leu Arg Val Tyr Thr Lys Leu Asn Glu Gln Ala Leu Asp Lys Ala Arg
    290                 295                 300

Arg Leu Leu Trp Trp His Tyr Asn Cys Leu Leu Trp Gly Glu Ala Thr
305                 310                 315                 320

Val Thr Asn Tyr Ile Ser Arg Leu Arg Thr Trp Leu Ser Thr Pro Glu
                325                 330                 335

Lys Tyr Arg Gly Lys Asp Ala Pro Thr Ile Glu Ala Ile Thr Arg Pro
            340                 345                 350

Ile Gln Val Ala Gln Gly Gly Arg Asn Gln Thr Lys Gly Thr Arg Lys
        355                 360                 365

Pro Arg Gly Leu Glu Pro Arg Arg Arg Lys Val Lys Thr Thr Val Val
    370                 375                 380

Tyr Gly Arg Arg Arg Ser Lys Ser Arg Gly Arg Arg Ser Ser Pro Ser
385                 390                 395                 400
```

```
Gln Arg Ala Gly Ser Pro Leu Pro Arg Asn Arg Gly Asn Gln Thr Arg
                405                 410                 415

Ser Pro Ser Pro Arg Glu
            420


<210> SEQ ID NO 58
<211> LENGTH: 1269
<212> TYPE: DNA
<213> ORGANISM: Artificial Sequence
<220> FEATURE:
<223> OTHER INFORMATION: Codon optimized BetvI (Birch)-Heron HBcAg

<400> SEQUENCE: 58

atgggcgtct tcaattacga aaccgagaca actagtgtga tcccagctgc acgccttttt      60

aaggccttca ttcttgatgg agacaacctt gtgccaaagg tggctcccca agctattagt     120

agcgtcgaaa acatcgaggg aaatggcgga ccgggaacca tcaaaaagat caactttccg     180

gagggcttcc ctttcaagta cgttaaggac agggttgatg aagttgatca tacaaatttt     240

aagtacaact actccgtgat cgagggcggc cccgttggag atactctgga aaagatcagc     300

aacgagatta agatcgtggc tacacccgat ggcgggtgtg tgcttaagat ctccaacaaa     360

tatcatacca aagggaacca cgaggttaag gctgaacagg tgaaggcatc aaaggagatg     420

ggagagaccc tcctccgagc ggtggagtct tacttgctcg cacacagcga tgcttacaat     480

atggacgtga acgccagcag agccctggcc aacgtgtacg acctgcccga cgacttcttc     540

ccccagatcg acgacctggt gagagacgcc aaggacgccc tggagcccta ctggaaggcc     600

gagaccatca agaagcacgt gctgatcgcc acccacttcg tggacttgat cgaggacttc     660

tggcagacca cccagggcat gagccagatc gccgacgccc tgagagccgt gatccccccc     720

accaccgtgc ccgtgcccga gggcttcctg atcacccaca gcgaggccga ggagctcccc     780

ctgaacgacc tgttcagtct gcaggaggag agaatcgtga acttccagcc cgactacccc     840

atcaccgcca gaattcacac ccacctgaga gtgtacacca agctgaacga gcaggccctg     900

gacaaggcca gaagactgct gtggtggcac tacaactgcc tgctgtgggg cgaggccacc     960

gtgaccaact acatcagcag actgagaacc tggctgagca cccccgagaa gtacagaggc    1020

aaggacgccc ccaccatcga ggccatcacc agacccatcc aggtggccca gggcggcaga    1080

aaccagacca agggcaccag aaagcccaga ggcctggagc ccagaagaag aaaggtgaag    1140

accaccgtgg tgtacggcag aagaagaagc aagagcagag gcagaagaag cagccccagc    1200

cagagagccg gcagcccccct gcccagaaac agaggcaacc agaccagaag ccccagcccc    1260

agagagtga                                                            1269


<210> SEQ ID NO 59
<211> LENGTH: 648
<212> TYPE: PRT
<213> ORGANISM: Artificial Sequence
<220> FEATURE:
<223> OTHER INFORMATION: Codon optimized Ovalbumin-Stork HBcAg

<400> SEQUENCE: 59

Met Gly Ser Ile Gly Ala Ala Ser Met Glu Phe Cys Phe Asp Val Phe
 1               5                  10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
```

-continued

```
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro Met Asp Val Asn Ala Ser Arg Ala Leu Ala Asn Val Tyr Asp
385                 390                 395                 400

Leu Pro Asp Asp Phe Phe Pro Gln Ile Asp Asp Leu Val Arg Asp Ala
                405                 410                 415

Lys Asp Ala Leu Glu Pro Tyr Trp Lys Ala Glu Thr Ile Lys Lys His
            420                 425                 430

Val Leu Ile Ala Thr His Phe Val Asp Leu Ile Glu Asp Phe Trp Gln
        435                 440                 445

Thr Thr Gln Gly Met Ser Gln Ile Ala Asp Ala Leu Arg Ala Val Ile
    450                 455                 460

Pro Pro Thr Thr Thr Pro Val Pro Asp Gly Tyr Leu Ile Ser His Asn
465                 470                 475                 480
```

```
Glu Ala Gln Glu Leu Pro Leu Asn Asp Leu Phe Val Leu Gln Glu Glu
                485                 490                 495

Arg Ile Val Asn Phe Gln Pro Asp Tyr Pro Ile Thr Ala Arg Ile His
            500                 505                 510

Thr His Leu Arg Val Tyr Thr Lys Leu Asn Glu Gln Ala Leu Asp Lys
        515                 520                 525

Ala Arg Arg Leu Leu Trp Trp His Tyr Asn Cys Leu Leu Trp Gly Glu
    530                 535                 540

Ser Asn Val Thr Asn Tyr Ile Ser Arg Leu Arg Thr Trp Leu Ser Thr
545                 550                 555                 560

Pro Glu Lys Tyr Arg Gly Lys Asp Ala Pro Thr Ile Glu Ala Ile Thr
                565                 570                 575

Arg Pro Ile Gln Val Ala Gln Gly Ser Arg Asn Gln Thr Lys Gly Val
            580                 585                 590

Arg Lys Pro Arg Gly Leu Glu Pro Arg Arg Arg Lys Val Lys Thr Thr
        595                 600                 605

Val Val Tyr Gly Arg Arg Arg Ser Lys Ser Arg Gly Arg Arg Ser Ser
    610                 615                 620

Pro Ser Gln Arg Ala Gly Ser Pro Ile Pro Arg Asn Arg Glu Asn Gln
625                 630                 635                 640

Ser Arg Ser Ser Ser Pro Arg Glu
                645
```

<210> SEQ ID NO 60
<211> LENGTH: 1947
<212> TYPE: DNA
<213> ORGANISM: Artificial Sequence
<220> FEATURE:
<223> OTHER INFORMATION: Codon optimized Ovalbumin-Stork HBcAg

<400> SEQUENCE: 60

```
atgggcagca tcggcgccgc cagcatggag ttctgcttcg acgtgttcaa ggagctgaag     60

gtgcaccacg ccaacgagaa catcttctac tgccccatcg ccatcatgag cgccctggcc    120

atggtgtacc tgggcgccaa ggacagcacc cgcacccaga tcaacaaggt ggtgcgcttc    180

gacaagctgc ccggcttcgg cgacagcatc gaggcccagt gcggcaccag cgtgaacgtg    240

cacagcagcc tgcgcgacat cctgaaccag atcaccaagc ccaacgacgt gtacagcttc    300

agcctggcca gccgcctgta cgccgaggag cgctacccca tcctgcccga gtacctgcag    360

tgcgtgaagg agctgtaccg cggcggcctg gagcccatca acttccagac cgccgccgac    420

caggcccgcg agctgatcaa cagctgggtg gagagccaga ccaacggcat catccgcaac    480

gtgctgcagc ccagcagcgt ggacagccag accgccatgg tgctggtgaa cgccatcgtg    540

ttcaagggcc tgtgggagaa ggccttcaag gacgaggaca cccaggccat gcccttccgc    600

gtgaccgagc aggagagcaa gcccgtgcag atgatgtacc agatcggcct gttccgcgtg    660

gccagcatgg ccagcgagaa gatgaagatc ctggagctgc ccttcgccag cggcaccatg    720

agcatgctgg tgctgctgcc cgacgaggtg agcggcctgg agcagctgga gagcatcatc    780

aacttcgaga agctgaccga gtggaccagc agcaacgtga tggaggagcg caagatcaag    840

gtgtacctgc cccgcatgaa gatggaggag aagtacaacc tgaccagcgt gctgatggcc    900

atgggcatca ccgacgtgtt cagcagcagc gccaacctga gcggcatcag cagcgccgag    960

agcctgaaga tcagccaggc cgtgcacgcc gcccacgccg agatcaacga ggccggccgc   1020

gaggtggtgg gcagcgccga ggccggcgtg gacgccgcca gcgtgagcga ggagttccgc   1080

gccgaccacc ccttcctgtt ctgcatcaag cacatcgcca ccaacgccgt gctgttcttc   1140
```

```
ggccgctgcg tgagccccat ggacgtgaac gccagcagag ccctggccaa cgtgtacgac   1200

ctgcccgacg acttcttccc ccagatcgac gacctggtga gagacgccaa ggacgccctg   1260

gagccctact ggaaggccga gaccatcaag aagcacgtgc tgatcgccac ccacttcgtg   1320

gacttgatcg aggacttctg gcagaccacc cagggcatga gccagatcgc cgacgccctg   1380

agagccgtga tcccccccac caccaccccc gtgcccgacg gctacctgat cagccacaac   1440

gaggcccagg agctccccct gaacgacctg ttcgtgctgc aggaggagag aatcgtgaac   1500

ttccagcccg actaccccat caccgccaga attcacaccc acctgagagt gtacaccaag   1560

ctgaacgagc aggccctgga caaggccaga agactgctgt ggtggcacta caactgcctg   1620

ctgtggggcg agagcaacgt gaccaactac atcagcagac tgagaacctg gctgagcacc   1680

cccgagaagt acagaggcaa ggacgccccc accatcgagg ccatcaccag acccatccag   1740

gtggcccagg gcagcagaaa ccagaccaag ggcgtgagaa agcccagagg cctggagccc   1800

agaagaagaa aggtgaagac caccgtggtg tacggcagaa gaagaagcaa gagcagaggc   1860

agaagaagca gccccagcca gagagccggc agccccatcc ccagaaacag agagaaccag   1920

agcagaagca gcagccccag agagtga                                       1947


<210> SEQ ID NO 61
<211> LENGTH: 648
<212> TYPE: PRT
<213> ORGANISM: Artificial Sequence
<220> FEATURE:
<223> OTHER INFORMATION: Codon optimized Ovalbumin-Heron HBcAg

<400> SEQUENCE: 61

Met Gly Ser Ile Gly Ala Ala Ser Met Glu Phe Cys Phe Asp Val Phe
 1               5                  10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220
```

-continued

Ser Glu Lys Met Lys Ile Leu Glu Leu Pro Phe Ala Ser Gly Thr Met
225 230 235 240

Ser Met Leu Val Leu Leu Pro Asp Glu Val Ser Gly Leu Glu Gln Leu
245 250 255

Glu Ser Ile Ile Asn Phe Glu Lys Leu Thr Glu Trp Thr Ser Ser Asn
260 265 270

Val Met Glu Glu Arg Lys Ile Lys Val Tyr Leu Pro Arg Met Lys Met
275 280 285

Glu Glu Lys Tyr Asn Leu Thr Ser Val Leu Met Ala Met Gly Ile Thr
290 295 300

Asp Val Phe Ser Ser Ser Ala Asn Leu Ser Gly Ile Ser Ser Ala Glu
305 310 315 320

Ser Leu Lys Ile Ser Gln Ala Val His Ala Ala His Ala Glu Ile Asn
325 330 335

Glu Ala Gly Arg Glu Val Val Gly Ser Ala Glu Ala Gly Val Asp Ala
340 345 350

Ala Ser Val Ser Glu Glu Phe Arg Ala Asp His Pro Phe Leu Phe Cys
355 360 365

Ile Lys His Ile Ala Thr Asn Ala Val Leu Phe Phe Gly Arg Cys Val
370 375 380

Ser Pro Met Asp Val Asn Ala Ser Arg Ala Leu Ala Asn Val Tyr Asp
385 390 395 400

Leu Pro Asp Asp Phe Phe Pro Gln Ile Asp Asp Leu Val Arg Asp Ala
405 410 415

Lys Asp Ala Leu Glu Pro Tyr Trp Lys Ala Glu Thr Ile Lys Lys His
420 425 430

Val Leu Ile Ala Thr His Phe Val Asp Leu Ile Glu Asp Phe Trp Gln
435 440 445

Thr Thr Gln Gly Met Ser Gln Ile Ala Asp Ala Leu Arg Ala Val Ile
450 455 460

Pro Pro Thr Thr Val Pro Val Pro Glu Gly Phe Leu Ile Thr His Ser
465 470 475 480

Glu Ala Glu Glu Leu Pro Leu Asn Asp Leu Phe Ser Leu Gln Glu Glu
485 490 495

Arg Ile Val Asn Phe Gln Pro Asp Tyr Pro Ile Thr Ala Arg Ile His
500 505 510

Thr His Leu Arg Val Tyr Thr Lys Leu Asn Glu Gln Ala Leu Asp Lys
515 520 525

Ala Arg Arg Leu Leu Trp Trp His Tyr Asn Cys Leu Leu Trp Gly Glu
530 535 540

Ala Thr Val Thr Asn Tyr Ile Ser Arg Leu Arg Thr Trp Leu Ser Thr
545 550 555 560

Pro Glu Lys Tyr Arg Gly Lys Asp Ala Pro Thr Ile Glu Ala Ile Thr
565 570 575

Arg Pro Ile Gln Val Ala Gln Gly Gly Arg Asn Gln Thr Lys Gly Thr
580 585 590

Arg Lys Pro Arg Gly Leu Glu Pro Arg Arg Arg Lys Val Lys Thr Thr
595 600 605

Val Val Tyr Gly Arg Arg Arg Ser Lys Ser Arg Gly Arg Arg Ser Ser
610 615 620

Pro Ser Gln Arg Ala Gly Ser Pro Leu Pro Arg Asn Arg Gly Asn Gln
625 630 635 640

Thr Arg Ser Pro Ser Pro Arg Glu

645

<210> SEQ ID NO 62
<211> LENGTH: 1947
<212> TYPE: DNA
<213> ORGANISM: Artificial Sequence
<220> FEATURE:
<223> OTHER INFORMATION: Codon optimized Ovalbumin-Heron HBcAg

<400> SEQUENCE: 62
atgggcagca tcggcgccgc cagcatggag ttctgcttcg acgtgttcaa ggagctgaag 60
gtgcaccacg ccaacgagaa catcttctac tgccccatcg ccatcatgag cgccctggcc 120
atggtgtacc tgggcgccaa ggacagcacc cgcacccaga tcaacaaggt ggtgcgcttc 180
gacaagctgc ccggcttcgg cgacagcatc gaggcccagt gcggcaccag cgtgaacgtg 240
cacagcagcc tgcgcgacat cctgaaccag atcaccaagc ccaacgacgt gtacagcttc 300
agcctggcca gccgcctgta cgccgaggag cgctacccca tcctgcccga gtacctgcag 360
tgcgtgaagg agctgtaccg cggcggcctg gagcccatca acttccagac cgccgccgac 420
caggcccgcg agctgatcaa cagctgggtg gagagccaga ccaacggcat catccgcaac 480
gtgctgcagc ccagcagcgt ggacagccag accgccatgg tgctggtgaa cgccatcgtg 540
ttcaagggcc tgtgggagaa ggccttcaag gacgaggaca cccaggccat gcccttccgc 600
gtgaccgagc aggagagcaa gcccgtgcag atgatgtacc agatcggcct gttccgcgtg 660
gccagcatgg ccagcgagaa gatgaagatc ctggagctgc ccttcgccag cggcaccatg 720
agcatgctgg tgctgctgcc cgacgaggtg agcggcctgg agcagctgga gagcatcatc 780
aacttcgaga agctgaccga gtggaccagc agcaacgtga tggaggagcg caagatcaag 840
gtgtacctgc cccgcatgaa gatggaggag aagtacaacc tgaccagcgt gctgatggcc 900
atgggcatca ccgacgtgtt cagcagcagc gccaacctga gcggcatcag cagcgccgag 960
agcctgaaga tcagccaggc cgtgcacgcc gcccacgccg agatcaacga ggccggccgc 1020
gaggtggtgg gcagcgccga ggccggcgtg gacgccgcca gcgtgagcga ggagttccgc 1080
gccgaccacc ccttcctgtt ctgcatcaag cacatcgcca ccaacgccgt gctgttcttc 1140
ggccgctgcg tgagccccat ggacgtgaac gccagcagag ccctggccaa cgtgtacgac 1200
ctgcccgacg acttcttccc ccagatcgac gacctggtga gagacgccaa ggacgccctg 1260
gagccctact ggaaggccga gaccatcaag aagcacgtgc tgatcgccac ccacttcgtg 1320
gacttgatcg aggacttctg gcagaccacc cagggcatga gccagatcgc cgacgccctg 1380
agagccgtga tcccccccac caccgtgccc gtgcccgagg gcttcctgat cacccacagc 1440
gaggccgagg agctccccct gaacgacctg ttcagtctgc aggaggagag aatcgtgaac 1500
ttccagcccg actaccccat caccgccaga attcacaccc acctgagagt gtacaccaag 1560
ctgaacgagc aggccctgga caaggccaga agactgctgt ggtggcacta caactgcctg 1620
ctgtggggcg aggccaccgt gaccaactac atcagcagac tgagaacctg gctgagcacc 1680
cccgagaagt acagaggcaa ggacgccccc accatcgagg ccatcaccag acccatccag 1740
gtggcccagg gcggcagaaa ccagaccaag ggcaccagaa agcccagagg cctggagccc 1800
agaagaagaa aggtgaagac caccgtggtg tacggcagaa gaagaagcaa gagcagaggc 1860
agaagaagca gccccagcca gagagccggc agccccctgc ccagaaacag aggcaaccag 1920
accagaagcc ccagccccag agagtga 1947

<210> SEQ ID NO 63

<211> LENGTH: 1417
<212> TYPE: PRT
<213> ORGANISM: Artificial Sequence
<220> FEATURE:
<223> OTHER INFORMATION: Codon opt. NS3/4A-4Bjunct-NS5A-4Bjunct-Stork HBcAg

<400> SEQUENCE: 63

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380
```

```
Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Gly Ser Gly Ser Trp Leu Arg
    690                 695                 700

Asp Val Trp Asp Trp Ile Cys Thr Val Leu Thr Asp Phe Lys Thr Trp
705                 710                 715                 720

Leu Gln Ser Lys Leu Leu Pro Lys Leu Pro Gly Val Pro Phe Phe Ser
                725                 730                 735

Cys Gln Arg Gly Tyr Lys Gly Val Trp Arg Gly Asp Gly Ile Met Gln
            740                 745                 750

Thr Thr Cys Pro Cys Gly Ala Gln Ile Thr Gly His Val Lys Asn Gly
        755                 760                 765

Ser Met Arg Ile Val Gly Pro Lys Thr Cys Ser Asn Thr Trp His Gly
    770                 775                 780

Thr Phe Pro Ile Asn Ala Tyr Thr Thr Gly Pro Cys Thr Pro Ser Pro
785                 790                 795                 800

Ala Pro Asn Tyr Ser Arg Ala Leu Trp Arg Val Ala Ala Glu Glu Tyr
```

-continued

```
                805                 810                 815

Val Glu Ile Thr Arg Val Gly Asp Phe His Tyr Val Thr Gly Met Thr
            820                 825                 830

Thr Asp Asn Val Lys Cys Pro Cys Gln Val Pro Ala Pro Glu Phe Phe
        835                 840                 845

Thr Glu Leu Asp Gly Val Arg Leu His Arg Tyr Ala Pro Ala Cys Arg
    850                 855                 860

Pro Leu Leu Arg Glu Asp Val Thr Phe Gln Val Gly Leu Asn Gln Tyr
865                 870                 875                 880

Leu Val Gly Ser Gln Leu Pro Cys Glu Pro Glu Pro Asp Val Ala Val
                885                 890                 895

Leu Thr Ser Met Leu Thr Asp Pro Ser His Ile Thr Ala Glu Thr Ala
            900                 905                 910

Lys Arg Arg Leu Ala Arg Gly Ser Pro Pro Ser Leu Ala Ser Ser Ser
        915                 920                 925

Ala Ser Gln Leu Ser Ala Pro Ser Leu Lys Ala Thr Cys Thr Thr His
    930                 935                 940

His Asp Ser Pro Asp Ala Asp Leu Ile Glu Ala Asn Leu Leu Trp Arg
945                 950                 955                 960

Gln Glu Met Gly Gly Asn Ile Thr Arg Val Glu Ser Glu Asn Lys Val
                965                 970                 975

Val Ile Leu Asp Ser Phe Asp Pro Leu Arg Ala Glu Glu Asp Glu Arg
            980                 985                 990

Glu Val Ser Val Ala Ala Glu Ile Leu Arg Lys Ser Lys Lys Phe Pro
        995                 1000                1005

Pro Ala Leu Pro Ile Trp Ala Arg Pro Asp Tyr Asn Pro Pro Leu Leu
    1010                1015                1020

Glu Ser Trp Lys Ser Pro Asp Tyr Val Pro Pro Ala Val His Gly Cys
1025                1030                1035                1040

Pro Leu Pro Pro Thr Thr Gly Pro Pro Ile Pro Pro Pro Arg Lys Lys
                1045                1050                1055

Arg Thr Val Val Leu Thr Glu Ser Thr Val Ser Ser Ala Leu Ala Glu
            1060                1065                1070

Leu Ala Thr Lys Thr Phe Gly Ser Ser Gly Ser Ser Ala Val Asp Ser
        1075                1080                1085

Gly Thr Ala Thr Ala Pro Pro Asp Gln Thr Ser Asp Asp Gly Asp Lys
    1090                1095                1100

Glu Ser Asp Ile Glu Ser Tyr Ser Ser Met Pro Pro Leu Glu Gly Glu
1105                1110                1115                1120

Pro Gly Asp Pro Asp Leu Ser Asp Gly Ser Trp Ser Thr Val Ser Gly
                1125                1130                1135

Glu Ala Gly Asp Asp Ile Val Cys Cys Ser Gln His Leu Pro Tyr Ile
            1140                1145                1150

Glu Gln Gly Met Asp Val Asn Ala Ser Arg Ala Leu Ala Asn Val Tyr
        1155                1160                1165

Asp Leu Pro Asp Asp Phe Phe Pro Gln Ile Asp Asp Leu Val Arg Asp
    1170                1175                1180

Ala Lys Asp Ala Leu Glu Pro Tyr Trp Lys Ala Glu Thr Ile Lys Lys
1185                1190                1195                1200

His Val Leu Ile Ala Thr His Phe Val Asp Leu Ile Glu Asp Phe Trp
                1205                1210                1215

Gln Thr Thr Gln Gly Met Ser Gln Ile Ala Asp Ala Leu Arg Ala Val
            1220                1225                1230
```

```
Ile Pro Pro Thr Thr Thr Pro Val Pro Asp Gly Tyr Leu Ile Ser His
        1235                1240                1245

Asn Glu Ala Gln Glu Leu Pro Leu Asn Asp Leu Phe Val Leu Gln Glu
    1250                1255                1260

Glu Arg Ile Val Asn Phe Gln Pro Asp Tyr Pro Ile Thr Ala Arg Ile
1265                1270                1275                1280

His Thr His Leu Arg Val Tyr Thr Lys Leu Asn Glu Gln Ala Leu Asp
                1285                1290                1295

Lys Ala Arg Arg Leu Leu Trp Trp His Tyr Asn Cys Leu Leu Trp Gly
            1300                1305                1310

Glu Ser Asn Val Thr Asn Tyr Ile Ser Arg Leu Arg Thr Trp Leu Ser
        1315                1320                1325

Thr Pro Glu Lys Tyr Arg Gly Lys Asp Ala Pro Thr Ile Glu Ala Ile
    1330                1335                1340

Thr Arg Pro Ile Gln Val Ala Gln Gly Ser Arg Asn Gln Thr Lys Gly
1345                1350                1355                1360

Val Arg Lys Pro Arg Gly Leu Glu Pro Arg Arg Arg Lys Val Lys Thr
                1365                1370                1375

Thr Val Val Tyr Gly Arg Arg Arg Ser Lys Ser Arg Gly Arg Arg Ser
            1380                1385                1390

Ser Pro Ser Gln Arg Ala Gly Ser Pro Ile Pro Arg Asn Arg Glu Asn
        1395                1400                1405

Gln Ser Arg Ser Ser Ser Pro Arg Glu
    1410                1415
```

<210> SEQ ID NO 64
<211> LENGTH: 4254
<212> TYPE: DNA
<213> ORGANISM: Artificial Sequence
<220> FEATURE:
<223> OTHER INFORMATION: Codon opt. NS3/4A-4Bjunct-NS5A-4Bjunct-Stork HBcAg

<400> SEQUENCE: 64

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020
```

gccctgagca ccaccggcga gatccccttc tacggcaagg ccatcccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggccccccggc 1440
gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800
taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcag ccagcacctg ccctacatcg agcagggcat gggatctgga 2100
agctggctga gggatgtttg ggattggatt tgtaccgtcc tcaccgactt caaaacctgg 2160
ctccagtcca agctgctgcc aaagctgccc ggagtgccat tcttctcctg tcagaggggc 2220
tataaaggcg tgtggagggg cgatggaatt atgcagacta cttgcccctg tggagctcaa 2280
attactgggc acgttaagaa tggctccatg cggattgttg gcccaaaaac ctgttccaac 2340
acctggcacg gaaccttccc tattaacgct tacaccaccg gaccttgcac tccttccccc 2400
gcacctaatt attcccgggc tctctggcgg gtggcagcag aggaatatgt cgaaattacc 2460
agagtcggcg acttccacta cgtcacagga atgactacag acaacgttaa atgtccctgc 2520
caagtgcccg ctccagagtt ctttaccgaa ctcgacgggg ttaggctcca cagatacgca 2580
cccgcctgcc ggccactgct gcgggaagac gtcacattcc aggtcgggct gaaccagtac 2640
ctggtgggct ctcagctgcc ttgtgagcct gagcccgacg tggcagttct caccagcatg 2700
ctcaccgatc ctagccacat caccgctgag acagccaaac gccgcctggc tagagggtcc 2760
cctccctctc tggccagctc cagcgctagc cagctctccg caccaagcct gaaagccaca 2820
tgcactacac accacgatag ccccgacgca gacctgattg aagccaacct cctctggaga 2880
caggaaatgg gcggaaacat cactagggtc gaatccgaga ataaagtggt tattctggat 2940
agcttcgacc cactcagggc agaggaagat gagagagagg ttagcgtggc cgctgagatt 3000
ctccgcaagt ccaaaaagtt ccctcccgca ctgcccattt gggcaaggcc cgattacaat 3060
cctccactgc tcgagagctg gaagtcccct gactacgtgc caccagccgt ccacggatgc 3120
cctctgcccc ctaccacagg accaccaatt ccaccccccta gaaagaaacg gaccgtggtt 3180
ctgactgagt ccaccgtgtc ctctgcactc gctgagctgg caaccaagac ctttggatcc 3240
agcggatcct ccgcagtcga ctccggcacc gctaccgccc cacccgatca aacctctgac 3300
gatggagaca aggagagcga tattgagtcc tattccagca tgccccccact cgagggagaa 3360
cccggcgacc ccgacctgag cgatgggtcc tggagcactg tgagcgggga agcaggggac 3420

```
gacattgtct gttgcagcca gcacctgccc tacatcgagc agggcatgga cgtgaacgcc   3480

agcagagccc tggccaacgt gtacgacctg cccgacgact tcttccccca gatcgacgac   3540

ctggtgagag acgccaagga cgccctggag ccctactgga aggccgagac catcaagaag   3600

cacgtgctga tcgccaccca cttcgtggac ttgatcgagg acttctggca gaccacccag   3660

ggcatgagcc agatcgccga cgccctgaga gccgtgatcc cccccaccac cacccccgtg   3720

cccgacggct acctgatcag ccacaacgag gcccaggagc tccccctgaa cgacctgttc   3780

gtgctgcagg aggagagaat cgtgaacttc cagcccgact accccatcac cgccagaatt   3840

cacacccacc tgagagtgta caccaagctg aacgagcagg ccctggacaa ggccagaaga   3900

ctgctgtggt ggcactacaa ctgcctgctg tggggcgaga gcaacgtgac caactacatc   3960

agcagactga gaacctggct gagcaccccc gagaagtaca gaggcaagga cgcccccacc   4020

atcgaggcca tcaccagacc catccaggtg gcccagggca gcagaaacca gaccaagggc   4080

gtgagaaagc ccagaggcct ggagcccaga agaagaaagg tgaagaccac cgtggtgtac   4140

ggcagaagaa gaagcaagag cagaggcaga agaagcagcc ccagccagag agccggcagc   4200

cccatcccca gaaacagaga gaaccagagc agaagcagca gccccagaga gtga         4254
```

```
<210> SEQ ID NO 65
<211> LENGTH: 1417
<212> TYPE: PRT
<213> ORGANISM: Artificial Sequence
<220> FEATURE:
<223> OTHER INFORMATION: Codon opt. NS3/4A-4Bjunct-NS5A-4Bjunct-Heron
      HBcAg

<400> SEQUENCE: 65

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
```

-continued

```
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640
```

```
Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Gly Ser Gly Ser Trp Leu Arg
    690                 695                 700

Asp Val Trp Asp Trp Ile Cys Thr Val Leu Thr Asp Phe Lys Thr Trp
705                 710                 715                 720

Leu Gln Ser Lys Leu Leu Pro Lys Leu Pro Gly Val Pro Phe Phe Ser
                725                 730                 735

Cys Gln Arg Gly Tyr Lys Gly Val Trp Arg Gly Asp Gly Ile Met Gln
            740                 745                 750

Thr Thr Cys Pro Cys Gly Ala Gln Ile Thr Gly His Val Lys Asn Gly
        755                 760                 765

Ser Met Arg Ile Val Gly Pro Lys Thr Cys Ser Asn Thr Trp His Gly
    770                 775                 780

Thr Phe Pro Ile Asn Ala Tyr Thr Thr Gly Pro Cys Thr Pro Ser Pro
785                 790                 795                 800

Ala Pro Asn Tyr Ser Arg Ala Leu Trp Arg Val Ala Ala Glu Glu Tyr
                805                 810                 815

Val Glu Ile Thr Arg Val Gly Asp Phe His Tyr Val Thr Gly Met Thr
            820                 825                 830

Thr Asp Asn Val Lys Cys Pro Cys Gln Val Pro Ala Pro Glu Phe Phe
        835                 840                 845

Thr Glu Leu Asp Gly Val Arg Leu His Arg Tyr Ala Pro Ala Cys Arg
    850                 855                 860

Pro Leu Leu Arg Glu Asp Val Thr Phe Gln Val Gly Leu Asn Gln Tyr
865                 870                 875                 880

Leu Val Gly Ser Gln Leu Pro Cys Glu Pro Glu Pro Asp Val Ala Val
                885                 890                 895

Leu Thr Ser Met Leu Thr Asp Pro Ser His Ile Thr Ala Glu Thr Ala
            900                 905                 910

Lys Arg Arg Leu Ala Arg Gly Ser Pro Pro Ser Leu Ala Ser Ser Ser
        915                 920                 925

Ala Ser Gln Leu Ser Ala Pro Ser Leu Lys Ala Thr Cys Thr Thr His
    930                 935                 940

His Asp Ser Pro Asp Ala Asp Leu Ile Glu Ala Asn Leu Leu Trp Arg
945                 950                 955                 960

Gln Glu Met Gly Gly Asn Ile Thr Arg Val Glu Ser Glu Asn Lys Val
                965                 970                 975

Val Ile Leu Asp Ser Phe Asp Pro Leu Arg Ala Glu Glu Asp Glu Arg
            980                 985                 990

Glu Val Ser Val Ala Ala Glu Ile Leu Arg Lys Ser Lys Lys Phe Pro
        995                 1000                1005

Pro Ala Leu Pro Ile Trp Ala Arg Pro Asp Tyr Asn Pro Pro Leu Leu
    1010                1015                1020

Glu Ser Trp Lys Ser Pro Asp Tyr Val Pro Pro Ala Val His Gly Cys
1025                1030                1035                1040

Pro Leu Pro Pro Thr Thr Gly Pro Pro Ile Pro Pro Pro Arg Lys Lys
                1045                1050                1055

Arg Thr Val Val Leu Thr Glu Ser Thr Val Ser Ser Ala Leu Ala Glu
            1060                1065                1070
```

```
Leu Ala Thr Lys Thr Phe Gly Ser Ser Gly Ser Ser Ala Val Asp Ser
        1075                1080                1085

Gly Thr Ala Thr Ala Pro Pro Asp Gln Thr Ser Asp Asp Gly Asp Lys
    1090                1095                1100

Glu Ser Asp Ile Glu Ser Tyr Ser Ser Met Pro Pro Leu Glu Gly Glu
1105                1110                1115                1120

Pro Gly Asp Pro Asp Leu Ser Asp Gly Ser Trp Ser Thr Val Ser Gly
                1125                1130                1135

Glu Ala Gly Asp Asp Ile Val Cys Cys Ser Gln His Leu Pro Tyr Ile
            1140                1145                1150

Glu Gln Gly Met Asp Val Asn Ala Ser Arg Ala Leu Ala Asn Val Tyr
        1155                1160                1165

Asp Leu Pro Asp Asp Phe Phe Pro Gln Ile Asp Asp Leu Val Arg Asp
    1170                1175                1180

Ala Lys Asp Ala Leu Glu Pro Tyr Trp Lys Ala Glu Thr Ile Lys Lys
1185                1190                1195                1200

His Val Leu Ile Ala Thr His Phe Val Asp Leu Ile Glu Asp Phe Trp
                1205                1210                1215

Gln Thr Thr Gln Gly Met Ser Gln Ile Ala Asp Ala Leu Arg Ala Val
            1220                1225                1230

Ile Pro Pro Thr Thr Val Pro Val Pro Glu Gly Phe Leu Ile Thr His
        1235                1240                1245

Ser Glu Ala Glu Glu Leu Pro Leu Asn Asp Leu Phe Ser Leu Gln Glu
    1250                1255                1260

Glu Arg Ile Val Asn Phe Gln Pro Asp Tyr Pro Ile Thr Ala Arg Ile
1265                1270                1275                1280

His Thr His Leu Arg Val Tyr Thr Lys Leu Asn Glu Gln Ala Leu Asp
                1285                1290                1295

Lys Ala Arg Arg Leu Leu Trp Trp His Tyr Asn Cys Leu Leu Trp Gly
            1300                1305                1310

Glu Ala Thr Val Thr Asn Tyr Ile Ser Arg Leu Arg Thr Trp Leu Ser
        1315                1320                1325

Thr Pro Glu Lys Tyr Arg Gly Lys Asp Ala Pro Thr Ile Glu Ala Ile
    1330                1335                1340

Thr Arg Pro Ile Gln Val Ala Gln Gly Gly Arg Asn Gln Thr Lys Gly
1345                1350                1355                1360

Thr Arg Lys Pro Arg Gly Leu Glu Pro Arg Arg Arg Lys Val Lys Thr
                1365                1370                1375

Thr Val Val Tyr Gly Arg Arg Arg Ser Lys Ser Arg Gly Arg Arg Ser
            1380                1385                1390

Ser Pro Ser Gln Arg Ala Gly Ser Pro Leu Pro Arg Asn Arg Gly Asn
        1395                1400                1405

Gln Thr Arg Ser Pro Ser Pro Arg Glu
    1410                1415
```

<210> SEQ ID NO 66
<211> LENGTH: 4254
<212> TYPE: DNA
<213> ORGANISM: Artificial Sequence
<220> FEATURE:
<223> OTHER INFORMATION: Codon opt. NS3/4A-4Bjunct-NS5A-4Bjunct-Heron HBcAg

<400> SEQUENCE: 66

```
atggccccca tcaccgccta cgcccagcag acccgcggcc tgctgggctg catcatcacc     60
```

-continued

```
agcctgaccg gccgcgacaa gaaccaggtg gagggcgagg tgcagatcgt gagcaccgcc    120
gcccagacct tcctggccac ctgcatcaac ggcgtgtgct ggaccgtgta ccacggcgcc    180
ggcacccgca ccatcgccag ccccaagggc cccgtgatcc agatgtacac caacgtggac    240
caggacctgg tgggctggcc cgcccccag ggcgcccgca gcctgacccc ctgcacctgc    300
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcat gggatctgga   2100
agctggctga gggatgtttg ggattggatt tgtaccgtcc tcaccgactt caaaacctgg   2160
ctccagtcca agctgctgcc aaagctgccc ggagtgccat tcttctcctg tcagaggggc   2220
tataaaggcg tgtggagggg cgatggaatt atgcagacta cttgcccctg tggagctcaa   2280
attactgggc acgttaagaa tggctccatg cggattgttg gcccaaaaac ctgttccaac   2340
acctggcacg gaaccttccc tattaacgct tacaccaccg gaccttgcac tccttccccc   2400
gcacctaatt attcccgggc tctctggcgg gtggcagcag aggaatatgt cgaaattacc   2460
```

-continued

```
agagtcggcg acttccacta cgtcacagga atgactacag acaacgttaa atgtccctgc   2520

caagtgcccg ctccagagtt ctttaccgaa ctcgacgggg ttaggctcca cagatacgca   2580

cccgcctgcc ggccactgct gcgggaagac gtcacattcc aggtcgggct gaaccagtac   2640

ctggtgggct ctcagctgcc ttgtgagcct gagcccgacg tggcagttct caccagcatg   2700

ctcaccgatc ctagccacat caccgctgag acagccaaac gccgcctggc tagagggtcc   2760

cctccctctc tggccagctc cagcgctagc cagctctccg caccaagcct gaaagccaca   2820

tgcactacac accacgatag ccccgacgca gacctgattg aagccaacct cctctggaga   2880

caggaaatgg gcggaaacat cactagggtc gaatccgaga ataaagtggt tattctggat   2940

agcttcgacc cactcagggc agaggaagat gagagagagg ttagcgtggc cgctgagatt   3000

ctccgcaagt ccaaaaagtt ccctcccgca ctgcccattt gggcaaggcc cgattacaat   3060

cctccactgc tcgagagctg gaagtcccct gactacgtgc caccagccgt ccacggatgc   3120

cctctgcccc ctaccacagg accaccaatt ccacccccta gaaagaaacg gaccgtggtt   3180

ctgactgagt ccaccgtgtc ctctgcactc gctgagctgg caaccaagac ctttggatcc   3240

agcggatcct ccgcagtcga ctccggcacc gctaccgccc cacccgatca aacctctgac   3300

gatggagaca aggagagcga tattgagtcc tattccagca tgccccccact cgagggagaa   3360

cccggcgacc ccgacctgag cgatgggtcc tggagcactg tgagcgggga agcaggggac   3420

gacattgtct gttgcagcca gcacctgccc tacatcgagc agggcatgga cgtgaacgcc   3480

agcagagccc tggccaacgt gtacgacctg cccgacgact tcttccccca gatcgacgac   3540

ctggtgagag acgccaagga cgccctggag ccctactgga aggccgagac catcaagaag   3600

cacgtgctga tcgccaccca cttcgtggac ttgatcgagg acttctggca gaccacccag   3660

ggcatgagcc agatcgccga cgccctgaga gccgtgatcc cccccaccac cgtgcccgtg   3720

cccgagggct tcctgatcac ccacagcgag gccgaggagc tccccctgaa cgacctgttc   3780

agtctgcagg aggagagaat cgtgaacttc cagcccgact accccatcac cgccagaatt   3840

cacacccacc tgagagtgta caccaagctg aacgagcagg ccctggacaa ggccagaaga   3900

ctgctgtggt ggcactacaa ctgcctgctg tggggcgagg ccaccgtgac caactacatc   3960

agcagactga gaacctggct gagcaccccc gagaagtaca gaggcaagga cgcccccacc   4020

atcgaggcca tcaccagacc catccaggtg gcccagggcg gcagaaacca gaccaagggc   4080

accagaaagc ccagaggcct ggagcccaga agaagaaagg tgaagaccac cgtggtgtac   4140

ggcagaagaa gaagcaagag cagaggcaga agaagcagcc ccagccagag agccggcagc   4200

cccctgccca gaaacagagg caaccagacc agaagcccca gccccagaga gtga         4254
```

<210> SEQ ID NO 67
<211> LENGTH: 1338
<212> TYPE: PRT
<213> ORGANISM: Artificial Sequence
<220> FEATURE:
<223> OTHER INFORMATION: Codon opt. NS3/4A-4Bjunct-NS5A-4Bjunct-HBV
HBcAg

<400> SEQUENCE: 67

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45
```

-continued

```
Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480
```

```
Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Gly Ser Gly Ser Trp Leu Arg
    690                 695                 700

Asp Val Trp Asp Trp Ile Cys Thr Val Leu Thr Asp Phe Lys Thr Trp
705                 710                 715                 720

Leu Gln Ser Lys Leu Leu Pro Lys Leu Pro Gly Val Pro Phe Phe Ser
                725                 730                 735

Cys Gln Arg Gly Tyr Lys Gly Val Trp Arg Gly Asp Gly Ile Met Gln
            740                 745                 750

Thr Thr Cys Pro Cys Gly Ala Gln Ile Thr Gly His Val Lys Asn Gly
        755                 760                 765

Ser Met Arg Ile Val Gly Pro Lys Thr Cys Ser Asn Thr Trp His Gly
    770                 775                 780

Thr Phe Pro Ile Asn Ala Tyr Thr Thr Gly Pro Cys Thr Pro Ser Pro
785                 790                 795                 800

Ala Pro Asn Tyr Ser Arg Ala Leu Trp Arg Val Ala Ala Glu Glu Tyr
                805                 810                 815

Val Glu Ile Thr Arg Val Gly Asp Phe His Tyr Val Thr Gly Met Thr
            820                 825                 830

Thr Asp Asn Val Lys Cys Pro Cys Gln Val Pro Ala Pro Glu Phe Phe
        835                 840                 845

Thr Glu Leu Asp Gly Val Arg Leu His Arg Tyr Ala Pro Ala Cys Arg
    850                 855                 860

Pro Leu Leu Arg Glu Asp Val Thr Phe Gln Val Gly Leu Asn Gln Tyr
865                 870                 875                 880

Leu Val Gly Ser Gln Leu Pro Cys Glu Pro Glu Pro Asp Val Ala Val
                885                 890                 895

Leu Thr Ser Met Leu Thr Asp Pro Ser His Ile Thr Ala Glu Thr Ala
```

-continued

```
            900                 905                 910

Lys Arg Arg Leu Ala Arg Gly Ser Pro Pro Ser Leu Ala Ser Ser Ser
        915                 920                 925

Ala Ser Gln Leu Ser Ala Pro Ser Leu Lys Ala Thr Cys Thr Thr His
    930                 935                 940

His Asp Ser Pro Asp Ala Asp Leu Ile Glu Ala Asn Leu Leu Trp Arg
945                 950                 955                 960

Gln Glu Met Gly Gly Asn Ile Thr Arg Val Glu Ser Glu Asn Lys Val
                965                 970                 975

Val Ile Leu Asp Ser Phe Asp Pro Leu Arg Ala Glu Glu Asp Glu Arg
            980                 985                 990

Glu Val Ser Val Ala Ala Glu Ile Leu Arg Lys Ser Lys Lys Phe Pro
        995                 1000                1005

Pro Ala Leu Pro Ile Trp Ala Arg Pro Asp Tyr Asn Pro Pro Leu Leu
    1010                1015                1020

Glu Ser Trp Lys Ser Pro Asp Tyr Val Pro Pro Ala Val His Gly Cys
1025                1030                1035                1040

Pro Leu Pro Pro Thr Thr Gly Pro Pro Ile Pro Pro Pro Arg Lys Lys
                1045                1050                1055

Arg Thr Val Val Leu Thr Glu Ser Thr Val Ser Ser Ala Leu Ala Glu
            1060                1065                1070

Leu Ala Thr Lys Thr Phe Gly Ser Ser Gly Ser Ser Ala Val Asp Ser
        1075                1080                1085

Gly Thr Ala Thr Ala Pro Pro Asp Gln Thr Ser Asp Asp Gly Asp Lys
    1090                1095                1100

Glu Ser Asp Ile Glu Ser Tyr Ser Ser Met Pro Pro Leu Glu Gly Glu
1105                1110                1115                1120

Pro Gly Asp Pro Asp Leu Ser Asp Gly Ser Trp Ser Thr Val Ser Gly
                1125                1130                1135

Glu Ala Gly Asp Asp Ile Val Cys Cys Ser Gln His Leu Pro Tyr Ile
            1140                1145                1150

Glu Gln Gly Met Asp Ile Asp Pro Tyr Lys Glu Phe Gly Ala Thr Val
        1155                1160                1165

Glu Leu Leu Ser Phe Leu Pro Ser Asp Phe Phe Pro Ser Val Arg Asp
    1170                1175                1180

Leu Leu Asp Thr Ala Ser Ala Leu Tyr Arg Glu Ala Leu Glu Ser Pro
1185                1190                1195                1200

Glu His Cys Ser Pro His His Thr Ala Leu Arg Gln Ala Ile Leu Cys
                1205                1210                1215

Trp Gly Glu Leu Met Thr Leu Ala Thr Trp Val Gly Val Asn Leu Glu
            1220                1225                1230

Asp Pro Ala Ser Arg Asp Leu Val Val Ser Tyr Val Asn Thr Asn Met
        1235                1240                1245

Gly Leu Lys Phe Arg Gln Leu Leu Trp Phe His Ile Ser Cys Leu Thr
    1250                1255                1260

Phe Gly Arg Glu Thr Val Ile Glu Tyr Leu Val Ser Phe Gly Val Trp
1265                1270                1275                1280

Ile Arg Thr Pro Pro Ala Tyr Arg Pro Pro Asn Ala Pro Ile Leu Ser
                1285                1290                1295

Thr Leu Pro Glu Thr Thr Val Val Arg Arg Arg Gly Arg Ser Pro Arg
            1300                1305                1310

Arg Arg Thr Pro Ser Pro Arg Arg Arg Arg Ser Gln Ser Pro Arg Arg
        1315                1320                1325
```

```
Arg Arg Ser Gln Ser Arg Glu Ser Gln Cys
    1330                1335


<210> SEQ ID NO 68
<211> LENGTH: 4017
<212> TYPE: DNA
<213> ORGANISM: Artificial Sequence
<220> FEATURE:
<223> OTHER INFORMATION: Codon opt. NS3/4A-4Bjunct-NS5A-4Bjunct-HBV
      HBcAg

<400> SEQUENCE: 68

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgcccccccag ggcgcccgca gcctgacccc ctgcacctgc   300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatcccccct ggaggccatc  1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg  1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980
```

-continued

```
atcgtgctga gcggcaagcc cgccatcatc cccgaccgcg aggtgctgta ccgcgagttc   2040
gacgagatgg aggagtgcag ccagcacctg ccctacatcg agcagggcat gggatctgga   2100
agctggctga gggatgtttg ggattggatt tgtaccgtcc tcaccgactt caaaacctgg   2160
ctccagtcca agctgctgcc aaagctgccc ggagtgccat tcttctcctg tcagaggggc   2220
tataaaggcg tgtggagggg cgatggaatt atgcagacta cttgcccctg tggagctcaa   2280
attactgggc acgttaagaa tggctccatg cggattgttg gcccaaaaac ctgttccaac   2340
acctggcacg gaaccttccc tattaacgct tacaccaccg gaccttgcac tccttccccc   2400
gcacctaatt attcccgggc tctctggcgg gtggcagcag aggaatatgt cgaaattacc   2460
agagtcggcg acttccacta cgtcacagga atgactacag acaacgttaa atgtccctgc   2520
caagtgcccg ctccagagtt ctttaccgaa ctcgacgggg ttaggctcca cagatacgca   2580
cccgcctgcc ggccactgct gcgggaagac gtcacattcc aggtcgggct gaaccagtac   2640
ctggtgggct ctcagctgcc ttgtgagcct gagcccgacg tggcagttct caccagcatg   2700
ctcaccgatc ctagccacat caccgctgag acagccaaac gccgcctggc tagagggtcc   2760
cctccctctc tggccagctc cagcgctagc cagctctccg caccaagcct gaaagccaca   2820
tgcactacac accacgatag ccccgacgca gacctgattg aagccaacct cctctggaga   2880
caggaaatgg gcggaaacat cactagggtc gaatccgaga ataaagtggt tattctggat   2940
agcttcgacc cactcagggc agaggaagat gagagagagg ttagcgtggc cgctgagatt   3000
ctccgcaagt ccaaaaagtt ccctcccgca ctgcccattt gggcaaggcc cgattacaat   3060
cctccactgc tcgagagctg gaagtcccct gactacgtgc caccagccgt ccacggatgc   3120
cctctgcccc ctaccacagg accaccaatt ccacccccta gaaagaaacg gaccgtggtt   3180
ctgactgagt ccaccgtgtc ctctgcactc gctgagctgg caaccaagac ctttggatcc   3240
agcggatcct ccgcagtcga ctccggcacc gctaccgccc cacccgatca aacctctgac   3300
gatggagaca aggagagcga tattgagtcc tattccagca tgcccccact cgagggagaa   3360
cccggcgacc ccgacctgag cgatgggtcc tggagcactg tgagcgggga agcaggggac   3420
gacattgtct gttgcagcca gcacctgccc tacatcgagc agggcatgga catcgacccc   3480
tacaaggagt tcggcgccac cgtggagctg ctgagcttcc tgcccagcga cttcttcccc   3540
agcgtgagag acctgctgga caccgccagc gccctgtaca gagaggccct ggagagcccc   3600
gagcactgca gcccccacca caccgccctg agacaggcca tcctgtgctg gggcgagctg   3660
atgaccctgg ccacctgggt gggcgtgaac ctggaggacc ccgccagcag agacctggtg   3720
gtgagctacg tgaacaccaa catgggcctg aagttcagac agctgctgtg gttccacatc   3780
agctgcctga ccttcggcag agagaccgtg atcgagtacc tggtgagctt cggcgtgtgg   3840
atcagaaccc cccccgccta cagacccccc aacgccccca tcctgagcac cctgcccgag   3900
accaccgtgg tgagaagaag aggcagaagc cccagaagaa gaacccccag ccccagaaga   3960
agaagaagcc agagccccag aagaagaaga agccagagca gagagagcca gtgctag      4017
```

<210> SEQ ID NO 69
<211> LENGTH: 262
<212> TYPE: PRT
<213> ORGANISM: Artificial Sequence
<220> FEATURE:
<223> OTHER INFORMATION: Codon optimized Stork HBcAg with HBV HBcAg

<400> SEQUENCE: 69

```
Met Asp Val Asn Ala Ser Arg Ala Leu Ala Asn Val Tyr Asp Leu Pro
 1               5                  10                  15
```

```
Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Thr Pro Val Pro Asp Gly Tyr Leu Ile Ser His Asn Glu Ala
                85                  90                  95

Gln Glu Leu Pro Leu Asn Asp Leu Phe Val Leu Gln Glu Glu Arg Ile
            100                 105                 110

Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ser Asn
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Ser Arg Asn Gln Thr Lys Gly Val Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Gly Arg Arg Ser Ser Pro Ser
225                 230                 235                 240

Gln Arg Ala Gly Ser Pro Ile Pro Arg Asn Arg Glu Asn Gln Ser Arg
                245                 250                 255

Ser Ser Ser Pro Arg Glu
            260


<210> SEQ ID NO 70
<211> LENGTH: 262
<212> TYPE: PRT
<213> ORGANISM: Artificial Sequence
<220> FEATURE:
<223> OTHER INFORMATION: Codon optimized Stork HBcAg with HBV HBcAg

<400> SEQUENCE: 70

Met Asp Val Asn Ala Ser Arg Ala Leu Ala Asn Val Tyr Asp Leu Pro
 1               5                  10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Val Pro Val Pro Glu Gly Phe Leu Ile Thr His Ser Glu Ala
                85                  90                  95

Glu Glu Leu Pro Leu Asn Asp Leu Phe Ser Leu Gln Glu Glu Arg Ile
            100                 105                 110
```

```
Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Gly Arg Asn Gln Thr Lys Gly Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Gly Arg Arg Ser Ser Pro Ser
225                 230                 235                 240

Gln Arg Ala Gly Ser Pro Leu Pro Arg Asn Arg Gly Asn Gln Thr Arg
                245                 250                 255

Ser Pro Ser Pro Arg Glu
            260
```

<210> SEQ ID NO 71
<211> LENGTH: 552
<212> TYPE: DNA
<213> ORGANISM: Artificial Sequence
<220> FEATURE:
<223> OTHER INFORMATION: wild-type HBcAg

<400> SEQUENCE: 71

```
atggacatcg acccttataa agaatttgga gctactgtgg agttactctc gtttttgccc      60

tccgacttct ttccttcagt acgagatctt ctagataccg cctcagctct gtatcgggaa     120

gccttagagt ctcctgagca ttgttcacct caccatactg cactcaggca agcaattctt     180

tgctgggggg aactaatgac tctagctacc tgggtgggtg ttaatttgga agatccagcg     240

tctagagacc tagtagtcag ttatgtcaac actaatatgg gcctaaagtt caggcaactc     300

ttgtggtttc acatttcttg tctcactttt ggaagagaaa cagttataga gtatttggtg     360

tctttcggag tgtggattcg cactcctcca gcttatagac caccaaatgc ccctatccta     420

tcaacacttc cggagactac tgttgttaga cgacgaggca ggtcccctag aagaagaact     480

ccctcgcctc gcagacgaag gtctcaatcg ccgcgtcgca gaagatctca atctcgggaa     540

tctcaatgtt ag                                                         552
```

<210> SEQ ID NO 72
<211> LENGTH: 869
<212> TYPE: PRT
<213> ORGANISM: Artificial Sequence
<220> FEATURE:
<223> OTHER INFORMATION: CONSTR-1 NS3/4A-HBcAg

<400> SEQUENCE: 72

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
```

-continued

```
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480
```

```
Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865
```

<210> SEQ ID NO 73
<211> LENGTH: 2610
<212> TYPE: DNA
<213> ORGANISM: Artificial Sequence -continued
<220> FEATURE:
<223> OTHER INFORMATION: CONSTR-1 NS3/4A-HBcAg

<400> SEQUENCE: 73
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta ccacggcgcc 180
ggcacccgca ccatcgccag ccccaagggc cccgtgatcc agatgtacac caacgtggac 240
caggacctgg tgggctggcc cgcccccag ggcgcccgca gcctgacccc ctgcacctgc 300
ggcagcagcg acctgtacct ggtgacccgc cacgccgacg tgatccccgt gcgccgccgc 360
ggcgacggcc gcggcagcct gctgagcccc cgccccatca gctacctgaa gggcagcagc 420
ggcggccccc tgctgtgccc cgccggccac gccgtgggca tcttccgcgc cgccgtgtgc 480
acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccacccccc cggcagcgtg accgtgcccc accccaacat cgaggaggtg 1020
gccctgagca ccaccggcga gatccccttc tacggcaagg ccatccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggccccccggc 1440 gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800 taccgcctgg gcgccgtgca gaacgaggtg accctgaccc accccgtgac caagtacatc 1860
atgacctgca tgagcgccga cctggaggtg gtgacccca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcat ggacatcgac ccctacaagg agttcggcgc caccgtggag 2100
ctgctgagct tcctgcccag cgacttcttc cccagcgtgc gcgacctgct ggacaccgcc 2160
agcgccctgt accgcgaggc cctggagagc cccgagcact gcagccccca ccacaccgcc 2220
ctgcgccagg ccatcctgtg ctggggcgag ctgatgaccc tggccacctg ggtgggcgtg 2280

```
aacctggagg accccgccag ccgcgacctg gtggtgagct acgtgaacac caacatgggc   2340

ctgaagttcc gccagctgct gtggttccac atcagctgcc tgaccttcgg ccgcgagacc   2400

gtgatcgagt acctggtgag cttcggcgtg tggatccgca ccccccccgc ctaccgcccc   2460

cccaacgccc ccatcctgag caccctgccc gagaccaccg tggtgcgccg ccgcggccgc   2520

agcccccgcc gccgcacccc cagcccccgc cgccgccgca gccagagccc ccgccgccgc   2580

cgcagccaga gccgcgagag ccagtgctag                                     2610
```

```
<210> SEQ ID NO 74
<211> LENGTH: 869
<212> TYPE: PRT
<213> ORGANISM: Artificial Sequence
<220> FEATURE:
<223> OTHER INFORMATION: CONSTR-2 Mutant(catalytic triade)NS3/4A-HBcAg

<400> SEQUENCE: 74

Met Ala Pro Ile Thr Ala Tyr Ala Gln Gln Thr Arg Gly Leu Leu Gly
 1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr Ala Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Ala Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300
```

-continued

Gly Thr Val Leu Asp Gln Ala Glu Thr Ala Gly Ala Arg Leu Thr Val
305 310 315 320

Leu Ala Thr Ala Thr Pro Pro Gly Ser Val Thr Val Pro His Pro Asn
325 330 335

Ile Glu Glu Val Ala Leu Ser Thr Thr Gly Glu Ile Pro Phe Tyr Gly
340 345 350

Lys Ala Ile Pro Leu Glu Ala Ile Lys Gly Gly Arg His Leu Ile Phe
355 360 365

Cys His Ser Lys Lys Lys Cys Asp Glu Leu Ala Ala Lys Leu Val Ala
370 375 380

Leu Gly Val Asn Ala Val Ala Tyr Tyr Arg Gly Leu Asp Val Ser Val
385 390 395 400

Ile Pro Thr Ser Gly Asp Val Val Val Val Ala Thr Asp Ala Leu Met
405 410 415

Thr Gly Phe Thr Gly Asp Phe Asp Ser Val Ile Asp Cys Asn Thr Cys
420 425 430

Val Thr Gln Thr Val Asp Phe Ser Leu Asp Pro Thr Phe Thr Ile Glu
435 440 445

Thr Ile Thr Leu Pro Gln Asp Ala Val Ser Arg Thr Gln Arg Arg Gly
450 455 460

Arg Thr Gly Arg Gly Lys Pro Gly Ile Tyr Arg Phe Val Ala Pro Gly
465 470 475 480

Glu Arg Pro Ser Gly Met Phe Asp Ser Ser Val Leu Cys Glu Cys Tyr
485 490 495

Asp Ala Gly Cys Ala Trp Tyr Glu Leu Thr Pro Ala Glu Thr Thr Val
500 505 510

Arg Leu Arg Ala Tyr Met Asn Thr Pro Gly Leu Pro Val Cys Gln Asp
515 520 525

His Leu Glu Phe Trp Glu Gly Val Phe Thr Gly Leu Thr His Ile Asp
530 535 540

Ala His Phe Leu Ser Gln Thr Lys Gln Ser Gly Glu Asn Leu Pro Tyr
545 550 555 560

Leu Val Ala Tyr Gln Ala Thr Val Cys Ala Arg Ala Gln Ala Pro Pro
565 570 575

Pro Ser Trp Asp Gln Met Trp Lys Cys Leu Ile Arg Leu Lys Pro Thr
580 585 590

Leu His Gly Pro Thr Pro Leu Leu Tyr Arg Leu Gly Ala Val Gln Asn
595 600 605

Glu Val Thr Leu Thr His Pro Val Thr Lys Tyr Ile Met Thr Cys Met
610 615 620

Ser Ala Asp Leu Glu Val Val Thr Ser Thr Trp Val Leu Val Gly Gly
625 630 635 640

Val Leu Ala Ala Leu Ala Ala Tyr Cys Leu Ser Thr Gly Cys Val Val
645 650 655

Ile Val Gly Arg Ile Val Leu Ser Gly Lys Pro Ala Ile Ile Pro Asp
660 665 670

Arg Glu Val Leu Tyr Arg Glu Phe Asp Glu Met Glu Glu Cys Met Asp
675 680 685

Ile Asp Pro Tyr Lys Glu Phe Gly Ala Thr Val Glu Leu Leu Ser Phe
690 695 700

Leu Pro Ser Asp Phe Phe Pro Ser Val Arg Asp Leu Leu Asp Thr Ala
705 710 715 720

Ser Ala Leu Tyr Arg Glu Ala Leu Glu Ser Pro Glu His Cys Ser Pro
725 730 735

-continued

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865

<210> SEQ ID NO 75
<211> LENGTH: 2610
<212> TYPE: DNA
<213> ORGANISM: Artificial Sequence
<220> FEATURE:
<223> OTHER INFORMATION: CONSTR-2 Mutant(catalytic triade)NS3/4A-HBcAg

<400> SEQUENCE: 75
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta cgccggcgcc 180
ggcacccgca ccatcgccag ccccaagggc cccgtgatcc agatgtacac caacgtggac 240
caggccctgg tgggctggcc cgccccccag ggcgcccgca gcctgacccc ctgcacctgc 300
ggcagcagcg acctgtacct ggtgacccgc cacgccgacg tgatccccgt gcgccgccgc 360
ggcgacggcc gcggcagcct gctgagcccc cgccccatca gctacctgaa gggcagcagc 420
ggcggccccc tgctgtgccc cgccggccac gccgtgggca tcttccgcgc cgccgtgtgc 480
acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccacccccc cggcagcgtg accgtgcccc accccaacat cgaggaggtg 1020
gccctgagca ccaccggcga gatccccttc tacggcaagg ccatccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260

```
ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacatcgac ccctacaagg agttcggcgc caccgtggag   2100

ctgctgagct tcctgcccag cgacttcttc cccagcgtgc gcgacctgct ggacaccgcc   2160

agcgccctgt accgcgaggc cctggagagc cccgagcact gcagccccca ccacaccgcc   2220

ctgcgccagg ccatcctgtg ctggggcgag ctgatgaccc tggccacctg ggtgggcgtg   2280

aacctggagg accccgccag ccgcgacctg gtggtgagct acgtgaacac caacatgggc   2340

ctgaagttcc gccagctgct gtggttccac atcagctgcc tgaccttcgg ccgcgagacc   2400

gtgatcgagt acctggtgag cttcggcgtg tggatccgca cccccccccgc ctaccgcccc   2460

cccaacgccc ccatcctgag caccctgccc gagaccaccg tggtgcgccg ccgcggccgc   2520

agcccccgcc gccgcacccc cagcccccgc cgccgccgca gccagagccc ccgccgccgc   2580

cgcagccaga gccgcgagag ccagtgctag                                    2610
```

```
<210> SEQ ID NO 76
<211> LENGTH: 869
<212> TYPE: PRT
<213> ORGANISM: Artificial Sequence
<220> FEATURE:
<223> OTHER INFORMATION: CONSTR-3 NS3/4A-HBcAg (NS3 and NS4A-HBcAg
      fusion)

<400> SEQUENCE: 76

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125
```

```
Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
```

```
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865
```

<210> SEQ ID NO 77
<211> LENGTH: 2610
<212> TYPE: DNA
<213> ORGANISM: Artificial Sequence
<220> FEATURE:
<223> OTHER INFORMATION: CONSTR-3 NS3/4A-HBcAg (NS3 and NS4A-HBcAg fusion)

<400> SEQUENCE: 77

```
atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240
```

-continued

```
caggacctgg tgggctggcc cgccccccag ggcgcccgca gcctgacccc ctgcacctgc    300
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac ccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcat ggacatcgac ccctacaagg agttcggcgc caccgtggag   2100
ctgctgagct tcctgcccag cgacttcttc cccagcgtgc gcgacctgct ggacaccgcc   2160
agcgccctgt accgcgaggc cctggagagc cccgagcact gcagccccca ccacaccgcc   2220
ctgcgccagg ccatcctgtg ctggggcgag ctgatgaccc tggccacctg ggtgggcgtg   2280
aacctggagg accccgccag ccgcgacctg gtggtgagct acgtgaacac caacatgggc   2340
ctgaagttcc gccagctgct gtggttccac atcagctgcc tgaccttcgg ccgcgagacc   2400
gtgatcgagt acctggtgag cttcggcgtg tggatccgca cccccccgc ctaccgcccc   2460
cccaacgccc ccatcctgag caccctgccc gagaccaccg tggtgcgccg ccgcggccgc   2520
agcccccgcc gccgcacccc cagcccccgc cgccgccgca gccagagccc ccgccgccgc   2580
cgcagccaga gccgcgagag ccagtgctag                                    2610
```

<210> SEQ ID NO 78
<211> LENGTH: 879
<212> TYPE: PRT
<213> ORGANISM: Artificial Sequence
<220> FEATURE:
<223> OTHER INFORMATION: CONSTR-4 NS3/4A-4Bjunct-HBcAg

<400> SEQUENCE: 78

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365
```

-continued

```
Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Pro Glu His Cys Ser Pro His His Thr Ala Leu Arg
            740                 745                 750

Gln Ala Ile Leu Cys Trp Gly Glu Leu Met Thr Leu Ala Thr Trp Val
        755                 760                 765

Gly Val Asn Leu Glu Asp Pro Ala Ser Arg Asp Leu Val Val Ser Tyr
    770                 775                 780

Val Asn Thr Asn Met Gly Leu Lys Phe Arg Gln Leu Leu Trp Phe His
785                 790                 795                 800
```

```
Ile Ser Cys Leu Thr Phe Gly Arg Glu Thr Val Ile Glu Tyr Leu Val
                805                 810                 815

Ser Phe Gly Val Trp Ile Arg Thr Pro Pro Ala Tyr Arg Pro Pro Asn
            820                 825                 830

Ala Pro Ile Leu Ser Thr Leu Pro Glu Thr Thr Val Val Arg Arg Arg
        835                 840                 845

Gly Arg Ser Pro Arg Arg Arg Thr Pro Ser Pro Arg Arg Arg Arg Ser
    850                 855                 860

Gln Ser Pro Arg Arg Arg Arg Ser Gln Ser Arg Glu Ser Gln Cys
865                 870                 875


<210> SEQ ID NO 79
<211> LENGTH: 2640
<212> TYPE: DNA
<213> ORGANISM: Artificial Sequence
<220> FEATURE:
<223> OTHER INFORMATION: CONSTR-4 NS3/4A-4Bjunct-HBcAg

<400> SEQUENCE: 79

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620
```

```
acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac ccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcat ggacatcgac   2100

ccctacaagg agttcggcgc caccgtggag ctgctgagct tcctgcccag cgacttcttc   2160

cccagcgtgc gcgacctgct ggacaccgcc agcgccctgt accgcgaggc cctggagagc   2220

cccgagcact gcagccccca ccacaccgcc ctgcgccagg ccatcctgtg ctggggcgag   2280

ctgatgaccc tggccacctg ggtgggcgtg aacctggagg accccgccag ccgcgacctg   2340

gtggtgagct acgtgaacac caacatgggc ctgaagttcc gccagctgct gtggttccac   2400

atcagctgcc tgaccttcgg ccgcgagacc gtgatcgagt acctggtgag cttcggcgtg   2460

tggatccgca cccccccgc ctaccgcccc cccaacgccc ccatcctgag caccctgccc   2520

gagaccaccg tggtgcgccg ccgcggccgc agcccccgcc gccgcacccc cagcccccgc   2580

cgccgccgca gccagagccc ccgccgccgc cgcagccaga gccgcgagag ccagtgctag   2640
```

```
<210> SEQ ID NO 80
<211> LENGTH: 933
<212> TYPE: PRT
<213> ORGANISM: Artificial Sequence
<220> FEATURE:
<223> OTHER INFORMATION: CONSTR-5 NS3/4A-HBcAg Fragments

<400> SEQUENCE: 80

Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190
```

```
Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620
```

```
Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Ser Ala Asp Leu Glu Val Val Thr Ser Thr Trp Val
            740                 745                 750

Leu Val Gly Gly Val Leu Pro Glu His Cys Ser Pro His His Thr Ala
        755                 760                 765

Leu Arg Gln Ala Ile Leu Cys Trp Gly Glu Leu Met Thr Leu Ala Thr
    770                 775                 780

Trp Val Gly Val Asn Leu Glu Asp Pro Ala Ser Arg Asp Leu Val Val
785                 790                 795                 800

Ser Ser Ala Asp Leu Glu Val Val Thr Ser Thr Trp Val Leu Val Gly
                805                 810                 815

Gly Val Leu Tyr Val Asn Thr Asn Met Gly Leu Lys Phe Arg Gln Leu
            820                 825                 830

Leu Trp Phe His Ile Ser Cys Leu Thr Phe Gly Arg Glu Thr Val Ile
        835                 840                 845

Glu Tyr Leu Val Ser Phe Gly Val Trp Ile Arg Thr Pro Pro Ala Tyr
    850                 855                 860

Arg Pro Pro Asn Ala Pro Ile Leu Ser Ser Ala Asp Leu Glu Val Val
865                 870                 875                 880

Thr Ser Thr Trp Val Leu Val Gly Gly Val Leu Thr Leu Pro Glu Thr
                885                 890                 895

Thr Val Val Arg Arg Arg Gly Arg Ser Pro Arg Arg Arg Thr Pro Ser
            900                 905                 910

Pro Arg Arg Arg Arg Ser Gln Ser Pro Arg Arg Arg Arg Ser Gln Ser
        915                 920                 925

Arg Glu Ser Gln Cys
    930
```

<210> SEQ ID NO 81
<211> LENGTH: 2802
<212> TYPE: DNA
<213> ORGANISM: Artificial Sequence
<220> FEATURE:
<223> OTHER INFORMATION: CONSTR-5 NS3/4A-HBcAg Fragments

<400> SEQUENCE: 81

```
atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgccccccag ggcgcccgca gcctgacccc ctgcacctgc     300
```

-continued

```
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac ccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcat ggacatcgac   2100
ccctacaagg agttcggcgc caccgtggag ctgctgagct tcctgcccag cgacttcttc   2160
cccagcgtgc gcgacctgct ggacaccgcc agcgccctgt accgcgaggc cctggagagc   2220
agcgccgacc tggaggtggt gaccagcacc tgggtgctgg tgggcggcgt gctgcccgag   2280
cactgcagcc cccaccacac cgccctgcgc caggccatcc tgtgctgggg cgagctgatg   2340
accctggcca cctgggtggg cgtgaacctg gaggaccccg ccagccgcga cctggtggtg   2400
agcagcgccg acctggaggt ggtgaccagc acctgggtgc tggtgggcgg cgtgctgtac   2460
gtgaacacca acatgggcct gaagttccgc cagctgctgt ggttccacat cagctgcctg   2520
accttcggcc gcgagaccgt gatcgagtac ctggtgagct tcggcgtgtg gatccgcacc   2580
ccccccgcct accgcccccc caacgccccc atcctgagca gcgccgacct ggaggtggtg   2640
accagcacct gggtgctggt gggcggcgtg ctgaccctgc ccgagaccac cgtggtgcgc   2700
```

```
cgccgcggcc gcagcccccg ccgccgcacc cccagccccc gccgccgccg cagccagagc   2760

ccccgccgcc gccgcagcca gagccgcgag agccagtgct ag                      2802


<210> SEQ ID NO 82
<211> LENGTH: 933
<212> TYPE: PRT
<213> ORGANISM: Artificial Sequence
<220> FEATURE:
<223> OTHER INFORMATION: CONSTR-5 NS3/4A-HBcAg Fragments

<400> SEQUENCE: 82

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350
```

-continued

```
Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Pro Glu His Cys Ser Pro His His Thr Ala Leu Arg
        755                 760                 765

Gln Ala Ile Leu Cys Trp Gly Glu Leu Met Thr Leu Ala Thr Trp Val
```

-continued

```
    770                 775                 780

Gly Val Asn Leu Glu Asp Pro Ala Ser Arg Asp Leu Val Val Ser Ser
785                 790                 795                 800

Ala Asp Leu Glu Val Val Thr Ser Thr Trp Val Leu Val Gly Gly Val
                805                 810                 815

Leu Tyr Val Asn Thr Asn Met Gly Leu Lys Phe Arg Gln Leu Leu Trp
            820                 825                 830

Phe His Ile Ser Cys Leu Thr Phe Gly Arg Glu Thr Val Ile Glu Tyr
        835                 840                 845

Leu Val Ser Phe Gly Val Trp Ile Arg Thr Pro Pro Ala Tyr Arg Pro
    850                 855                 860

Pro Asn Ala Pro Ile Leu Ser Ser Ala Asp Leu Glu Val Val Thr Ser
865                 870                 875                 880

Thr Trp Val Leu Val Gly Gly Val Leu Met Asp Ile Asp Pro Tyr Lys
                885                 890                 895

Glu Phe Gly Ala Thr Val Glu Leu Leu Ser Phe Leu Pro Ser Asp Phe
            900                 905                 910

Phe Pro Ser Val Arg Asp Leu Leu Asp Thr Ala Ser Ala Leu Tyr Arg
        915                 920                 925

Glu Ala Leu Glu Ser
    930


<210> SEQ ID NO 83
<211> LENGTH: 2802
<212> TYPE: DNA
<213> ORGANISM: Artificial Sequence
<220> FEATURE:
<223> OTHER INFORMATION: CONSTR-6 NS3/4A-HBcAg Fragments

<400> SEQUENCE: 83

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140
```

-continued

```
aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcac cctgcccgag   2100

accaccgtgg tgcgccgccg cggccgcagc cccccgccgcc gcacccccag cccccgccgc   2160

cgccgcagcc agagcccccg ccgccgccgc agccagagcc gcgagagcca gtgcagcgcc   2220

gacctggagg tggtgaccag cacctgggtg ctggtgggcg gcgtgctgcc cgagcactgc   2280

agcccccacc acaccgccct gcgccaggcc atcctgtgct ggggcgagct gatgaccctg   2340

gccacctggg tgggcgtgaa cctggaggac cccgccagcc gcgacctggt ggtgagcagc   2400

gccgacctgg aggtggtgac cagcacctgg gtgctggtgg gcggcgtgct gtacgtgaac   2460

accaacatgg gcctgaagtt ccgccagctg ctgtggttcc acatcagctg cctgaccttc   2520

ggccgcgaga ccgtgatcga gtacctggtg agcttcggcg tgtggatccg cacccccccc   2580

gcctaccgcc cccccaacgc ccccatcctg agcagcgccg acctggaggt ggtgaccagc   2640

acctgggtgc tggtgggcgg cgtgctgatg gacatcgacc cctacaagga gttcggcgcc   2700

accgtggagc tgctgagctt cctgcccagc gacttcttcc ccagcgtgcg cgacctgctg   2760

gacaccgcca gcgccctgta ccgcgaggcc ctggagagct ag                      2802
```

<210> SEQ ID NO 84
<211> LENGTH: 933
<212> TYPE: PRT
<213> ORGANISM: Artificial Sequence
<220> FEATURE:
<223> OTHER INFORMATION: CONSTR-7 NS3/4A-HBcAg Fragments

<400> SEQUENCE: 84

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80
```

-continued

```
Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
```

```
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Tyr Val Asn Thr Asn Met Gly Leu Lys Phe Arg Gln
        755                 760                 765

Leu Leu Trp Phe His Ile Ser Cys Leu Thr Phe Gly Arg Glu Thr Val
    770                 775                 780

Ile Glu Tyr Leu Val Ser Phe Gly Val Trp Ile Arg Thr Pro Pro Ala
785                 790                 795                 800

Tyr Arg Pro Pro Asn Ala Pro Ile Leu Ser Ser Ala Asp Leu Glu Val
                805                 810                 815

Val Thr Ser Thr Trp Val Leu Val Gly Gly Val Leu Pro Glu His Cys
            820                 825                 830

Ser Pro His His Thr Ala Leu Arg Gln Ala Ile Leu Cys Trp Gly Glu
        835                 840                 845

Leu Met Thr Leu Ala Thr Trp Val Gly Val Asn Leu Glu Asp Pro Ala
    850                 855                 860

Ser Arg Asp Leu Val Val Ser Ser Ala Asp Leu Glu Val Val Thr Ser
865                 870                 875                 880

Thr Trp Val Leu Val Gly Gly Val Leu Met Asp Ile Asp Pro Tyr Lys
                885                 890                 895

Glu Phe Gly Ala Thr Val Glu Leu Leu Ser Phe Leu Pro Ser Asp Phe
            900                 905                 910

Phe Pro Ser Val Arg Asp Leu Leu Asp Thr Ala Ser Ala Leu Tyr Arg
        915                 920                 925
```

Glu Ala Leu Glu Ser
930

<210> SEQ ID NO 85
<211> LENGTH: 2802
<212> TYPE: DNA
<213> ORGANISM: Artificial Sequence
<220> FEATURE:
<223> OTHER INFORMATION: CONSTR-7 NS3/4A-HBcAg Fragments

<400> SEQUENCE: 85
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta ccacggcgcc 180
ggcacccgca ccatcgccag ccccaagggc cccgtgatcc agatgtacac caacgtggac 240
caggacctgg tgggctggcc cgcccccag ggcgcccgca gcctgacccc ctgcacctgc 300
ggcagcagcg acctgtacct ggtgacccgc cacgccgacg tgatccccgt gcgccgccgc 360
ggcgacggcc gcggcagcct gctgagcccc cgccccatca gctacctgaa gggcagcagc 420
ggcggccccc tgctgtgccc cgccggccac gccgtgggca tcttccgcgc cgccgtgtgc 480
acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccacccccc cggcagcgtg accgtgcccc accccaacat cgaggaggtg 1020
gccctgagca ccaccggcga gatccccttc tacggcaagg ccatcccct ggaggccatc 1080 aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggcccccggc 1440
gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800 taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcag ccagcacctg ccctacatcg agcagggcac cctgcccgag 2100
accaccgtgg tgcgccgccg cggccgcagc ccccgccgcc gcacccccag cccccgccgc 2160
cgccgcagcc agagcccccg ccgccgccgc agccagagcc gcgagagcca gtgcagcgcc 2220
gacctggagg tggtgaccag cacctgggtg ctggtgggcg gcgtgctgta cgtgaacacc 2280
aacatgggcc tgaagttccg ccagctgctg tggttccaca tcagctgcct gaccttcggc 2340
cgcgagaccg tgatcgagta cctggtgagc ttcggcgtgt ggatccgcac cccccccgcc 2400
taccgccccc ccaacgcccc catcctgagc agcgccgacc tggaggtggt gaccagcacc 2460
tgggtgctgg tgggcggcgt gctgcccgag cactgcagcc cccaccacac cgccctgcgc 2520
caggccatcc tgtgctgggg cgagctgatg accctggcca cctgggtggg cgtgaacctg 2580
gaggaccccg ccagccgcga cctggtggtg agcagcgccg acctggaggt ggtgaccagc 2640
acctgggtgc tggtgggcgg cgtgctgatg gacatcgacc cctacaagga gttcggcgcc 2700
accgtggagc tgctgagctt cctgcccagc gacttcttcc ccagcgtgcg cgacctgctg 2760
gacaccgcca gcgccctgta ccgcgaggcc ctggagagct ag 2802

<210> SEQ ID NO 86
<211> LENGTH: 933
<212> TYPE: PRT
<213> ORGANISM: Artificial Sequence
<220> FEATURE:
<223> OTHER INFORMATION: CONSTR-8 NS3/4A-HBcAg Fragments

<400> SEQUENCE: 86

Met Ala Pro Ile Thr Ala Tyr Ala Gln Gln Thr Arg Gly Leu Leu Gly
1 5 10 15

Cys Ile Ile Thr Ser Leu Thr Gly Arg Asp Lys Asn Gln Val Glu Gly
20 25 30

Glu Val Gln Ile Val Ser Thr Ala Ala Gln Thr Phe Leu Ala Thr Cys
35 40 45

Ile Asn Gly Val Cys Trp Thr Val Tyr His Gly Ala Gly Thr Arg Thr
50 55 60

Ile Ala Ser Pro Lys Gly Pro Val Ile Gln Met Tyr Thr Asn Val Asp
65 70 75 80

Gln Asp Leu Val Gly Trp Pro Ala Pro Gln Gly Ala Arg Ser Leu Thr
85 90 95

Pro Cys Thr Cys Gly Ser Ser Asp Leu Tyr Leu Val Thr Arg His Ala
100 105 110

Asp Val Ile Pro Val Arg Arg Arg Gly Asp Gly Arg Gly Ser Leu Leu
115 120 125

Ser Pro Arg Pro Ile Ser Tyr Leu Lys Gly Ser Ser Gly Gly Pro Leu
130 135 140

Leu Cys Pro Ala Gly His Ala Val Gly Ile Phe Arg Ala Ala Val Cys
145 150 155 160

Thr Arg Gly Val Ala Lys Ala Val Asp Phe Ile Pro Val Glu Ser Leu
165 170 175

Glu Thr Thr Met Arg Ser Pro Val Phe Ser Asp Asn Ser Ser Pro Pro
180 185 190

Ala Val Pro Gln Ser Tyr Gln Val Ala His Leu His Ala Pro Thr Gly
195 200 205

Ser Gly Lys Ser Thr Lys Val Pro Ala Ala Tyr Ala Ala Gln Gly Tyr
210 215 220

Lys Val Leu Val Leu Asn Pro Ser Val Ala Ala Thr Met Gly Phe Gly

-continued

```
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655
```

```
Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Tyr Val Asn Thr Asn Met Gly Leu Lys Phe Arg Gln
        755                 760                 765

Leu Leu Trp Phe His Ile Ser Cys Leu Thr Phe Gly Arg Glu Thr Val
    770                 775                 780

Ile Glu Tyr Leu Val Ser Phe Gly Val Trp Ile Arg Thr Pro Pro Ala
785                 790                 795                 800

Tyr Arg Pro Pro Asn Ala Pro Ile Leu Ser Ser Ala Asp Leu Glu Val
                805                 810                 815

Val Thr Ser Thr Trp Val Leu Val Gly Gly Val Leu Met Asp Ile Asp
            820                 825                 830

Pro Tyr Lys Glu Phe Gly Ala Thr Val Glu Leu Leu Ser Phe Leu Pro
        835                 840                 845

Ser Asp Phe Phe Pro Ser Val Arg Asp Leu Leu Asp Thr Ala Ser Ala
    850                 855                 860

Leu Tyr Arg Glu Ala Leu Glu Ser Ser Ala Asp Leu Glu Val Val Thr
865                 870                 875                 880

Ser Thr Trp Val Leu Val Gly Gly Val Leu Pro Glu His Cys Ser Pro
                885                 890                 895

His His Thr Ala Leu Arg Gln Ala Ile Leu Cys Trp Gly Glu Leu Met
            900                 905                 910

Thr Leu Ala Thr Trp Val Gly Val Asn Leu Glu Asp Pro Ala Ser Arg
        915                 920                 925

Asp Leu Val Val Ser
    930
```

<210> SEQ ID NO 87
<211> LENGTH: 2802
<212> TYPE: DNA
<213> ORGANISM: Artificial Sequence
<220> FEATURE:
<223> OTHER INFORMATION: CONSTR-8 NS3/4A-HBcAg Fragments

<400> SEQUENCE: 87

```
atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgcccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480
```

acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccaccccccc cggcagcgtg accgtgcccc accccaacat cgaggaggtg 1020
gccctgagca ccaccggcga gatccccttc tacggcaagg ccatccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggcccccggc 1440
gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac cccccctgctg 1800 taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980
atcgtgctga gcggcaagcc cgccatcatc cccgaccgcg aggtgctgta ccgcgagttc 2040
gacgagatgg aggagtgcag ccagcacctg ccctacatcg agcagggcac cctgcccgag 2100
accaccgtgg tgcgccgccg cggccgcagc cccccgccgcc gcacccccag cccccgccgc 2160
cgccgcagcc agagccccccg ccgccgccgc agccagagcc gcgagagcca gtgcagcgcc 2220
gacctggagg tggtgaccag cacctgggtg ctggtgggcg gcgtgctgta cgtgaacacc 2280
aacatgggcc tgaagttccg ccagctgctg tggttccaca tcagctgcct gaccttcggc 2340
cgcgagaccg tgatcgagta cctggtgagc ttcggcgtgt ggatccgcac cccccccgcc 2400
taccgccccc ccaacgcccc catcctgagc agcgccgacc tggaggtggt gaccagcacc 2460
tgggtgctgg tgggcggcgt gctgatggac atcgacccct acaaggagtt cggcgccacc 2520
gtggagctgc tgagcttcct gcccagcgac ttcttcccca gcgtgcgcga cctgctggac 2580
accgccagcg ccctgtaccg cgaggccctg gagagcagcg ccgacctgga ggtggtgacc 2640
agcacctggg tgctggtggg cggcgtgctg cccgagcact gcagccccca ccacaccgcc 2700
ctgcgccagg ccatcctgtg ctggggcgag ctgatgaccc tggccacctg ggtgggcgtg 2760
aacctggagg accccgccag ccgcgacctg gtggtgagct ag 2802

<210> SEQ ID NO 88

-continued

<211> LENGTH: 933
<212> TYPE: PRT
<213> ORGANISM: Artificial Sequence
<220> FEATURE:
<223> OTHER INFORMATION: CONSTR-9 NS3/4A-HBcAg Fragments

<400> SEQUENCE: 88

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380
```

-continued

```
Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Tyr Val Asn Thr Asn Met Gly Leu
    690                 695                 700

Lys Phe Arg Gln Leu Leu Trp Phe His Ile Ser Cys Leu Thr Phe Gly
705                 710                 715                 720

Arg Glu Thr Val Ile Glu Tyr Leu Val Ser Phe Gly Val Trp Ile Arg
                725                 730                 735

Thr Pro Pro Ala Tyr Arg Pro Pro Asn Ala Pro Ile Leu Ser Ser Ala
            740                 745                 750

Asp Leu Glu Val Val Thr Ser Thr Trp Val Leu Val Gly Gly Val Leu
        755                 760                 765

Thr Leu Pro Glu Thr Thr Val Val Arg Arg Arg Gly Arg Ser Pro Arg
    770                 775                 780

Arg Arg Thr Pro Ser Pro Arg Arg Arg Arg Ser Gln Ser Pro Arg Arg
785                 790                 795                 800

Arg Arg Ser Gln Ser Arg Glu Ser Gln Cys Ser Ala Asp Leu Glu Val
                805                 810                 815
```

```
Val Thr Ser Thr Trp Val Leu Val Gly Gly Val Leu Met Asp Ile Asp
            820                 825                 830

Pro Tyr Lys Glu Phe Gly Ala Thr Val Glu Leu Leu Ser Phe Leu Pro
        835                 840                 845

Ser Asp Phe Phe Pro Ser Val Arg Asp Leu Leu Asp Thr Ala Ser Ala
    850                 855                 860

Leu Tyr Arg Glu Ala Leu Glu Ser Ser Ala Asp Leu Glu Val Val Thr
865                 870                 875                 880

Ser Thr Trp Val Leu Val Gly Gly Val Leu Pro Glu His Cys Ser Pro
                885                 890                 895

His His Thr Ala Leu Arg Gln Ala Ile Leu Cys Trp Gly Glu Leu Met
            900                 905                 910

Thr Leu Ala Thr Trp Val Gly Val Asn Leu Glu Asp Pro Ala Ser Arg
        915                 920                 925

Asp Leu Val Val Ser
    930


<210> SEQ ID NO 89
<211> LENGTH: 2802
<212> TYPE: DNA
<213> ORGANISM: Artificial Sequence
<220> FEATURE:
<223> OTHER INFORMATION: CONSTR-9 NS3/4A-HBcAg Fragments

<400> SEQUENCE: 89

atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgccccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480

acccgcggcg tggccaaggc cgtggacttc atccccgtgg agagcctgga gaccaccatg     540

cgcagccccg tgttcagcga caacagcagc ccccccgccg tgccccagag ctaccaggtg     600

gcccacctgc acgcccccac cggcagcggc aagagcacca aggtgcccgc cgcctacgcc     660

gcccagggct acaaggtgct ggtgctgaac cccagcgtgg ccgccaccat gggcttcggc     720

gcctacatga gcaaggccca cggcatcgac cccaacatcc gcaccggcgt gcgcaccatc     780

accaccggca gccccatcac ctacagcacc tacggcaagt tcctggccga cggcggctgc     840

agcggcggcg cctacgacat catcatctgc gacgagtgcc acagcaccga cgccaccagc     900

atcctgggca tcggcaccgt gctggaccag gccgagaccg ccggcgcccg cctgaccgtg     960

ctggccaccg ccaccccccc cggcagcgtg accgtgcccc accccaacat cgaggaggtg    1020

gccctgagca ccaccggcga gatccccttc tacggcaagg ccatccccct ggaggccatc    1080

aagggcggcc gccacctgat cttctgccac agcaagaaga agtgcgacga gctggccgcc    1140

aagctggtgg ccctgggcgt gaacgccgtg gcctactacc gcggcctgga cgtgagcgtg    1200

atccccacca gcggcgacgt ggtggtggtg gccaccgacg ccctgatgac cggcttcacc    1260

ggcgacttcg acagcgtgat cgactgcaac acctgcgtga cccagaccgt ggacttcagc    1320

ctggacccca ccttcaccat cgagaccatc accctgcccc aggacgccgt gagccgcacc    1380
```

```
cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg  1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcta cgtgaacacc   2100

aacatgggcc tgaagttccg ccagctgctg tggttccaca tcagctgcct gaccttcggc   2160

cgcgagaccg tgatcgagta cctggtgagc ttcggcgtgt ggatccgcac cccccccgcc   2220

taccgccccc ccaacgcccc catcctgagc agcgccgacc tggaggtggt gaccagcacc   2280

tgggtgctgg tgggcggcgt gctgaccctg cccgagacca ccgtggtgcg ccgccgcggc   2340

cgcagccccc gccgccgcac ccccagcccc cgccgccgcc gcagccagag cccccgccgc   2400

cgccgcagcc agagccgcga gagccagtgc agcgccgacc tggaggtggt gaccagcacc   2460

tgggtgctgg tgggcggcgt gctgatggac atcgacccct acaaggagtt cggcgccacc   2520

gtggagctgc tgagcttcct gcccagcgac ttcttcccca gcgtgcgcga cctgctggac   2580

accgccagcg ccctgtaccg cgaggccctg gagagcagcg ccgacctgga ggtggtgacc   2640

agcacctggg tgctggtggg cggcgtgctg cccgagcact gcagccccca ccacaccgcc   2700

ctgcgccagg ccatcctgtg ctggggcgag ctgatgaccc tggccacctg ggtgggcgtg   2760

aacctggagg accccgccag ccgcgacctg gtggtgagct ag                      2802
```

<210> SEQ ID NO 90
<211> LENGTH: 10
<212> TYPE: PRT
<213> ORGANISM: Artificial Sequence
<220> FEATURE:
<223> OTHER INFORMATION: TP-5

<400> SEQUENCE: 90

```
Gly Leu Leu Gly Cys Ile Ile Thr Ser Leu
 1               5                  10
```

<210> SEQ ID NO 91
<211> LENGTH: 10
<212> TYPE: PRT
<213> ORGANISM: Artificial Sequence
<220> FEATURE:
<223> OTHER INFORMATION: TP-6

<400> SEQUENCE: 91

```
Thr Gly Ser Pro Ile Thr Tyr Ser Thr Tyr
 1               5                  10
```

<210> SEQ ID NO 92
<211> LENGTH: 9
<212> TYPE: PRT
<213> ORGANISM: Artificial Sequence

<220> FEATURE:
<223> OTHER INFORMATION: TP-7

<400> SEQUENCE: 92

Lys Leu Val Ala Gly Val Asn Ala Val
1 5

<210> SEQ ID NO 93
<211> LENGTH: 9
<212> TYPE: PRT
<213> ORGANISM: Artificial Sequence
<220> FEATURE:
<223> OTHER INFORMATION: TP-9

<400> SEQUENCE: 93

Cys Ile Asn Gly Val Cys Trp Thr Val
1 5

<210> SEQ ID NO 94
<211> LENGTH: 9
<212> TYPE: PRT
<213> ORGANISM: Artificial Sequence
<220> FEATURE:
<223> OTHER INFORMATION: TP-10

<400> SEQUENCE: 94

Leu Leu Cys Pro Ala Gly His Ala Val
1 5

<210> SEQ ID NO 95
<211> LENGTH: 9
<212> TYPE: PRT
<213> ORGANISM: Artificial Sequence
<220> FEATURE:
<223> OTHER INFORMATION: TP-11

<400> SEQUENCE: 95

Ala Thr Met Gly Phe Gly Ala Tyr Met
1 5

<210> SEQ ID NO 96
<211> LENGTH: 9
<212> TYPE: PRT
<213> ORGANISM: Artificial Sequence
<220> FEATURE:
<223> OTHER INFORMATION: TP-12

<400> SEQUENCE: 96

Tyr Leu Val Ala Tyr Gln Ala Thr Val
1 5

<210> SEQ ID NO 97
<211> LENGTH: 9
<212> TYPE: PRT
<213> ORGANISM: Artificial Sequence
<220> FEATURE:
<223> OTHER INFORMATION: TP-13

<400> SEQUENCE: 97

Thr Leu His Gly Pro Thr Pro Leu Leu
1 5

<210> SEQ ID NO 98
<211> LENGTH: 30
<212> TYPE: DNA
<213> ORGANISM: Artificial Sequence
<220> FEATURE:
<223> OTHER INFORMATION: NS4KR Primer

<400> SEQUENCE: 98
ccgtctagat cagcactctt ccatttcatc 30

<210> SEQ ID NO 99
<211> LENGTH: 30
<212> TYPE: DNA
<213> ORGANISM: Artificial Sequence
<220> FEATURE:
<223> OTHER INFORMATION: NS3KF primer

<400> SEQUENCE: 99
cctgaattca tggcgcctat cacggcctat 30

<210> SEQ ID NO 100
<211> LENGTH: 2061
<212> TYPE: DNA
<213> ORGANISM: Artificial Sequence
<220> FEATURE:
<223> OTHER INFORMATION: Hepatitis C virus NS3/4A coding region

<400> SEQUENCE: 100
atggcgccta tcacggccta tgcccagcag acaaggggcc ttttgggatg cataatcacc 60
agcttgaccg gccgggacaa aaaccaggtg gagggtgagg ttcagatcgt gtcaactgct 120
gcccagactt tcttggcaac ctgcattaac ggggtgtgtt ggactgtcta ccatggagcc 180
ggaacaagga ccattgcgtc acctaagggt cctgttatcc agatgtacac caatgtggac 240
caagacctcg taggctggcc cgctccccaa ggtgcccgct cattaacacc atgcacttgc 300
ggctcctcgg acctttacct ggtcacgagg cacgccgatg tcattcctgt gcgccgacgg 360
ggtgatggca ggggcagcct gctttcgccc cggcctatct cttacttgaa aggctcctcg 420
ggaggccctc tgctgtgccc cgcaggacat gccgtaggca tattcagagc cgcggtatgc 480
acccgtggag tggctaaggc ggtggacttc atccccgtag agagcttaga gacaaccatg 540
aggtccccgg tgttctcaga caactcctcc ccaccagcag tgccccagag ctaccaagtg 600
gcccacctgc atgctcccac cggcagcggt aagagcacca aggtcccggc cgcatacgca 660
gctcagggct acaaggtgct ggtgctcaac ccctccgttg ctgcaacaat gggctttggt 720
gcttacatgt ccaaggccca tgggattgat cctaacatca ggactggggt gaggacaatt 780
actactggca gcccgatcac gtattccacc tacggcaagt tccttgccga cggcgggtgt 840
tcagggggtg cttatgacat aataatttgt gacgagtgcc actccacgga tgcaacatcc 900
atcttgggca ttggcactgt ccttgaccaa gcagagaccg cgggggcgag actgactgtg 960
ctcgccaccg ctacccctcc gggctccgtc actgtgcccc atcctaacat cgaggaggtt 1020
gctctgtcca ctaccggaga gatccccttt tatggcaagg ctattcccct tgaagcaatt 1080
aaggggggga gacatctcat cttctgccac tcaaagaaga agtgcgacga gctcgccgca 1140
aaactggtcg cgttgggcgt caatgccgtg gcttactacc gcggccttga tgtgtccgtc 1200
atcccgacca gtggtgacgt tgtcgtcgtg gcaactgacg ccctcatgac cggctttacc 1260
ggcgacttcg attcggtgat agactgcaac acgtgtgtca cccagacagt cgacttcagc 1320
cttgacccta ccttcaccat tgagacaatc acgcttcccc aggatgctgt ctcccgtact 1380
caacgtcggg gtaggactgg cagagggaag ccaggcatct acagatttgt ggcaccgggg 1440
gagcgtcctt ctggcatgtt tgactcgtct gtcctctgcg agtgctatga cgcgggttgt 1500
gcttggtatg agcttacgcc cgccgagacc acagttaggc tacgagcata catgaacacc 1560
ccgggacttc ccgtgtgcca agaccatctt gaattttggg agggcgtctt tacgggtctc 1620

-continued

```
acccacatag acgcccactt cctatcccag acaaagcaga gtggggaaaa ccttccctat   1680

ctggtagcgt accaagccac cgtgtgcgct agagctcaag cccctccccc gtcgtgggac   1740

cagatgtgga agtgcttgat ccgtctcaag cccaccctcc atgggccaac acctctgcta   1800

tatagactgg gcgctgtcca gaatgaagtc accctgacgc acccagtcac caagtatatc   1860

atgacatgta tgtcggctga cctggaggtc gtcacgagta cctgggtgct cgttggcggc   1920

gttctggctg ctttggccgc gtattgccta tccacaggct gcgtggtcat agtaggtagg   1980

attgtcttgt ccggaaagcc ggcaatcata cccgacaggg aagtcctcta ccgggagttc   2040

gatgaaatgg aagagtgctg a                                             2061
```

<210> SEQ ID NO 101
<211> LENGTH: 24
<212> TYPE: DNA
<213> ORGANISM: Artificial Sequence
<220> FEATURE:
<223> OTHER INFORMATION: NS3KF Primer

<400> SEQUENCE: 101

```
ccacgcggcc gcgacgacct acag                                            24
```

<210> SEQ ID NO 102
<211> LENGTH: 262
<212> TYPE: PRT
<213> ORGANISM: Artificial Sequence
<220> FEATURE:
<223> OTHER INFORMATION: c.o. Stork HBcAg w/ human HBcAg insert (87-129)

<400> SEQUENCE: 102

```
Met Asp Val Asn Ala Ser Arg Ala Leu Ala Asn Val Tyr Asp Leu Pro
 1               5                  10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Thr Pro Val Pro Asp Gly Tyr Leu Ile Ser His Asn Glu Ala
                85                  90                  95

Gln Glu Leu Pro Leu Asn Asp Leu Phe Val Leu Gln Glu Glu Arg Ile
            100                 105                 110

Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ser Asn
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Ser Arg Asn Gln Thr Lys Gly Val Arg Lys
        195                 200                 205

Pro Arg Gly Leu Glu Pro Arg Arg Arg Lys Val Lys Thr Thr Val Val
    210                 215                 220
```

```
Tyr Gly Arg Arg Arg Ser Lys Ser Arg Gly Arg Arg Ser Ser Pro Ser
225                 230                 235                 240

Gln Arg Ala Gly Ser Pro Ile Pro Arg Asn Arg Glu Asn Gln Ser Arg
                245                 250                 255

Ser Ser Ser Pro Arg Glu
            260


<210> SEQ ID NO 103
<211> LENGTH: 789
<212> TYPE: DNA
<213> ORGANISM: Artificial Sequence
<220> FEATURE:
<223> OTHER INFORMATION: c.o. Stork HBcAg w/ human HBcAg insert (87-129)

<400> SEQUENCE: 103

atggacgtga acgccagcag agccctggcc aacgtgtacg acctgcccga cgacttcttc      60

ccccagatcg acgacctggt gagagacgcc aaggacgccc tggagcccta ctggaaggcc     120

gagaccatca agaagcacgt gctgatcgcc acccacttcg tggacttgat cgaggacttc     180

tggcagacca cccagggcat gagccagatc gccgacgccc tgagagccgt gatccccccc     240

accaccaccc ccgtgcccga cggctacctg atcagccaca acgaggccca ggagctcccc     300

ctgaacgacc tgttcgtgct gcaggaggag agaatcgtga acttccagcc cgactacccc     360

atcaccgcca gaattcacac ccacctgaga gtgtacacca agctgaacga gcaggccctg     420

gacaaggcca gaagactgct gtggtggcac tacaactgcc tgctgtgggg cgagagcaac     480

gtgaccaact acatcagcag actgagaacc tggctgagca cccccgagaa gtacagaggc     540

aaggacgccc ccaccatcga ggccatcacc agacccatcc aggtggccca gggcagcaga     600

aaccagacca agggcgtgag aaagcccaga ggcctggagc ccagaagaag aaaggtgaag     660

accaccgtgg tgtacggcag aagaagaagc aagagcagag gcagaagaag cagccccagc     720

cagagagccg gcagccccat ccccagaaac agagagaacc agagcagaag cagcagcccc     780

agagagtga                                                             789


<210> SEQ ID NO 104
<211> LENGTH: 262
<212> TYPE: PRT
<213> ORGANISM: Artificial Sequence
<220> FEATURE:
<223> OTHER INFORMATION: c.o. Heron HBcAg w/ human HBcAg insert (87-129)

<400> SEQUENCE: 104

Met Asp Val Asn Ala Ser Arg Ala Leu Ala Asn Val Tyr Asp Leu Pro
 1               5                  10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Val Pro Val Pro Glu Gly Phe Leu Ile Thr His Ser Glu Ala
                85                  90                  95

Glu Glu Leu Pro Leu Asn Asp Leu Phe Ser Leu Gln Glu Glu Arg Ile
            100                 105                 110

Val Asn Phe Gln Pro Asp Tyr Pro Ile Thr Ala Arg Ile His Thr His
```

```
        115                 120                 125

Leu Arg Val Tyr Thr Lys Leu Asn Glu Gln Ala Leu Asp Lys Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Gly Arg Asn Gln Thr Lys Gly Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Gly Arg Arg Ser Ser Pro Ser
225                 230                 235                 240

Gln Arg Ala Gly Ser Pro Leu Pro Arg Asn Arg Gly Asn Gln Thr Arg
                245                 250                 255

Ser Pro Ser Pro Arg Glu
            260


<210> SEQ ID NO 105
<211> LENGTH: 789
<212> TYPE: DNA
<213> ORGANISM: Artificial Sequence
<220> FEATURE:
<223> OTHER INFORMATION: c.o. Heron HBcAg w/ human HBcAg insert (87-129)

<400> SEQUENCE: 105

atggacgtga acgccagcag agccctggcc aacgtgtacg acctgcccga cgacttcttc      60

ccccagatcg acgacctggt gagagacgcc aaggacgccc tggagcccta ctggaaggcc     120

gagaccatca agaagcacgt gctgatcgcc acccacttcg tggacttgat cgaggacttc     180

tggcagacca cccagggcat gagccagatc gccgacgccc tgagagccgt gatccccccc     240

accaccgtgc ccgtgcccga gggcttcctg atcacccaca gcgaggccga ggagctcccc     300

ctgaacgacc tgttcagtct gcaggaggag agaatcgtga acttccagcc cgactacccc     360

atcaccgcca gaattcacac ccacctgaga gtgtacacca agctgaacga gcaggccctg     420

gacaaggcca gaagactgct gtggtggcac tacaactgcc tgctgtgggg cgaggccacc     480

gtgaccaact acatcagcag actgagaacc tggctgagca cccccgagaa gtacagaggc     540

aaggacgccc ccaccatcga ggccatcacc agacccatcc aggtggccca gggcggcaga     600

aaccagacca agggcaccag aaagcccaga ggcctggagc ccagaagaag aaaggtgaag     660

accaccgtgg tgtacggcag aagaagaagc aagagcagag gcagaagaag cagccccagc     720

cagagagccg gcagcccccct gcccagaaac agaggcaacc agaccagaag ccccagcccc     780

agagagtga                                                              789


<210> SEQ ID NO 106
<211> LENGTH: 9
<212> TYPE: DNA
<213> ORGANISM: Artificial Sequence
<220> FEATURE:
<223> OTHER INFORMATION: Kozak Sequence

<400> SEQUENCE: 106

gcaccatgg                                                                9
```